US008053450B2

(12) United States Patent
Herpin et al.

(10) Patent No.: US 8,053,450 B2
(45) Date of Patent: Nov. 8, 2011

(54) AMINO-BENZAZOLES AS P2Y$_1$ RECEPTOR INHIBITORS WITH PYRIDINE RING AND HETEROCYCLIC COMPONENTS

(75) Inventors: Timothy F. Herpin, Princeton, NJ (US); George C. Morton, Collegeville, PA (US); Robert P. Rehfuss, North Wales, PA (US); R. Michael Lawrence, Yardley, PA (US); Michael A. Poss, Lawrenceville, NJ (US); Jacques Y. Roberge, Princeton, NJ (US); Timur Gungor, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 874 days.

(21) Appl. No.: 12/104,732

(22) Filed: Apr. 17, 2008

(65) Prior Publication Data

US 2008/0275090 A1 Nov. 6, 2008

Related U.S. Application Data

(62) Division of application No. 11/038,862, filed on Jan. 19, 2005, now Pat. No. 7,470,712.

(60) Provisional application No. 60/537,869, filed on Jan. 21, 2004, provisional application No. 60/638,167, filed on Dec. 22, 2004.

(51) Int. Cl.
*A61K 31/4436* (2006.01)
*C07D 417/12* (2006.01)

(52) U.S. Cl. .................... 514/338; 546/270.1

(58) Field of Classification Search ................ 546/270.1; 514/338
See application file for complete search history.

(56) References Cited

U.S. PATENT DOCUMENTS

| | | | |
|---|---|---|---|
| 4,882,342 | A | 11/1989 | von der Saal et al. |
| 4,954,498 | A | 9/1990 | Mertens et al. |
| 5,322,847 | A | 6/1994 | Marfat et al. |
| 6,492,383 | B1 | 12/2002 | Munchhof et al. |
| 7,388,021 | B2 | 6/2008 | Chao et al. |
| 2002/0016460 | A1 | 2/2002 | Snow et al. |
| 2002/0132842 | A1 | 9/2002 | Hofmeister et al. |
| 2003/0054298 | A1 | 3/2003 | Suzuki et al. |
| 2004/0087626 | A1 | 5/2004 | Renhowe et al. |
| 2005/0261244 | A1 | 11/2005 | Tuerdi et al. |
| 2007/0021456 | A1 | 1/2007 | Mitjans et al. |

FOREIGN PATENT DOCUMENTS

| | | |
|---|---|---|
| DE | 2133649 A1 | 1/1972 |
| EP | 419210 | 2/1991 |
| GB | 1171904 | 11/1969 |
| JP | 2001199983 | 7/2001 |
| WO | WO 9808818 | 3/1998 |
| WO | WO 0005223 | 2/2000 |
| WO | WO 03082272 | 10/2003 |
| WO | WO 2004094372 | 11/2004 |

OTHER PUBLICATIONS

Das et al., "Discovery of 2-Amino-heteroaryl-benzothiazole-6-anilides as Potent p56Lck Inhibitors", Bioorganic & Medicinal Chemistry Letters, vol. 13, pp. 2587-2590, 2003.
Pande, A. et al., "Synthesis of 2-Arylaminobenzothiazoles and Aryl Isothiocyanates as Antitubercular Agents", Indian Journal of Chemistry, Vo. 22B, pp. 311-312 (1983).
Abbracchio et al., "Purinoceptors: Are There Families of P2X and P2Y Punnoceptors?", Pharmac. Ther., vol. 64, pp. 445-475, 1994.
Abbracchio et al., "Characterization of theUDP-glucose receptor (re-named here the P2Y$_{14}$ receptor) adds diversity to the P2Y family", Trends in Pharmacological Sciences, vol. 24, No. 2, pp. 52-55, Feb. 2003.
Angelo et al., "$N^2$-1H-Benzimidazol-2-yl-$N^4$-phenyl-2,4-pyrimidinediamines and $N^2$-1H-Benzimidazol-2-yl-5,6,7,8-tetrahydro-$N^4$-phenyl-2,4-quinazolinediamines as Potential Antifilarial Agents", J. Med. Chem, vol. 26, pp. 1311-1316, 1983.
Boeynaems et al., "Overview of P2Y Receptors as Therapeutic Targets", Drug Development Research, vol. 52, pp. 187-189, 2001.
Burnstock et al., "P2 Purinergic Receptors: Modulation of Cell Function and Therapeutic Potential", The Journal of Phamacology and Experimental Therapeutics, vol. 295, No. 3, pp. 862-869, 2000.
Chaudhari et al., "Synthesis and anthelmintic activity of new pyrido [3,2d] thiazoles", Bulletin of Haffkine Institute, Haffkine Inst. Bombay, India, vol. 8 No. 3, pp. 87-92, 1980.
Daniel et al., "Molecular Basis for ADP-induced Platelet Activation", The Journal of Biological Chemistry, vol. 273, No. 4, Issue of Jan. 23, pp. 2024-2029, 1998.
Fabre et al., "Decreased platelet aggregation increased bleeding time and resistance to thromboembolism in P2Y$_1$-deficient rate", Nature Medicine, vol. 5, No. 10, pp. 1199-1202, Oct. 1999.
Hechler et al., "The P2Y$_1$ receptor, necessary but not sufficient to support full ADP-induced platelet aggregation, is not the target of the drug clopidogrel", British Journal of Haematology, vol. 103, pp. 858-866, 1998.
Janssens et al., "Cloning and Tissue Distribution of the Human P2Y$_1$ Receptor", Biochemical and Biophysical Research Communications, Article No. 0640, vol. 221, pp. 588-593, 1996.
Jin et al., "Coactivation of two different G protein-coupled receptors is essential for ADP-induced platelet aggregation", Proc. Natl. Acad. Sci., vol. 95, pp. 8070-8074, 1998.
Kolodyazhnaya et al,. "Nitrogen-Containing Bisheterocyclic Systems", Khimiya Geterotsikli Soedin., vol. 6, No. 2, pp. 238-244, 1970.
Lenain, et al., "Inhibition of localized thrombosis in P2Y$_1$-deficient mice and rodents treated with MRS2179, a P2Y$_1$ receptor antagonist", Journal of Thrombosis and Haemostasis, vol. 1, pp. 1144-1149, 2003.

(Continued)

*Primary Examiner* — Patricia Morris
(74) *Attorney, Agent, or Firm* — Jing G. Sun

(57) ABSTRACT

The present invention provides novel amino-benzazoles and analogues thereof, which are selective inhibitors of the human P2Y$_1$ receptor. The invention also provides for various pharmaceutical compositions of the same and methods for treating diseases responsive to modulation of P2Y$_1$ receptor activity.

14 Claims, No Drawings

OTHER PUBLICATIONS

Leon et al., "Key Role of the P2Y$_1$ Receptor in Tissue Factor-Induced Thrombin-Dependent Acute Thromboembolism Studies in P2Y$_1$-Knockout Mice and Mice Treated with P2Y1 Antagonist", Circulation, vol. 103, pp. 718-723, 2001.

Norenberg, et al., "Characterization and possible function of adenosine 5'-triphosphate receptors in activated rat microglia", Br. J. Pharmacol., vol. 111, pp. 942-950, 1994.

Ochiai, et al., "New orally active PDE4 inhibitors with therapeutic potential", Bioorganic & Medicinal Chemistry Letters, vol. 14, pp. 29-32, 2004.

Salter et al., "ATP Causes Release of Intracellular Ca$^{2+}$ via the Phospholipase Cβ/IP$_3$ Pathway in Astrocytes from the Dorsal Spinal Cord", The Journal of Neuroscience, vol. 15(4), pp. 2961-2971, 1995.

Savi et al., "Role of P2Y1 purinoceptor in ADP-induced platelet activation", FEBS Letters, vol. 422, pp. 291-295, 1998.

Simonov et al., "Heterylation of five-membered nitrogen-heterocycles by 1-methyl-2-chlorobenzimidazole", Khim. Geterotsikl. Soedin., pp. 141-145, 1967, Abstract.

Baurand, A. et al., "The P2Y$_1$ Receptor as a Target for New Antithrombotic Drugs: A Review of the P2Y$_1$ Antagonist MRS-2179", Cardiovascular Drug Reviews, vol. 21, pp. 67-76, 2003.

AMINO-BENZAZOLES AS P2Y$_1$ RECEPTOR INHIBITORS WITH PYRIDINE RING AND HETEROCYCLIC COMPONENTS

CROSS-REFERENCE TO RELATED APPLICATIONS

This case is a divisional of U.S. application Ser. No. 11/038,862, filed Jan. 19, 2005, now issued as U.S. Pat. No. 7,470,712, which claims the priority benefit of U.S. Provisional Application No. 60/537,869, filed Jan. 21, 2004 and the priority benefit of U.S. Provisional Application No. 60/638,167, filed Dec. 22, 2004, all of which are expressly incorporated fully herein by reference.

FIELD OF THE INVENTION

The present invention provides novel amino-benzazoles and analogues thereof, which are selective inhibitors of the human P2Y$_1$ receptor. The invention also provides for various pharmaceutical compositions of the same and methods for treating diseases responsive to modulation of P2Y$_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b and A3), which bind to and are activated by the nucleoside adenosine, and the P2 receptors, which comprise a second, more diverse class of receptors which are activated by a wide variety of nucleotides including ATP, ADP, UTP and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; P2Y$_1$, P2Y$_2$, P2Y$_4$, P2Y$_6$, P2Y$_{11}$, P2Y$_{12}$, and P2Y$_{13}$ (Boeynaems, J. M. et al. *Drug Development Research* 2000, 52, 187-9). In addition, an eighth receptor, P2Y$_{14}$, has been considered by some to be a member of this class although it does not respond to ribosylated nucleotides and is activated by UDP-glucose (Abbracchio, M. P. et al. *Trends Pharmacol. Sci.* 2003, 24, 52-5).

Several studies have suggested that modulators of specific members of the P2Y family of receptors could have therapeutic potential for the treatment of a variety of disorders (for review see Burnstock, G. et al., *J. Pharm. Exp Ther.* 2000, 295, 862-9), including diabetes, cancer, CF, and treatment of ischemia-reperfusion injury (Abbracchio, M. P. et al., *Pharmacol. Ther.* 1994, 64, 445-475). P2Y$_1$ receptors, almost ubiquitous among human organs (Jassens, R. et al., *Biochem. Biophys. Res. Comm.* 1996, 221, 588-593) have been identified on microglia (Norenberg, W. et al., *Br. J. Pharmacol.* 1994, 111, 942-950) and on astrocytes (Salter M. W. et al., *J. Neurosci.* 1995, 15, 2961-2971). Extracellular ATP activates microglial and/or astrocytes via P2Y receptors and leads directly to the release of inflammatory mediators. Microglia and astrocytes are believed to play a role in the progression of Alzheimer's disease and other CNS inflammatory disorders such as stroke and multiple sclerosis.

Two members of the P2Y family, P2Y$_1$ and P2Y$_{12}$, are of particular interest as they have now both been shown to act as important receptors for ADP in platelets (Jin, S. et al., *Proc. Natl. Acad. Sci.* 1998, 95, 8070). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both P2Y$_1$ and P2Y$_{12}$ to produce two separate intracellular signals which synergize together to produce complete platelet activation (Jin, J. et al. *Proc. Natl. Acad. Sci.* 1998, 273, 2030-4). The first signal arises from ADP driven activation of the P2Y$_1$ receptor and can most easily be tracked by measuring the transitory increase in intracellular free Ca$^{+2}$. This signal appears to mediate the initial shape change reaction and to initiate the process of platelet activation. The second signal appears to be derived from ADP activation of the P2Y$_{12}$ receptor and serves to consolidate the process and produce an irreversible platelet aggregate. Using three structurally related but distinct inhibitors of P2Y$_1$ (A3P5P, A3P5PS and A2P5P) (Daniel, J. L. et al., *J. Biol. Chem.* 1998, 273, 2024-9; Savi, P. et al., *FEBS Letters* 1998, 422, 291-5; Hechler, B. et al., *Br. J. Haematol.* 1998, 103, 858-66.) were the first to publish the observation that the inhibition of P2Y$_1$ activity alone could block ADP-driven aggregation independently of the P2Y$_{12}$ receptor. Although inhibition of platelet reactivity is often thought of as firm evidence of an anti-thrombotic activity, these antagonists lacked the necessary pharmacological properties for in vivo study. The first direct demonstration that inhibition of P2Y$_1$ activity could lead to an anti-thrombotic effect in vivo was reported by Leon, C. et al., *Circulation* 2001, 103, 718-23, in a model of thromboplastin induced thromboembolism using both a P2Y$_1$ knock-out mouse and the P2Y$_1$ antagonist MRS-2179 (Baurand, A. et al., *Cardiovascular Drug Reviews* 2003, 21, 67-76). These results were subsequently extended to include the inhibition of both venous and arterial thrombosis in the rat (Lenain, N. et al., *J. Thromb. Haemost.* 2003, 1, 1144-9) and confirmed by a second laboratory using an independently derived P2Y$_1$ knock-out mouse (Fabre, J-E. et al., *Nature Medicine* 1999, 5, 1199-1202). Taken together, these data suggest that the discovery of novel P2Y$_1$ antagonists with improved pharmaceutical characteristics could have significant utility in the treatment of a variety of thromboembolic disorders.

SUMMARY OF THE INVENTION

Accordingly, the present invention provides novel amino-benzazoles, which are useful as selective inhibitors of the P2Y$_1$ receptor including stereoisomers, pharmaceutically acceptable salts, hydrates, or prodrugs thereof.

The present invention also provides processes and intermediates for making the compounds of the present invention or a stereoisomer or a pharmaceutically acceptable salt, solvate, or prodrug form thereof.

The present invention also provides pharmaceutical compositions comprising a pharmaceutically acceptable carrier and a therapeutically effective amount of at least one of the compounds of the present invention or a pharmaceutically acceptable salt, solvate, or prodrug form thereof.

The present invention also provides a method for modulation of platelet reactivity comprising administering to a host in need of such treatment a therapeutically effective amount of at least one of the compounds of the present invention or a pharmaceutically acceptable salt, solvate, or prodrug form thereof.

The present invention also provides a method for treating thromboembolic disorders comprising administering to a host in need of such treatment a therapeutically effective amount of at least one of the compounds of the present invention or a pharmaceutically acceptable salt, solvate, or prodrug form thereof.

The present invention also provides novel amino-benzazoles for use in therapy for other disease states which are responsive to modulation of $P2Y_1$ activity.

The present invention also provides the use of novel amino-benzazoles for the manufacture of a medicament for the treatment of a thromboembolic or other disorders.

These and other embodiments, which will become apparent during the following detailed description, have been achieved by the inventors' discovery that the presently claimed novel compounds of the present invention, or pharmaceutically acceptable salt or prodrug forms thereof, are effective $P2Y_1$ inhibitors.

DETAILED DESCRIPTION OF PREFERRED EMBODIMENTS

In a first embodiment, the present invention provides, inter alia, compounds of Formula (I):

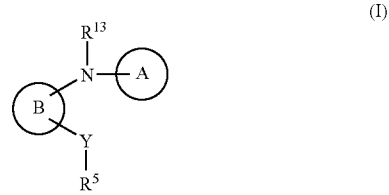

(I)

or a stereoisomer or pharmaceutically acceptable salts, solvates, or prodrugs thereof wherein:
ring A is selected from:

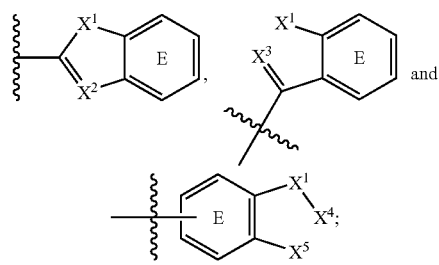

$X^1$ is $NR^{11}$, O, or $S(O)_p$;
$X^2$ is $CR^{11a}$ or N;
$X^3$ is $CR^{11a}$ or N;
$X^4$ is $CR^{11b}$ or N;
$X^5$ is $CR^{11b}$ or N;
ring E is selected from phenyl, pyridinyl, pyrimidyl, pyrazinyl, and pyridazinyl, and is substituted with 0-4 $R^1$;
ring B is phenyl substituted with 0-4 $R^7$, or a 5- to 6-membered heteroaryl comprising: carbon atoms and 1-4 ring heteroatoms selected from O, N, $NR^6$, and $S(O)_p$, and said heteroaryl is substituted with 0-4 $R^7$;
$R^1$ is, independently at each occurrence, F, Cl, Br, I, $OCF_3$, $CF_3$, —$CF_2CF_3$, —$(CR^fR^f)_r$—$OR^c$, $SR^c$, CN, $NO_2$, —$(CR^fR^f)_r$—$NR^8R^9$, —$(CR^fR^f)_r$—$C(O)R^c$, —$(CR^fR^f)_r$—$C(O)OR^c$, —$(CR^fR^f)_r$—$C(O)NR^8R^9$, —$C(O)NR^8(CR^fR^f)_r$$NR^8R^9$, —$NR^{10}(CR^fR^f)_nC(O)R^d$, —$NR^{10}CO(CR^fR^f)_nOR^c$, —$S(O)_pNR^8R^9$, —$NR^{10}S(O)_pR^d$, —$S(O)R^d$, —$S(O)_2R^d$, —$N(C_{1-4}\text{ alkyl})_3{}^+Cl^-$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —$(CR^fR^f)_r$—$C_{3-10}$ carbocycle substituted with 0-3 $R^b$, or —$(CR^fR^f)_r$-5- to 12-membered heterocycle comprising: carbon atoms and 1-4 heteroatoms selected from N, O, and $S(O)_p$, and substituted with 0-3 $R^b$;

alternatively, two $R^1$s on the two adjacent carbon atoms are combined, with the carbon atoms to which they are attached, form a 5- or 6-membered carbocycle or heterocycle comprising: carbon atoms and 0-3 additional heteroatoms selected from N, NH, O, and $S(O)_p$, and substituted with 0-2 $R^b$;
Y is $NR^{12}$, O, or $S(O)_p$;
$R^5$ is a $C_{3-10}$ carbocycle substituted with 0-3 $R^b$, or a 5- to 10-membered heterocycle comprising: carbon atoms and 1-4 heteroatoms selected from N, O, and $S(O)_p$, and substituted with 0-3 $R^b$;
$R^6$ is H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, $(C_{1-6}$ alkyl)C(O)—, $(C_{3-6}$ cycloalkyl)$C_{1-3}$ alkyl-C(O)—, $(C_{3-6}$ cycloalkyl)C(O)—, phenyl-C(O)—, benzyl-C(O)—, benzyl-S(O)$_2$—, $(C_{1-6}$ alkyl)NHC(O)—, $(C_{1-6}$ alkyl)$_2$NC(O)—, phenyl-NHC(O)—, benzyl-NHC(O)—, phenyl)($C_{1-6}$ alkyl)NC(O)—, (benzyl)($C_{1-6}$ alkyl)NC(O)—, $(C_{1-6}$ alkyl)-S(O)$_2$—, phenyl-S(O)$_2$—, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, O, and $S(O)_p$, and substituted with 0-3 $R^b$;
$R^7$ is H, F, Cl, Br, I, $OCF_3$, $CF_3$, $OR^c$, $SR^c$, CN, $NO_2$, —$NR^8R^9$, —$C(O)R^c$, —$C(O)OR^c$, —$C(O)NR^8R^9$, —$NR^{10}C(O)R^d$, —$S(O)_pNR^8R^9$, —$S(O)R^d$, —$S(O)_2R^d$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, O, and $S(O)_p$, and substituted with 0-3 $R^b$;

alternatively, two $R^7$s on the two adjacent carbon atoms are combined to form a 5- to 7-membered carbocyclic or heterocyclic ring comprising: carbon atoms and 0-3 ring heteroatoms selected from O, N, $NR^{6a}$, and $S(O)_p$, and said carbocyclic or heterocyclic ring is substituted with 0-3 $R^{7a}$;
alternatively, $R^6$ may combine with the $R^7$ on the adjacent carbon atom to form a 5- to 7-membered carbocyclic or heterocyclic ring comprising: carbon atoms and 0-3 ring heteroatoms selected from O, N, $NR^{6a}$, and $S(O)_p$, and said carbocyclic or heterocyclic ring is substituted with 0-3 $R^{7a}$;
$R^{6a}$ is H, $C_{1-4}$ alkyl, $(C_{1-4}$ alkyl)C(O)—, phenyl-C(O)—, benzyl-C(O)—, benzyl-S(O)$_2$—, $(C_{1-4}$ alkyl)NHC(O)—, $(C_{1-4}$ alkyl)$_2$NC(O)—, phenyl-NHC(O)—, benzyl-NHC(O)—, $(C_{1-4}$ alkyl)-S(O)$_2$—, phenyl-S(O)$_2$—, phenyl substituted with 0-3 $R^b$, or benzyl substituted with 0-3 $R^b$;
$R^{7a}$ is H, F, Cl, Br, I, $OCF_3$, $CF_3$, $OR^c$, $SR^c$, CN, $NO_2$, —$NR^8R^9$, —$C(O)R^c$, —$C(O)OR^c$, —$C(O)NR^8R^9$, —$NR^{10}C(O)R^d$, —$S(O)_pNR^8R^9$, —$S(O)R^d$, —$S(O)_2R^d$, $C_{1-4}$ alkyl, phenyl substituted with 0-3 $R^b$, or benzyl substituted with 0-3 $R^b$;
$R^8$ is independently at each occurrence, H, $C_{1-6}$ alkyl substituted with 0-2 $R^j$, —$C(O)R^k$, —$C(O)OR^k$, —$C(O)NR^iR^i$, —$C(O)O$—$(C_{1-4}$ alkyl)-$C(O)OR^k$, —$S(O)_2R^k$, —$(CR^fR^f)_r$—$C_{3-10}$ carbocycle substituted with 0-3 $R^j$, or —$(CR^fR^f)_r$-5-10 membered heterocycle comprising: carbon atoms and 1-4 heteroatoms selected from N, O, and $S(O)_p$ and substituted with 0-3 $R^j$;
$R^9$ is, independently at each occurrence, H, $C_{1-6}$ alkyl, or —$(CH_2)_n$—$C_{3-10}$ carbocycle substituted with 0-2 $R^j$, or —(CH$_2$)$_r$-5-10 membered heterocycle comprising: carbon atoms and 1-4 heteroatoms selected from N, O, and S(O)$_p$ and substituted with 0-2 R$^j$;

alternatively, R$^8$ and R$^9$, when attached to the same nitrogen, combine to form a 5- to 10-membered heterocyclic ring comprising: carbon atoms and 0-2 additional heteroatoms selected from N, NR$^i$, O, and S(O)$_p$;

R$^{10}$ is, independently at each occurrence, H, C$_{1-6}$ alkyl substituted with 0-2 R$^{10a}$, C$_{2-6}$ alkenyl substituted with 0-2 R$^{10a}$, C$_{2-6}$ alkynyl substituted with 0-2 R$^{10a}$, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, O, and S(O)$_p$, and substituted with 0-3 R$^e$;

R$^{10a}$ is, independently at each occurrence, H, C$_{1-4}$ alkyl, OR$^c$, Cl, F, Br, I, =O, CF$_3$, CN, NO$_2$, —C(O)R$^c$, —C(O)OR$^c$, —C(O)NR$^8$R$^9$, or —S(O)$_p$R$^d$;

R$^{11}$ is H, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —C(O)R$^c$, —C(O)OR$^c$, —C(O)NR$^8$R$^9$, —C(O)O—(C$_{1-4}$ alkyl)-C(O)OR$^k$, —S(O)$_2$R$^k$, —S(O)$_2$NR$^8$R$^9$, —(CH$_2$)$_r$—C$_{3-10}$ carbocycle substituted with 0-3 R$^b$, or —(CH$_2$)$_r$-5- to 10-membered heterocycle comprising: carbon atoms and 1-4 heteroatoms selected from N, O, and S(O)$_p$, and substituted with 0-3 R$^b$;

R$^{11a}$ is H, F, Cl, Br, I, OCF$_3$, CF$_3$, OR$^c$, SR$^c$, CN, NO$_2$, —NR$^8$R$^9$, —C(O)R$^c$, —C(O)OR$^c$, —C(O)NR$^8$R$^9$, —NR$^{10}$C(O)R$^d$, —S(O)$_p$NR$^8$R$^9$, —S(O)R$^d$, S(O)$_2$R$^d$, C$_{1-6}$ alkyl substituted with 0-2 R$^a$, C$_{2-6}$ alkenyl substituted with 0-2 R$^a$, C$_{2-6}$ alkyl substituted with 0-2 R$^a$, —(CH$_2$)$_r$—C$_{3-10}$ carbocycle substituted with 0-3 R$^b$, or —(CH$_2$)$_r$-5- to 10-membered heterocycle comprising: carbon atoms and 1-4 heteroatoms selected from N, O, and S(O)$_p$, and substituted with 0-3 R$^b$;

R$^{11b}$ is H, F, Cl, Br, I, OCF$_3$, CF$_3$, —CF$_2$CF$_3$, —(CR$^f$R$^f$)$_r$—OR$^c$, SR$^c$, CN, NO$_2$, —(CR$^f$R$^f$)$_r$—NR$^8$R$^9$, —(CR$^f$R$^f$)$_r$—C(O)R$^c$, —(CR$^f$R$^f$)$_r$—C(O)OR$^c$, —(CR$^f$R$^f$)$_r$—C(O)NR$^8$R$^9$, —C(O)NR$^8$(CR$^f$R$^f$)$_t$NR$^8$R$^9$, —NR$^{10}$(CR$^f$R$^f$)$_n$C(O)R$^d$, —NR$^{10}$CO(CR$^f$R$^f$)$_n$OR$^c$, —S(O)$_p$NR$^8$R$^9$, —NR$^{10}$S(O)$_p$R$^d$, —S(O)R$^d$, —S(O)$_2$R$^d$, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —(CH$_2$)$_r$—C$_{3-10}$ carbocycle substituted with 0-3 R$^b$, or —(CH$_2$)$_r$-5- to 10-membered heterocycle comprising: carbon atoms and 1-4 heteroatoms selected from N, O, and S(O)$_p$, and substituted with 0-3 R$^b$;

R$^{12}$ is H, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —C(O)R$^c$, —C(O)OR$^c$, —C(O)NR$^8$R$^9$, —C(O)O—(C$_{1-4}$ alkyl)-C(O)OR$^k$, —S(O)$_2$R$^k$, —S(O)$_2$NR$^8$R$^9$, —(CH$_2$)$_r$—C$_{3-10}$ carbocycle substituted with 0-3 R$^b$, or —(CH$_2$)$_r$-5- to 10-membered heterocycle comprising: carbon atoms and 1-4 heteroatoms selected from N, O, and S(O)$_p$, and substituted with 0-3 R$^b$;

R$^{13}$ is H, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —C(O)R$^c$, —C(O)OR$^c$, —C(O)NR$^8$R$^9$, —S(O)$_2$R$^k$, —S(O)$_2$ NR$^8$R$^9$, —(CH$_2$)$_r$—C$_{3-10}$ carbocycle substituted with 0-3 R$^b$, or —(CH$_2$)$_r$-5- to 10-membered heterocycle comprising: carbon atoms and 1-4 heteroatoms selected from N, O, and S(O)$_p$, and substituted with 0-3 R$^b$;

R$^a$ is, independently at each occurrence, H, F, OCF$_3$, CF$_3$, OR$^c$, SR$^c$, CN, —NR$^8$R$^9$, —C(O)R$^c$, —C(O)OR$^c$, —C(O)NR$^8$R$^9$, —NR$^{10}$C(O)R$^b$, —S(O)$_p$NR$^8$R$^9$, —S(O)R$^d$, or —S(O)$_2$R$^d$;

R$^b$ is, independently at each occurrence, H, F, Cl, Br, I, OR$^c$, SR$^c$, CN, NO$_2$, CF$_3$, OCF$_3$, —C(O)R$^c$—C(O)OR$^c$, —C(O)NR$^8$R$^9$, —NR$^{10}$(O)R$^d$, —S(O)$_p$NR$^8$R$^9$, —S(O)$_p$R$^d$, —NR$^8$R$^9$, —Si(Me)$_3$, C$_1$-C$_4$ haloalkyl, C$_1$-C$_4$ haloalkyloxy-, C$_1$-C$_4$ alkyloxy-, C$_1$-C$_4$ alkylthio-, C$_1$-C$_4$ alkyl-C(O)—, C$_1$-C$_4$ alkyl-O—C(O)—, C$_1$-C$_4$ alkyl-C(O)NH—, C$_{1-6}$ alkyl substituted with 0-2 R$^j$, C$_{2-6}$ alkenyl substituted with 0-2 R$^j$, C$_{2-6}$ alkynyl substituted with 0-2 R$^j$, —(CH$_2$)$_r$—C$_{3-10}$ carbocycle substituted with 0-3 R$^j$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^j$;

alternatively, two R$^b$ groups attached to adjacent atoms, together with the atoms to which they are attached, form a 5- to 7-membered carbocyclic or heterocyclic ring comprising: carbon atoms and 0-2 heteroatoms selected from N, O, and S(O)$_p$, 0-1 carbonyl and 0-3 double bonds;

R$^c$ is, independently at each occurrence, H, C$_{1-6}$ alkyl substituted with 0-2 R$^j$, C$_{2-6}$ alkenyl substituted with 0-2 R$^j$, C$_{2-6}$ alkynyl substituted with 0-2 R$^j$, —(CH$_2$)$_r$—C$_{6-10}$ aryl substituted with 0-2 R$^e$, or —(CH$_2$)$_r$-5-10 membered heterocycle comprising: carbon atoms and 1-4 heteroatoms selected from N, O, and S(O)$_p$ and substituted with 0-2 R$^e$;

R$^d$ is, independently at each occurrence, CF$_3$, OH, C$_{1-4}$ alkoxy, C$_{1-6}$ alkyl substituted with 0-2 R$^j$, —(CH$_2$)$_r$—C$_{3-10}$ carbocycle substituted with 0-2 R$^e$, or —(CH$_2$)$_r$-5-10 membered heterocycle comprising: carbon atoms and 1-4 heteroatoms selected from N, O, and S(O), and substituted with 0-2 R$^e$;

R$^e$ is, independently at each occurrence, H, =O, OR$^g$, F, Cl, Br, I, CN, NO$_2$, —NR$^8$R$^9$, —C(O)R$^f$, —C(O)OR$^f$, —NR$^8$C(O)R$^f$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, or —(CH$_2$)$_n$-phenyl;

R$^f$ is, independently at each occurrence, H, C$_{1-6}$ alkyl, or —(CH$_2$)$_n$-phenyl;

R$^g$ is, independently at each occurrence, H, =O, OR$^f$, F, Cl, Br, I, CN, NO$_2$, —NR$^9$R$^9$, —C(O)R$^h$, —C(O)OR$^h$, —NR$^9$C(O)R$^h$, —C(O)NR$^9$R$^9$, —SO$_2$NR$^9$R$^9$, —NR$^9$SO$_2$NR$^9$R$^9$, —NR$^9$SO$_2$—C$_{1-4}$ alkyl, —NR$^9$SO$_2$CF$_3$, —NR$^9$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, or —(CH$_2$)$_n$-phenyl;

R$^h$ is, independently at each occurrence, H, C$_{1-6}$ alkyl, or —(CH$_2$)$_n$-phenyl;

R$^i$ is, independently at each occurrence, H, C$_{1-6}$ alkyl, —(CH$_2$)$_r$—C$_{6-10}$ aryl substituted with 0-2 R$^j$, or —(CH$_2$)$_r$-5-10 membered heterocycle comprising: carbon atoms and 1-4 heteroatoms selected from N, O, and S(O)$_p$ and substituted with 0-2 R$^j$;

R$^j$ is, independently at each occurrence, H, =O, OR$^f$, F, Cl, Br, I, CN, NO$_2$, —NR$^f$R$^h$, —C(O)R$^h$, —C(O)OR$^h$, —NR$^f$C(O)R$^h$, —C(O)NR$^f$R$^h$, —SO$_2$NR$^f$R$^h$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, or —(CH$_2$)$_n$-phenyl;

R$^k$ is, independently at each occurrence, C$_{1-6}$ alkyl, —(CH$_2$)$_r$—C$_{6-10}$ aryl substituted with 0-2 R$^j$, or —(CH$_2$)$_r$-5-10 membered heterocycle comprising: carbon atoms and 1-4 heteroatoms selected from N, O, and S(O)$_p$ and substituted with 0-2 R$^j$;

n, at each occurrence, is selected from 0, 1, 2, 3, and 4;

p, at each occurrence, is selected from 0, 1, and 2;

r, at each occurrence, is selected from 0, 1, 2, 3, and 4; and t, at each occurrence, is selected from 1, 2, 3 and 4;

provided that:
i) when ring B is

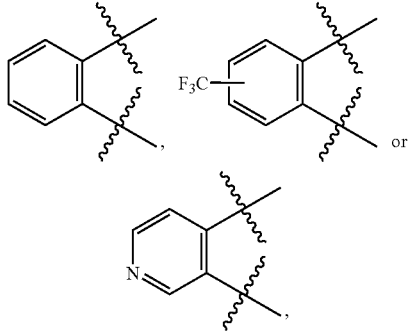

and ring A is

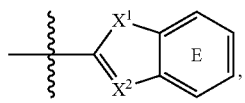

ring E is phenyl substituted with $OR^c$ or $SR^c$, then $R^c$ is other than aryl or heteroaryl;

ii) when ring B is

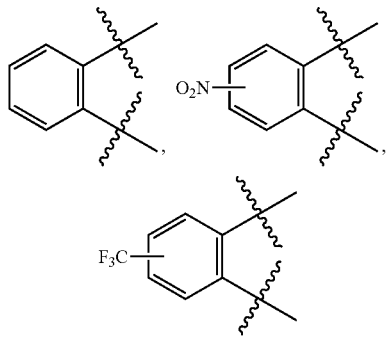

or

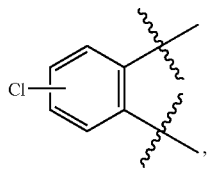

then $R^5$ is other than pyrrolidinyl, substituted pyrrolidinyl, phenyl, benzoimidazolyl or N-methyl substituted benzoimidazolyl;

iii) when ring A is thienopyrimidinyl or thienopyridinyl, Y is other than $NR^{12}$;

iv) when ring B is pyrimidinyl or substituted pyrimidinyl, ring A is benzimidazolyl, $R^5$ is other than phenyl or substituted phenyl.

In a second embodiment, the present invention provides compounds of Formula (Ia):

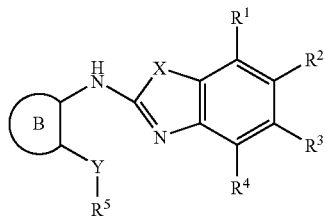

(Ia)

or a stereoisomer or pharmaceutically acceptable salts, solvates, or prodrugs thereof wherein:
ring B is phenyl substituted with 0-4 $R^7$, or a 5- to 6-membered heteroaryl comprising: carbon atoms and 1-3 ring heteroatoms selected from O, N, $NR^6$, and $S(O)_p$, and said heteroaryl is substituted with 0-3 $R^7$;
X is $NR^{11}$, O, or S;
$R^1$, $R^2$, $R^3$, and $R^4$ are, independently at each occurrence, H, F, Cl, Br, I, $OCF_3$, $CF_3$, $OR^c$, $SR^c$, CN, $NO_2$, —$NR^8R^9$, —$C(O)R^c$, —$C(O)OR^c$, —$C(O)NR^8R^9$, —$NR^{10}(O)R^d$, —$S(O)_pNR^8R^9$, —$S(O)R^d$, —$S(O)_2R^d$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, O, and $S(O)_p$, and substituted with 0-3 $R^b$;
alternatively, $R^1+R^2$, $R^2+R^3$, or $R^3+R^4$, combine with the carbon atoms to which they are attached, form a 5- or 6-membered carbocycle or heterocycle comprising: carbon atoms and 0-3 additional heteroatoms selected from N, NH, O, and $S(O)_p$, and substituted with 0-2 $R^b$;
Y is $NR^{12}$, O, or S;
$R^5$ is a $C_{3-10}$ carbocycle substituted with 0-3 $R^b$, or a 5- to 10-membered heterocycle comprising: carbon atoms and 1-4 heteroatoms selected from N, O, and $S(O)_p$, and substituted with 0-3 $R^b$;
$R^6$ is H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, ($C_{1-6}$ alkyl)C(O)—, ($C_{3-6}$ cycloalkyl)$C_{1-3}$ alkyl-C(O)—, ($C_{3-6}$ cycloalkyl)C(O)—, phenyl-C(O)—, benzyl-C(O)—, benzyl-S(O)$_2$—, ($C_{1-6}$ alkyl)NHC(O)—, ($C_{1-6}$ alkyl)$_2$NC(O)—, phenyl-NHC(O)—, benzyl-NHC(O)—, (phenyl)($C_{1-6}$ alkyl)NC(O)—, (benzyl)($C_{1-6}$ alkyl)NC(O)—, ($C_{1-6}$ alkyl)-S(O)$_2$—, phenyl-S(O)$_2$—, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, O, and $S(O)_p$, and substituted with 0-3 $R^b$;
$R^7$ is H, F, Cl, Br, I, $OCF_3$, $CF_3$, $OR^c$, $SR^c$, CN, $NO_2$, —$NR^8R^9$, —$C(O)R^c$, —$C(O)OR^c$, —$C(O)NR^8R^9$, —$NR^{10}C(O)R^d$, —$S(O)_pNR^8R^9$, —$S(O)R^d$, —$S(O)_2R^d$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, O, and $S(O)_p$, and substituted with 0-3 $R^b$;
alternatively, two $R^7$s on the two adjacent carbon atoms are combined to form a 5- to 7-membered carbocyclic or heterocyclic ring comprising: carbon atoms and 0-3 ring heteroatoms selected from O, N, $NR^{6a}$, and $S(O)_p$, and said carbocyclic or heterocyclic ring is substituted with 0-3 $R^{7a}$;
alternatively, $R^6$ may combine with the $R^7$ on the adjacent carbon atom to form a 5- to 7-membered carbocyclic or heterocyclic ring comprising: carbon atoms and 0-3 ring heteroatoms selected from O, N, $NR^{6a}$, and $S(O)_p$, and said carbocyclic or heterocyclic ring is substituted with 0-3 $R^{7a}$;

$R^{6a}$ is H, $C_{1-4}$ alkyl, $(C_{1-4}$ alkyl)C(O)—, phenyl-C(O)—, benzyl-C(O)—, benzyl-S(O)$_2$—, $(C_{1-4}$ alkyl)NHC(O)—, $(C_{1-4}$ alkyl)$_2$NC(O)—, phenyl-NHC(O)—, benzyl-NHC(O)—, $(C_{1-4}$ alkyl)-S(O)$_2$—, phenyl-S(O)$_2$—, phenyl substituted with 0-3 $R^b$, or benzyl substituted with 0-3 $R^b$;

$R^{7a}$ is H, F, Cl, Br, I, $OCF_3$, $CF_3$, $OR^c$, $SR^c$, CN, $NO_2$, —$NR^8R^9$, —C(O)$R^c$, —C(O)O$R^c$, —C(O)$NR^8R^9$, —$NR^{10}C(O)R^d$, —$S(O)_pNR^8R^9$, —$S(O)R^d$, —$S(O)_2R^d$, $C_{1-4}$ alkyl, phenyl substituted with 0-3 $R^b$, or benzyl substituted with 0-3 $R^b$;

$R^8$ is, independently at each occurrence, H, $C_{1-6}$ alkyl, $(C_{1-6}$ alkyl)C(O)—, —$(CH_2)_n$-phenyl, $(C_{1-4}$ alkyl)OC(O)—, $(C_{6-10}$ aryl)-$CH_2$—OC(O)—, $(C_{6-10}$ aryl)-$CH_2$—C(O)—, $(C_{1-4}$ alkyl)-C(O)O—$(C_{1-4}$ alkyl)-OC(O)—, $(C_{6-10}$ aryl)-C(O)O—$(C_{1-4}$ alkyl)-OC(O)—, $(C_{1-6}$ alkyl)-NHC(O)—, $(C_{6-10}$ aryl)-NHC(O)—, (5- to 10-membered heteroaryl)-NHC(O)—, (5- to 10-membered heteroaryl)-$CH_2$—OC(O)—, (5- to 10-membered heteroaryl)-C(O)—, $(C_{6-10}$ aryl)-$(C_{1-4}$ alkyl)-C(O)—, $(C_{1-6}$ alkyl)-$S(O)_2$—, $(C_{6-10}$ aryl)-$S(O)_2$—, (5- to 10-membered heteroaryl)-$S(O)_2$—, or $(C_{6-10}$ aryl)-$(C_{1-4}$ alkyl)-$S(O)_2$—, wherein said phenyl, aryl and heteroaryl are substituted with 0-2 $R^g$;

$R^9$ is, independently at each occurrence, H, $C_{1-6}$ alkyl, or —$(CH_2)_n$-phenyl;

alternatively, $R^8$ and $R^9$, when attached to the same nitrogen, combine to form a 5- to 10-membered heterocyclic ring comprising: carbon atoms and 0-2 additional heteroatoms selected from N, O, and $S(O)_p$;

$R^{10}$ is, independently at each occurrence, H, $C_{1-6}$ alkyl substituted with 0-2 $R^{10a}$, $C_{2-6}$ alkenyl substituted with 0-2 $R^{10a}$, $C_{2-6}$ alkynyl substituted with 0-2 $R^{10a}$, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, O, and $S(O)_p$, and substituted with 0-3 $R^e$;

$R^{10a}$ is, independently at each occurrence, H, $C_{1-4}$ alkyl, $OR^c$, Cl, F, Br, I, =O, $CF_3$, CN, $NO_2$, —C(O)$R^c$, —C(O)O$R^c$, —C(O)$NR^8R^9$, or $S(O)_pR^d$;

$R^{11}$ is H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, $(C_{1-6}$ alkyl)C(O)—, $(C_{3-6}$ cycloalkyl)$C_{1-3}$ alkyl-C(O)—, $(C_{3-6}$ cycloalkyl)C(O)—, phenyl-C(O)—, benzyl-C(O)—, benzyl-S(O)$_2$—, $(C_{1-6}$ alkyl)NHC(O)—, $(C_{1-6}$ alkyl)$_2$NC(O)—, phenyl-NHC(O)—, benzyl-NHC(O)—, (phenyl)$(C_{1-6}$ alkyl)NC(O)—, (benzyl)$(C_{1-6}$ alkyl)NC(O)—, $(C_{1-6}$ alkyl)-S(O)$_2$—, phenyl-S(O)$_2$—, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, O, and $S(O)_p$, and substituted with 0-3 $R^b$;

$R^{12}$ is H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, $(C_{1-6}$ alkyl)C(O)—, $(C_{3-6}$ cycloalkyl)$C_{1-3}$ alkyl-C(O)—, $(C_{3-6}$ cycloalkyl)C(O)—, phenyl-C(O)—, benzyl-C(O)—, benzyl-S(O)$_2$—, $(C_{1-6}$ alkyl)NHC(O)—, $(C_{1-6}$ alkyl)$_2$NC(O)—, phenyl-NHC(O)—, benzyl-NHC(O)—, (phenyl)$(C_{1-6}$ alkyl)NC(O)—, (benzyl)$(C_{1-6}$ alkyl)NC(O)—, $(C_{1-6}$ alkyl)-S(O)$_2$—, phenyl-S(O)$_2$—, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, O, and $S(O)_p$, and substituted with 0-3 $R^b$;

$R^a$ is, independently at each occurrence, H, F, $OCF_3$, $CF_3$, $OR^c$, $SR^c$, CN, —$NR^8R^9$, —C(O)$NR^8R^9$, —$NR^{10}C(O)R^b$, —$S(O)_pNR^8R^9$, —$S(O)R^d$, or —$S(O)_2R^d$;

$R^b$ is, independently at each occurrence, H, F, Cl, Br, I, $OR^c$, $SR^c$, CN, $NO_2$, $CF_3$, —$SO_2R^d$, —$NR^8R^9$, $C_{1-6}$ alkyl, $C_{2-6}$ alkenyl, $C_{2-6}$ alkynyl, $C_{3-6}$ cycloalkyl, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-C(O)—, $C_1$-$C_4$ alkyl-O—C(O)—, or $C_1$-$C_4$ alkyl-C(O)NH—;

$R^c$ is, independently at each occurrence, H, $C_{1-4}$ alkyl, —$(CH_2)_r$—$C_{6-10}$ aryl substituted with 0-2 $R^e$, or —$(CH_2)_r$-5- to 10-membered heterocycle containing from 1-4 heteroatoms selected from N, O, and $S(O)_p$ and substituted with 0-2 $R^e$;

$R^d$ is, independently at each occurrence, $CF_3$, OH, $C_{1-4}$ alkoxy, $C_{1-6}$ alkyl, —$(CH_2)_r$—$C_{3-10}$ carbocycle substituted with 0-2 $R^e$, or —$(CH_2)_r$-5- to 10-membered heterocycle comprising: carbon atoms and 1-4 heteroatoms selected from N, O, and $S(O)_p$ and substituted with 0-2 $R^e$;

$R^e$ is, independently at each occurrence, H, =O, $OR^g$, F, Cl, Br, I, CN, $NO_2$, —$NR^8R^9$, —C(O)$R^f$, —C(O)O$R^f$, —$NR^8C(O)R^f$, —C(O)$NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

$R^f$ is, independently at each occurrence, H, $C_{1-6}$ alkyl, or —$(CH_2)_n$-phenyl;

$R^g$ is, independently at each occurrence, H, =O, $OR^f$, Cl, Br, I, CN, $NO_2$, —$NR^9R^9$, —C(O)$R^h$, —C(O)O$R^h$, $NR^9C(O)R^h$, —C(O)$NR^9R^9$, —$SO_2NR^9R^9$, —$NR^9SO_2NR^9R^9$, —$NR^9SO_2$—$C_{1-4}$ alkyl, —$NR^9SO_2CF_3$, —$NR^9SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

$R^h$ is, independently at each occurrence, H, $C_{1-6}$ alkyl, or —$(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4;

provided that:

i) when ring B is

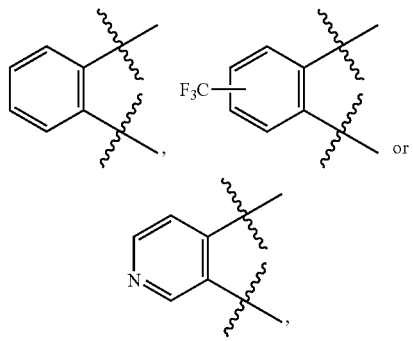

and ring A is

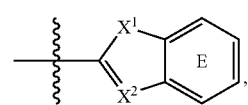

ring E is phenyl substituted with $OR^c$ or $SR^c$, then $R^c$ is other than aryl or heteroaryl;

ii) when ring B is

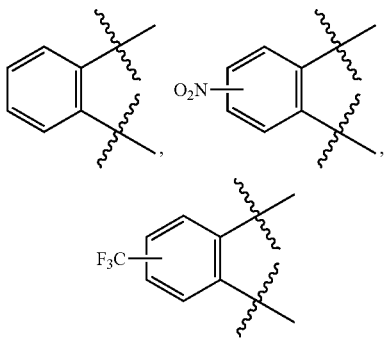

or

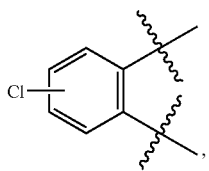

then $R^5$ is other than pyrrolidinyl, substituted pyrrolidinyl, phenyl, benzoimidazolyl or N-methyl substituted benzoimidazolyl;

iii) when ring A is thienopyrimidinyl or thienopyridinyl, Y is other than $NR^{12}$; or iv) when ring B is pyrimidinyl or substituted pyrimidinyl, ring A is benzimidazolyl, $R^5$ is other than phenyl or substituted phenyl.

In a third embodiment, the present invention provides compounds of Formula (Ia), or a stereoisomer or pharmaceutically acceptable salts, solvates, or prodrugs thereof, within the scope of the second embodiment wherein:

ring B is phenyl substituted with 0-3 $R^7$, or a 5- to 6-membered heteroaryl comprising: carbon atoms and 1-3 ring heteroatoms selected from O, N, $NR^6$, and $S(O)_p$; wherein the heteroaryl is substituted with 0-2 $R^7$.

In a fourth embodiment, the present invention provides compounds of Formula (Ia):

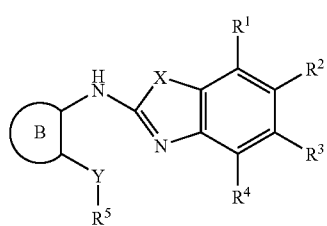

(Ia)

or a stereoisomer or pharmaceutically acceptable salts, solvates, or prodrugs thereof, within the scope of the first embodiment wherein:

ring B is phenyl substituted with 0-3 $R^7$, or a 5- to 6-membered heteroaryl comprising: carbon atoms and 1-3 ring heteroatoms selected from O, N, $NR^6$, and $S(O)_p$, and said heteroaryl is substituted with 0-2 $R^7$.

$R^1$, $R^2$, $R^3$, and $R^4$ are, independently at each occurrence, H, F, Cl, Br, I, $OCF_3$, $CF_3$, $—CF_2CF_3$, $(CR^fR^f)_r—OR^c$, $SR^c$, CN, $NO_2$, $—(CR^fR^f)_r—NR^8R^9$, $—(CR^fR^f)_r—C(O)R^c$, $—(CR^fR^f)_r—C(O)OR^c$, $—(CR^fR^f)_r—C(O)NR^8R^9$, $—C(O)NR^8(CR^fR^f)_rNR^8R^9$, $—NR^{10}(CR^fR^f)_nC(O)R^d$, $NR^{10}CO(CR^fR^f)_nOR^c$, $—S(O)_pNR^8R^9$, $—NR^{10}S(O)_pR^d$, $—S(O)R^d$, $—S(O)_2R^d$, $—N(C_{1-4}alkyl)_3{}^+Cl^-$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, $—(CR^fR^f)_r—C_{3-10}$ carbocycle substituted with 0-3 $R^b$, or $—(CR^fR^f)_r$-5- to 12-membered heterocycle comprising: carbon atoms and 1-4 heteroatoms selected from N, O, and $S(O)_p$, and substituted with 0-3 $R^b$; and alternatively, $R^1+R^2$, $R^2+R^3$, or $R^3+R^4$, combine with the carbon atoms to which they are attached, form a 5- or 6-membered carbocycle or heterocycle comprising: carbon atoms and 0-3 additional heteroatoms selected from N, NH, O, and $S(O)_p$, and substituted with 0-2 $R^b$.

In a fifth embodiment, the present invention provides compounds of Formula (Ia), or a stereoisomer or pharmaceutically acceptable salts, solvates, or prodrugs thereof, within the scope of the fourth embodiment wherein:

one of the $R^1$, $R^2$, $R^3$ and $R^4$ groups is $—(CR^fR^f)_r—OR^c$, $—(CR^f—R^f)_r—NR^8R^9$, $—(CR^fR^f)_r—C(O)OR^c$, $—(CR^fR^f)_r—C(O)NR^8R^9$, $—C(O)NR^8(CR^fR^f)_rNR^8R^9$, $—NR^{10}(CR^{ff})_nC(O)R^d$, or $—NR^{10}CO(CR^fR^f)_nOR^c$;

remaining of the $R^1$, $R^2$, $R^3$, and $R^4$ groups are, independently at each occurrence, H, F, Cl, Br, I, $OCF_3$, $CF_3$, $—CF_2CF_3$, $—(CR^fR^f)_r—OR^c$, $SR^c$, CN, $NO_2$, $—(CR^fR^f)_r—NR^8R^9$, $—(CR^fR^f)_r—C(O)R^c$, $—(CR^fR^f)_r—C(O)OR^c$, $—S(O)_pNR^8R^9$, $—NR^{10}S(O)_pR^d$, $—S(O)R^d$, $—S(O)_2R^d$, $—N(C_{1-4}alkyl)_3{}^+Cl^-$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, $—(CR^fR^f)_r—C_{3-10}$ carbocycle substituted with 0-3 $R^b$, or $—(CR^fR^f)_r$-5- to 12-membered heterocycle comprising: carbon atoms and 1-4 heteroatoms selected from N, O, and $S(O)_p$, and substituted with 0-3 $R^b$; and alternatively, $R^1+R^2$, $R^2+R^3$, or $R^3+R^4$, combine with the carbon atoms to which they are attached, form a 5- or 6-membered carbocycle or heterocycle comprising: carbon atoms and 0-3 additional heteroatoms selected from N, NH, O, and $S(O)_p$, and substituted with 0-2 $R^b$.

In a sixth embodiment, the present invention provides compounds of Formula (Ia), or a stereoisomer or pharmaceutically acceptable salts, solvates, or prodrugs thereof, within the scope of the fifth embodiment wherein:

one of the $R^1$, $R^2$, $R^3$ and $R^4$ groups is NHBn, —NH(4-OMe-Bn), —NH(4-$CF_3$-Bn), —NH(4-$OCF_3$-Bn), $CO_2Et$, —$CO_2$-neopentyl, —$CO_2CH_2CH$=$CH_2$, —CH(Me)$OCH_2C(Me)_2CH_2NMe_2$, —CH(Me)OBn, —CH(Me)O(4-i-Pr-Bn), —CH(Me)O(3-$CF_3$-Bn), —CH(Me)O(4-$CF_3$-Bn), —CH(Me)O(4-OPh-Bn), —CH(Me)O(3,5-diCl-Bn), —CH(Me)$OCH_2$(1-Bn-piperidin-4-yl), —$CH_2$NHBn, —$CH_2$NH(4-$CF_3$-Bn), —$CH_2$N(Me)Bn, —CH(Me)NH$CH_2$-pyridin-2-yl, —CH(Me)NH$CH_2$-pyridin-4-yl, —CH(Me)NH$CH_2$(6-Cl-pyridin-3-yl), —CH(Me)N(Me)(i-Bu), —CH(Me)N(Me)Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me)(3-$CF_3$-Bn), —CH(Me)N(Me)(4-$CF_3$-Bn), —CH(Me)N(Me)(3,4-diCl-Bn), —CH(Me)N(Me)$CH_2CH_2$Ph, —CH(Me)N(Me)$CH_2$-pyridin-2-yl, —CH(Me)N(Me)$CH_2$-pyridin-3-yl, —CH(Me)N(Me)$CH_2$-pyridin-4-yl, —CH(Me)N(Me)$CH_2$-furan-2-yl, —CH(Me)N(Me)$CH_2$-thien-2-yl, —CH(Me)N(Me)$CH_2$-(5-Me-thien-2-yl), —CH(Me)N(Me)$CH_2$-(5-Cl-thien-2-yl), —CH(Me)N(Et)Bn, —CH(Me)N(Et)(4-Me-Bn), —CH(Me)N(Et)(2-Cl-Bn), —CH(Me)N(Bn)$CH_2$CN, —CH(Me)N(Bn)$CH_2CH_2$OH, —CH(Me)N(Bn)$CH_2CO_2$Me, —CH(Me)N(Bn)$CH_2CONMe_2$, —CH(Me)N(Bn)$CH_2$CON(Me)(Bn), —CH (Me)-isoindolin-2-yl, —CH(Me)-(1,2,3,4-tetrahydroiso-quinolin-2-yl), —CH(Me)(4-Bn-piperazin-1-yl), —CONH-neopentyl, —CONHBn, —CONH(4-CF$_3$-Bn), —CONH(4-NO$_2$-phenethyl), —CONHCH$_2$CH$_2$NHPh, —NHCOCH$_2$OBn, —NHCOCH$_2$O-(4-t-Bu-Ph), —NHCO(4-Ph-Ph), —NHCO(5-(3,5-diCl-OPh)-2-furanyl), or —NHCOC(Me)$_2$O(-4-Cl-Ph).

In a seventh embodiment, the present invention provides compounds of Formula (Ia), or a stereoisomer or pharmaceutically acceptable salts, solvates, or prodrugs thereof, within the scope of the fourth embodiment wherein:

ring B is 6-membered heteroaryl comprising: carbon atoms and 1-3 ring heteroatoms selected from O, N, NR$^6$, and S(O)$_p$, and said heteroaryl is substituted with 0-2 R$^7$;

R$^8$ is, independently at each occurrence, H, C$_{1-6}$ alkyl substituted with 0-2 R$^j$, —C(O)R$^k$, —C(O)OR$^k$, —C(O)NR$^i$R$^i$, —S(O)$_2$R$^k$, —(CR$^f$R$^f$)$_r$—C$_{3-10}$ carbocycle substituted with 0-2 R$^j$, or —(CR$^f$R$^f$)$_r$-5-10 membered heterocycle comprising: carbon atoms and 1-4 heteroatoms selected from N, O, and S(O)$_p$ and substituted with 0-2 R$^j$;

R$^9$ is, independently at each occurrence, H, C$_{1-4}$ alkyl, or —(CH$_2$)$_n$-phenyl;

alternatively, R$^8$ and R$^9$, when attached to the same nitrogen, combine to form a 5- to 10-membered heterocyclic ring comprising: carbon atoms and 0-2 additional heteroatoms selected from N, NR$^i$, O, and S(O)$_p$;

R$^{10}$ is, independently at each occurrence, H, C$_{1-6}$ alkyl substituted with 0-2 R$^{10a}$, C$_{2-6}$ alkenyl substituted with 0-2 R$^{10a}$, C$_{2-6}$ alkynyl substituted with 0-2 R$^{10a}$, —(CH$_2$)$_r$-phenyl substituted with 0-3 R$^e$, or —(CH$_2$)$_r$-5-10 membered heterocycle comprising: carbon atoms and 1-4 heteroatoms selected from N, O, and S(O)$_p$, and substituted with 0-3 R$^e$;

R$^{11}$ is H, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —C(O)R$^c$, —C(O)NR$^8$R$^9$, —S(O)$_2$R$^k$, —(CH$_2$)$_r$-phenyl substituted with 0-3 R$^b$, or —(CH$_2$)$_r$-5-10 membered heterocycle comprising: carbon atoms and 1-4 heteroatoms selected from N, O, and S(O)$_p$, and substituted with 0-3 R$^b$;

R$^{12}$ is H, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —C(O)R$^c$, —C(O)NR$^8$R$^9$, —S(O)$_2$R$^k$, —(CH$_2$)$_r$-phenyl substituted with 0-3 R$^b$, or —(CH$_2$)$_r$-5-10 membered heterocycle comprising: carbon atoms and 1-4 heteroatoms selected from N, O, and S(O)$_p$, and substituted with 0-3 R$^b$; and R$^{13}$ is H, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —C(O)R$^c$, —C(O)NR$^8$R$^9$, —S(O)$_2$R$^k$, —(CH$_2$)$_r$-phenyl substituted with 0-3 R$^b$, or —(CH$_2$)$_r$-5- to 10-membered heterocycle comprising: carbon atoms and 1-4 heteroatoms selected from N, O, and S(O)$_p$, and substituted with 0-3 R$^b$.

In an eighth embodiment, the present invention includes compounds of Formula (Ia), or a stereoisomer or pharmaceutically acceptable salts, solvates, or prodrugs thereof, within the scope of the fifth embodiment wherein:

ring B is substituted with 0-2 R$^7$ and selected from pyridinyl, furanyl, thienyl, pyrrolyl, pyrazolyl, isoxazolyl, oxazolyl, and thiazolyl.

In a ninth embodiment, the present invention includes compounds of Formula (Ia), or a stereoisomer or pharmaceutically acceptable salts, solvates, or prodrugs thereof, within the scope of the fifth embodiment wherein:

ring B is substituted with 0-2 R$^7$ and selected from pyridinyl and thienyl.

In a tenth embodiment, the present invention includes compounds of Formula (Ia), or a stereoisomer or pharmaceutically acceptable salts, solvates, or prodrugs thereof, within the scope of the sixth embodiment wherein:

Y is O or S;

R$^5$ is phenyl with 0-3 R$^b$, or a 5-6 membered heterocycle substituted with 0-3 R$^b$ and selected from pyridinyl, furanyl, thienyl, pyrrolyl, pyrazolyl, pyrazinyl, imidazolyl, isoxazolyl, oxazolyl, thiazolyl, and triazinyl;

alternatively, R$^5$ is

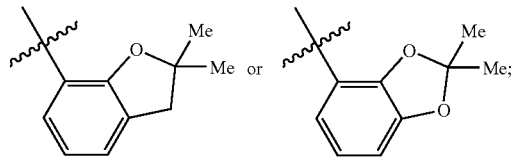

R$^{10}$ is, independently at each occurrence, H, C$_{1-4}$ alkyl, phenyl, or benzyl; and R$^{11}$ is H, C$_{1-4}$ alkyl, C$_{2-4}$ alkenyl, C$_{2-4}$ alkynyl, (C$_{1-4}$ allyl) C(O)—, benzyl-C(O)—, benzyl-S(O)$_2$—, (C$_{1-4}$ alkyl)-S(O)$_2$—, or benzyl.

In an eleventh embodiment, the present invention includes the compounds of Formula (Ib) or (Ib'):

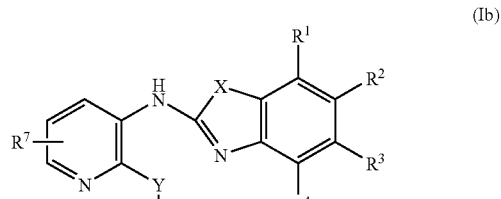

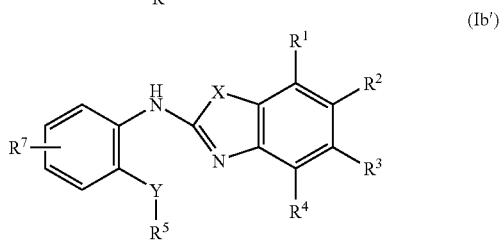

or a stereoisomer or pharmaceutically acceptable salts, solvates, or prodrugs thereof, wherein:

X is NR$^{11}$, O or S;

R$^1$, R$^2$, R$^3$, and R$^4$ are, independently at each occurrence, H, F, Cl, Br, I, CF$_3$, OCF$_3$, OR$^c$, —CH$_2$OR$^c$, —CH$_2$CH$_2$OR$^c$, —CH(C$_{1-4}$ alkyl)OR$^c$, SR$^c$, CN, NO$_2$, —NR$^8$R$^9$, —CH$_2$NR$^8$R$^9$, —CH$_2$CH$_2$NR$^8$R$^9$, —CH(C$_{1-4}$ alkyl)NR$^8$R$^9$, —C(O)R$^c$, —C(O)OR$^c$, —C(O)NR$^8$R$^9$, —C(O)NR$^8$(CR$^f$R$^f$)$_t$NR$^8$R$^9$, —NR$^{10}$(CR$^f$R$^f$)$_n$C(O)R$^d$, —NR$^{10}$CO(CR$^f$R$^f$)$_n$OR$^c$, —S(O)$_p$NR$^8$R$^9$, —NR$^{10}$S(O)$_p$R$^d$, —S(O)R$^d$, —S(O)$_2$R$^d$, —N(C$_{1-4}$ alkyl)$_3$$^+$Cl$^-$, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —(CR$^f$R$^f$)$_r$—C$_{3-7}$ cycloalkyl substituted with 0-3 R$^b$, —(CR$^f$R$^f$)$_r$-phenyl substituted with 0-3 R$^b$, or —(CR$^f$R$^f$)$_r$-5-10 membered heterocycle comprising: carbon atoms and 1-4 heteroatoms selected from N, O, and S(O)$_p$, and substituted with 0-3 R$^b$;

alternatively, R$^1$+R$^2$, R$^2$+R$^3$, or R$^3$+R$^4$, combine with the carbon atoms to which they are attached, form a 5- or 6-membered carbocycle or heterocycle comprising: carbon atoms and 0-3 additional heteroatoms selected from N, NH, O, and S(O)$_p$, and substituted with 0-2 R$^b$;

Y is $NR^{12}$, O, or S;

$R^5$ is phenyl with 0-3 $R^b$, or a 5-6 membered heterocycle substituted with 0-3 $R^b$ and selected from pyridinyl, furanyl, thienyl, pyrrolyl, pyrazolyl, pyrazinyl, imidazolyl, isoxazolyl, oxazolyl, thiazolyl, and triazinyl;

alternatively, $R^5$ is

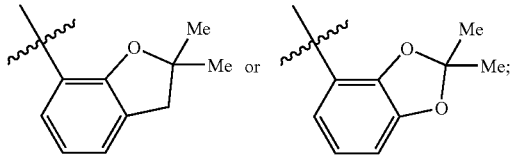

$R^7$ is H, F, Cl, Br, $OCF_3$, $CF_3$, $OR^c$, $SR^c$, CN, $NO_2$, $-NR^8R^9$, $-C(O)R^c$, $-C(O)OR^c$, $-C(O)NR^8R^9$, $-NR^{10}C(O)R^d$, $-S(O)_pNR^8R^9$, $-S(O)R^d$, $-S(O)_2R^d$, $C_{1-4}$ alkyl substituted with 0-1 $R^a$, $C_{2-4}$ alkenyl substituted with 0-1 $R^a$, $C_{2-4}$ alkynyl substituted with 0-1 $R^a$, $-(CH_2)_r$-$C_{3-7}$ cycloalkyl substituted with 0-3 $R^b$, $-(CH_2)_r$-phenyl substituted with 0-3 $R^b$, or $-(CH_2)_r$-5-10 membered heterocycle comprising: carbon atoms and 1-4 heteroatoms selected from N, O, and $S(O)_p$, and substituted with 0-3 $R^b$;

$R^8$ is, independently at each occurrence, H, $C_{1-6}$ alkyl substituted with 0-2 $R^j$, $-C(O)R^k$, $-C(O)OR^k$, $-C(O)NR^iR^i$, $-S(O)_2R^k$, $-(CR^iR^f)_r$-phenyl substituted with 0-3 $R^j$, or $-(CR^iR^f)_r$-5-10 membered heterocycle comprising: carbon atoms and 1-4 heteroatoms selected from N, O, and $S(O)_p$ and substituted with 0-3 $R^j$;

$R^9$ is, independently at each occurrence, H, $C_{1-6}$ alkyl, $-(CR^iR^f)_r$-phenyl substituted with 0-3 $R^j$, or $-(CR^iR^f)_r$-5-10 membered heterocycle comprising: carbon atoms and 1-4 heteroatoms selected from N, O, and $S(O)_p$ and substituted with 0-3 $R^j$;

alternatively, $R^8$ and $R^9$, when attached to the same nitrogen, combine to form a 5- to 10-membered heterocyclic ring comprising: carbon atoms and 0-2 additional heteroatoms selected from N, $NR^i$, O, and $S(O)_p$;

$R^{10}$ is, independently at each occurrence, H, $C_{1-4}$ alkyl, phenyl, or benzyl;

$R^{11}$ is H, $C_{1-4}$ alkyl substituted with 0-1 $R^a$, $C_{2-4}$ alkenyl substituted with 0-1 $R^a$, $C_{2-4}$ alkynyl substituted with 0-1 $R^a$, ($C_{1-4}$ alkyl)C(O)—, phenyl-C(O)—, benzyl-C(O)—, benzyl-S(O)$_2$—, ($C_{1-4}$ alkyl)-S(O)$_2$—, phenyl-S(O)$_2$—, phenyl, or benzyl;

$R^{12}$ is H, $C_{1-4}$ alkyl substituted with 0-1 $R^a$, $C_{2-4}$ alkenyl substituted with 0-1 $R^a$, $C_{2-4}$ alkynyl substituted with 0-1 $R^a$, ($C_{1-4}$ alkyl)C(O)—, phenyl-C(O)—, benzyl-C(O)—, benzyl-S(O)$_2$—, ($C_{1-4}$ alkyl)-S(O)$_2$—, phenyl-S(O)$_2$—, phenyl, or benzyl;

$R^a$ is, independently at each occurrence, H, F, $OCF_3$, $CF_3$, $OR^c$, $SR^c$, CN, $-NR^8R^9$, $-C(O)R^c$, $-C(O)OR^c$, $-C(O)NR^8R^9$, $-NR^{10}C(O)R^b$, $-S(O)_pNR^8R^9$, $-S(O)R^d$, or $-S(O)_2R^d$;

$R^b$ is, independently at each occurrence, H, F, Cl, Br, I, $OR^c$, $SR^c$, CN, $NO_2$, $CF_3$, $-C(O)OR^c$, $-SO_2R^d$, $-NR^8R^9$, $C_{1-6}$ alkyl, $C_{2-6}$ alkenyl, $C_{2-6}$ alkynyl, $C_{3-6}$ cycloalkyl, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-C(O)—, $C_1$-$C_4$ alkyl-O—C(O)—, $C_1$-$C_4$ alkyl-C(O)NH—, or $-(CH_2)_n$-phenyl substituted with $R^j$;

$R^c$ is, independently at each occurrence, H, $C_{1-6}$ alkyl substituted with 0-2 $R^j$, $C_{2-6}$ alkenyl substituted with 0-2 $R^j$, $C_{2-6}$ alkynyl substituted with 0-2 $R^j$, $-(CH_2)_r$-$C_{6-10}$ aryl substituted with 0-2 $R^e$, or $-(CH_2)_r$-5-10 membered heterocycle comprising: carbon atoms and 1-4 heteroatoms selected from N, O, and $S(O)_p$ and substituted with 0-2 $R^e$;

$R^d$ is, independently at each occurrence, $CF_3$, OH, $C_{1-4}$ alkoxy, $C_{1-6}$ alkyl substituted with 0-2 $R^j$, $-(CH_2)_r$-$C_{3-10}$ carbocycle substituted with 0-2 $R^e$, or $-(CH_2)_r$-5-10 membered heterocycle comprising: carbon atoms and 1-4 heteroatoms selected from N, O, and $S(O)_p$ and substituted with 0-2 $R^e$;

$R^e$ is, independently at each occurrence, H, =O, $OR^g$, F, Cl, Br, I, CN, $NO_2$, $-NR^8R^9$, $-C(O)R^f$, $-C(O)OR^f$, $-NR^8C(O)R^f$, $-C(O)NR^8R^9$, $-SO_2NR^8R^9$, $-NR^8SO_2NR^8R^9$, $-NR^8SO_2$-$C_{1-4}$ alkyl, $-NR^8SO_2CF_3$, $-NR^8SO_2$-phenyl, $-S(O)_2CF_3$, $-S(O)_p$-$C_{1-4}$ alkyl, $-S(O)_p$-phenyl, $-(CF_2)_rCF_3$, $C_{1-6}$ alkyl, $C_{2-6}$ alkenyl, $C_{2-6}$ alkynyl, or $-(CH_2)_n$-phenyl;

$R^f$ is, independently at each occurrence, H, $C_{1-6}$ alkyl, or $-(CH_2)_n$-phenyl;

$R^g$ is, independently at each occurrence, H, =O, $OR^f$, F, Cl, Br, I, CN, $NO_2$, $-NR^9R^9$, $-C(O)R^h$, $-C(O)OR^h$, $-NR^9C(O)R^h$, $-C(O)NR^9R^9$, $-SO_2NR^9R^9$, $-NR^9SO_2NR^9R^9$, $-NR^9SO_2$-$C_{1-4}$ alkyl, $-NR^9SO_2CF_3$, $-NR^9SO_2$-phenyl, $-S(O)_2CF_3$, $-S(O)_p$-$C_{1-4}$ alkyl, $-S(O)_p$-phenyl, $-(CF_2)_rCF_3$, $C_{1-6}$ alkyl, $C_{2-6}$ alkenyl, $C_{2-6}$ alkynyl, or $-(CH_2)_n$-phenyl;

$R^h$ is, independently at each occurrence, H, $C_{1-6}$ alkyl, or $-(CH_2)_n$-phenyl;

$R^i$ is, independently at each occurrence, H, $C_{1-6}$ alkyl, or $-(CH_2)_n$-phenyl substituted with 0-2 $R^j$;

$R^j$ is, independently at each occurrence, H, =O, $OR^f$, F, Cl, Br, I, CN, $NO_2$, $-NR^fR^h$, $-C(O)R^h$, $-C(O)OR^h$, $-NR^fC(O)R^h$, $-C(O)NR^fR^h$, $-SO_2NR^fR^h$, $-NR^fSO_2$-$C_{1-4}$ alkyl, $-NR^fSO_2CF_3$, $-NR^fSO_2$-phenyl, $-S(O)_2CF_3$, $-S(O)_p$-$C_{1-4}$ alkyl, $-S(O)_p$-phenyl, $-(CF_2)_rCF_3$, $C_{1-6}$ alkyl, $C_{2-6}$ alkenyl, $C_{2-6}$ alkynyl, or $-(CH_2)_n$-phenyl;

$R^k$ is, independently at each occurrence, $C_{1-6}$ alkyl, $-(CH_2)_r$-phenyl substituted with 0-2 $R^j$, or $-(CH_2)_r$-5-10 membered heterocycle comprising: carbon atoms and 1-4 heteroatoms selected from N, O, and $S(O)_p$ and substituted with 0-2 $R^j$;

n, at each occurrence, is selected from 0, 1, 2, 3, and 4;
p, at each occurrence, is selected from 0, 1, and 2;
r, at each occurrence, is selected from 0, 1, 2, 3, and 4; and
t, at each occurrence, is selected from 1, 2, 3 and 4;
provided that:
i) when ring B is

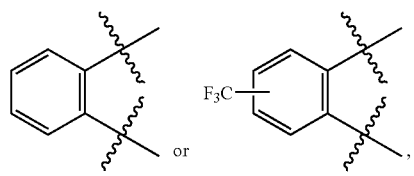

and ring E is phenyl substituted with $OR^c$ or $SR^c$, then $R^c$ is other than aryl or heteroaryl; or ii) when ring B is

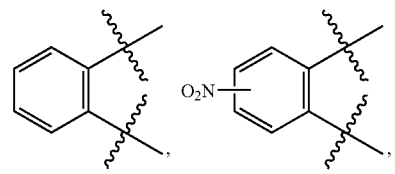

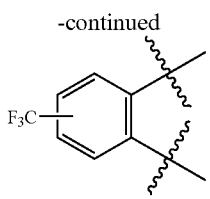

or

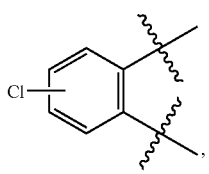

then $R^5$ is other than phenyl.

In a twelfth embodiment, the present invention includes the compounds of Formula (Ib):

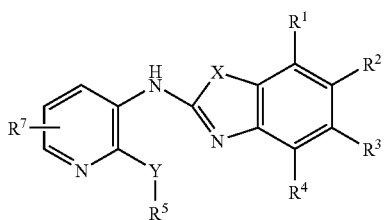

or a stereoisomer or pharmaceutically acceptable salts, solvates, or prodrugs thereof, within the scope of the eleventh embodiment.

In a thirteenth embodiment, the present invention includes the compounds of Formula (Ic):

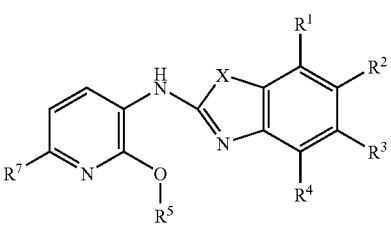

or a stereoisomer or pharmaceutically acceptable salts, solvates, or prodrugs thereof, wherein:

X is NH, $NC_{1-4}$ alkyl, O or S;

$R^1$, $R^2$, $R^3$, and $R^4$ are, independently at each occurrence, H, F, Cl, Br, $CF_3$, CN, OH, $OC_{1-6}$ alkyl, phenoxy, benzyloxy, $SC_{1-4}$ alkyl, $OCF_3$, $NH_2$, $NHC_{1-4}$ alkyl, $N(C_{1-4}$ alkyl$)_2$, $NO_2$, NHBn, —$CH_2OC_{1-4}$ alkyl, —$CH(C_{1-4}$ alkyl$)OC_{1-4}$ alkyl, —$CH(C_{1-4}$ alkyl$)OCH_2C(Me)_2CH_2N(C_{1-4}$ alkyl$)_2$, —CH($C_{1-4}$ alkyl)O-benzyl, —$CH(C_{1-4}$ alkyl$)OCH_2$(1-Bn-piperidin-4-yl), —$CH_2$NH-benzyl, —$CH_2N(C_{1-4}$ alkyl$)_2$, —$CH_2N(C_{1-4}$ alkyl)-benzyl, —$CH(C_{1-4}$ alkyl$)$NH-benzyl, —$CH_2$(4-Bn-piperazin-1-yl), —$CH(C_{1-4}$ alkyl$)NH(CH_2)_n$-(5- to 6-membered heteroaryl), —$CH(C_{1-4}$ alkyl$)N(C_{1-4}$ alkyl$)_2$, —$CH(C_{1-4}$ alkyl$)N(C_{1-4}$ alkyl$)(CH_2)_n$-phenyl, —$CH(C_{1-4}$ alkyl$)N(C_{1-4}$ alkyl$)(CH_2)_n$-(5- to 6-membered heteroaryl), —$CH(C_{1-4}$ alkyl$)N$(benzyl$)(CH_2)_t$CN, —$CH(C_{1-4}$ alkyl$)N$(benzyl$)(CH_2)_t$OH, —$CH(C_{1-4}$ alkyl$)N$(benzyl$)(CH_2)_t$$OC_{1-4}$ alkyl, —$CH(C_{1-4}$ alkyl$)N$(benzyl$)(CH_2)_t$$CO_2C_{1-4}$ alkyl, —$CH(C_{1-4}$ alkyl$)N$(benzyl$)(CH_2)_t$$CONH_2$, —$CH(C_{1-4}$ alkyl$)N$(benzyl$)(CH_2)_t$$CONHC_{1-4}$ alkyl, —$CH(C_{1-4}$ alkyl$)N$(benzyl$)(CH_2)_t$$CON(C_{1-4}$ alkyl$)_2$, —$CH(C_{1-4}$ alkyl$)N$(benzyl$))(CH_2)_t$$CON(C_{1-4}$ alkyl$)$(benzyl), —$CH(C_{1-4}$ alkyl)-isoindolin-2-yl, —$CH(C_{1-4}$ alkyl)-(1,2,3,4-tetrahydroisoquinolin-2-yl), —$CH(C_{1-4}$ alkyl)(4-Bn-piperazin-1-yl), —$COC_{1-4}$ alkyl, —CO-phenyl, —CO-(5- to 6-membered heteroaryl), —CO(4-Bn-piperazin-1-yl), —$CO_2H$, —$CO_2C_{1-6}$ alkyl, —$CO_2C_{2-6}$ alkenyl, —$CONH_2$, —$CONHC_{1-6}$ alkyl —$CON(C_{1-4}$ alkyl$)_2$, —CONH-benzyl, —$CON(C_{1-4}$ alkyl)-benzyl, —CONH-phenethyl, —$CONHCH_2CH_2$NH-phenyl, —$NHCOC_{1-4}$ alkyl, —NHCO—$C_{3-6}$ cycloalkyl, —NHCO-phenyl, —NHCO-benzyl, —NHCO-phenethyl, —$NHCOCH_2OC_{1-4}$ alkyl, —$NHCOCH_2$O-phenyl, —$NHCOCH_2$O-benzyl, —NHCO(5-phenoxy-furan-2-yl), —$NHCOC(Me)_2$O-phenyl, —$NHCO_2C_{1-4}$ alkyl, —$NHCO_2$-phenyl, —$NHCO_2$-benzyl, —$NHSO_2(C_{1-4}$ alkyl), $C_{1-6}$ alkyl substituted with 0-1 $R^a$, $C_{2-6}$ alkenyl substituted with 0-1 $R^a$, phenyl, benzyl, 4-morpholinyl, 1-pyrazolyl, 1-imidazolyl, or —$NEt_3^+Cl^-$; wherein phenyl, benzyl, phenethyl, phenoxy, and benzoxy are substituted with 0-3 $R^e$; wherein 5- to 6-membered heteroaryl is substituted with 0-3 $R^e$ and selected from furanyl, thienyl, pyrrolyl, oxazolyl, thiazolyl, imidazolyl, pyrazolyl, isoxazolyl, isothiazolyl, triazolyl, tetrazolyl, pyridinyl, pyridazinyl, pyrimidinyl, pyrazinyl, and triazinyl;

alternatively, $R^1+R^2$, $R^2+R^3$, or $R^3+R^4$, combine with the carbon atoms to which they are attached, form 5- or 6-membered carbocycle or heterocycle comprising: carbon atoms and 0-3 heteroatoms selected from N, NH, O, and $S(O)_p$, and substituted with 0-2 $R^b$;

$R^5$ is phenyl substituted with 0-2 $R^b$;

alternatively, $R^5$ is

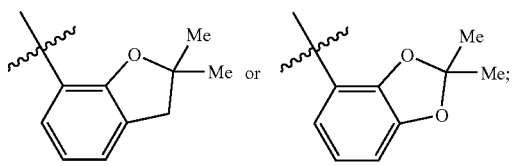

$R^7$ is H, F, Cl, Br, $C_{1-4}$ alkyl, OH, $OC_{1-4}$ alkyl, $CF_3$, $OCF_3$, $NH_2$, $NHC_{1-4}$ alkyl, $N(C_{1-4}$ alkyl$)_2$, $CO_2H$, —$CO_2C_{1-4}$ alkyl, —$CONH_2$, —$CONHC_{1-4}$ alkyl, or —$CON(C_{1-4}$ alkyl$)_2$;

$R^a$ is, independently at each occurrence, H, F, $OCF_3$, $CF_3$, OH, $OC_{1-4}$ alkyl, CN, $NH_2$, $NHC_{1-4}$ alkyl, $N(C_{1-4}$ alkyl$)_2$, —$CONH_2$, —$CONHC_{1-4}$ alkyl, or —$CON(C_{1-4}$ alkyl$)_2$;

$R^b$ is, independently at each occurrence, F, Cl, Br, $C_{1-4}$ alkyl, OH, $OC_{1-4}$ alkyl, $CF_3$, $OCF_3$, $NH_2$, $NHC_{1-4}$ alkyl, $N(C_{1-4}$ alkyl$)_2$, $CO_2H$, —$CO_2C_{1-4}$ alkyl, —$CONH_2$, —$CONHC_{1-4}$ alkyl, or —$CON(C_{1-4}$ alkyl$)_2$;

$R^e$ is, independently at each occurrence, F, Cl, Br, $C_{1-4}$ alkyl, OH, $OC_{1-4}$ alkyl, $CF_3$, $OCF_3$, $NH_2$, $NHC_{1-4}$ alkyl, $N(C_{1-4}$ alkyl$)_2$, $NO_2$, $CO_2H$, —$CO_2C_{1-4}$ alkyl, —$CONH_2$, —$CONHC_{1-4}$ alkyl, —$CON(C_{1-4}$ alkyl$)_2$, Ph, Bn, or OPh;

n, at each occurrence, is selected from 0, 1, 2, and 3; and t, at each occurrence, is selected from 1, 2, and 3.

In a fourteenth embodiment, the present invention includes compounds of Formula (Ic), or a stereoisomer or pharmaceutically acceptable salts, solvates, or prodrugs thereof, within the scope of the eleventh embodiment wherein;

R¹ is H, Me, t-Bu, OH, F, Cl, Br, CN, NH₂, NO₂, —CH₂OH, —CH(Me)OH, —CO₂Me, —CH₂NH(4-CF₃-Bn), —CH₂N(Me)Et, —CH₂N(Me)Bn, —CH₂N(Me)(4-CF₃-Bn), —CH₂(4-Bn-piperazin-1-yl), —CH(Me)N(Me)(Bn), —CO(4-Bn-1-piperazinyl), —CONH₂, —CONH-neopentyl, —CONHBn, —CONH(4-CF₃-Bn), —CON(Me)Et, —CON(Me)Bn, or —NEt₃⁺Cl⁻;

R² is H, Me, i-Pr, t-Bu, vinyl, Ph, F, Cl, Br, CF₃, OH, OMe, OEt, OPh, OBn, OCF₃, CN, NMe₂, NO₂, —COMe, —COPh, —CO-thien-2-yl, —CO₂Me, —CO₂Et, —CO₂-neopentyl, —CO₂CH₂CH=CH₂, —CH₂OH, —CH₂OEt, —CH(Me)OH, —CH(Me)OMe, —CH(Me)OCH₂C(Me)₂CH₂N(Me)₂, —CH(Me)OBn, —CH(Me)O(4-i-Pr-Bn), —CH(Me)O(3-CF₃-Bn), —CH(Me)O(4-CF₃-Bn), —CH(Me)O(4-OPh-Bn), —CH(Me)O(3,5-diCl-Bn), —CH(Me)OCH₂(1-Bn-piperidin-4-yl), —C(Me)₂OH, —CH₂NHBn, —CH₂NH(4-CF₃-Bn), —CH₂N(Me)Bn, —CH(Me)NHCH₂-pyridin-2-yl, —CH(Me)NHCH₂-pyridin-4-yl, —CH(Me)NHCH₂(6-Cl-pyridin-3-yl), —CH(Me)N(Me)(i-Bu), —CH(Me)N(Me)Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me)(3-CF₃-Bn), —CH(Me)N(Me)(4-CF₃-Bn), —CH(Me)N(Me)(3,4-diCl-Bn), —CH(Me)N(Me)CH₂CH₂Ph, —CH(Me)N(Me)CH₂-pyridin-2-yl, —CH(Me)N(Me)CH₂-pyridin-3-yl, —CH(Me)N(Me)CH₂-pyridin-4-yl, —CH(Me)N(Me)CH₂-furan-2-yl, —CH(Me)N(Me)CH₂-thien-2-yl, —CH(Me)N(Me)CH₂-(5-Me-thien-2-yl), —CH(Me)N(Me)CH₂-(5-Cl-thien-2-yl), —CH(Me)N(Et)Bn, —CH(Me)N(Et)(4-Me-Bn), —CH(Me)N(Et)(2-Cl-Bn), —CH(Me)N(Bn)CH₂CN, —CH(Me)N(Bn)CH₂CH₂OH, —CH(Me)N(Bn)CH₂CO₂Me, —CH(Me)N(Bn)CH₂CONMe₂, —CH(Me)N(Bn)CH₂CON(Me)(Bn), —CH(Me)-isoindolin-2-yl, —CH(Me)-(1,2,3,4-tetrahydroisoquinolin-2-yl), —CH(Me)(4-Bn-piperazin-1-yl), —CONH-neopentyl, —CONHBn, —CONH(4-CF₃-Bn), —CONH(4-NO₂-phenethyl), —CONHCH₂CH₂NHPh, 4-morpholinyl, or 1-pyrazolyl;

R³ is H, Me, t-Bu, Ph, OMe, OBn, F, Cl, Br, CF₃, NO₂, —CO-2-thienyl, or 1-imidazolyl;

R⁴ is H, Me, Et, i-Pr, F, Cl, Br, CF₃, NO₂, OMe, SMe, NH₂, NHMe, NHBn, —NH(4-OMe-Bn), —NH(4-CF₃-Bn), —NH(4-OCF₃-Bn), —CO₂Me, —NHCO-t-Bu, —NHCO-cyclopropyl, —NHCO-phenethyl, —NHCOCH₂OMe, —NHCOCH₂OPh, —NHCOCH₂OBn, —NHCOCH₂O-(4-t-Bu-Ph), —NHCO(4-Ph-Ph), —NHCO(5-(3,5-diCl-OPh)-furan-2-yl), —NHCOC(Me)₂O(-4-Cl-Ph), —NHCO₂Et, or —NHSO₂(i-Pr);

alternatively,

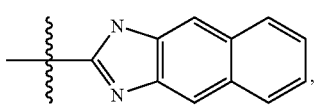

is

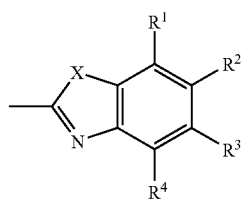

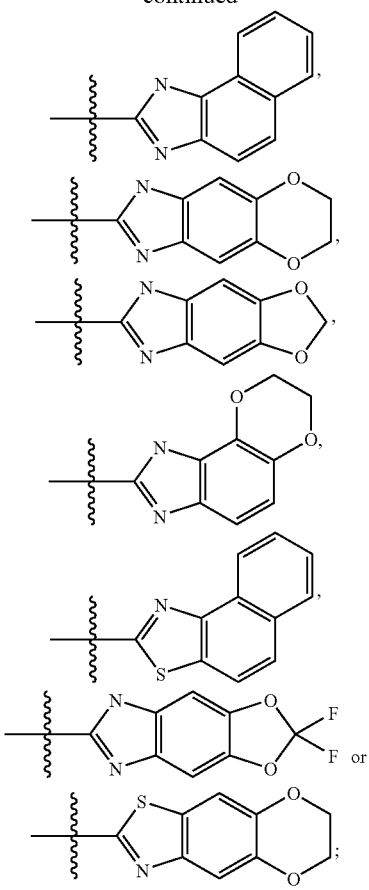

R⁵ is Ph, 2-Et, 3-Et-Ph, 2-i-Pr-Ph, 2-t-Bu-Ph, 3-F-Ph, 2-Cl-Ph, 3-Cl-Ph, 3-Br-Ph, 3-CN-Ph, 2-CF₃-Ph, 3-CF₃-Ph, 2-OCF₃-Ph, 3-OCF₃-Ph, 3-Ph-Ph, 2,3-diCl-Ph, 2,5-diCl-Ph, 3,5-diCl-Ph, 2-F-3-CF₃-Ph, 2-F-5-CF₃-Ph, 2-Cl-5-CF₃-Ph, 3,5-diCF₃-Ph, or

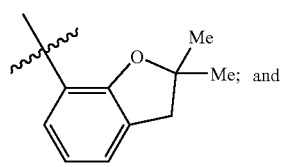

R⁷ is H, Cl, OMe, NHMe, —CO₂Me, or —CONH₂.

In a fifteenth embodiment, the present invention includes the compounds of Formula (Ib'):

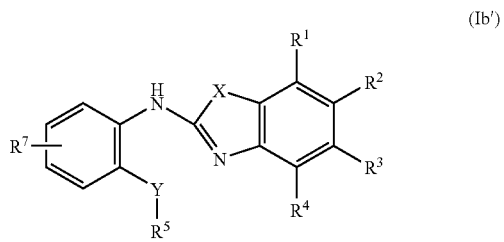

or a stereoisomer or pharmaceutically acceptable salts, solvates, or prodrugs thereof, within the scope of the eleventh embodiment.

In a sixteenth embodiment, the present invention includes the compounds of Formula (Ic'):

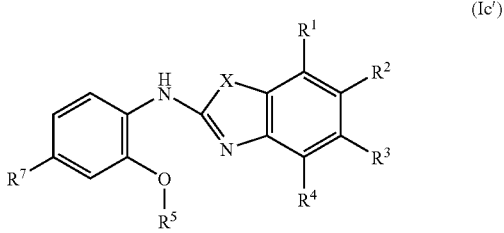

(Ic')

or a stereoisomer or pharmaceutically acceptable salts, solvates, or prodrugs thereof, wherein:

X is NH, NC$_{1-4}$ alkyl, O or S;

R$^1$, R$^2$, R$^3$, and R$^4$ are, independently at each occurrence, H, F, Cl, Br, CF$_3$, CN, OH, OC$_{1-6}$ alkyl, phenoxy, benzyloxy, SC$_{1-4}$ alkyl, OCF$_3$, NH$_2$, NHC$_{1-4}$ alkyl, N(C$_{1-4}$ alkyl)$_2$, NO$_2$, NHBn, —CH$_2$OC$_{1-4}$ alkyl, —CH(C$_{1-4}$ alkyl)OC$_{1-4}$ alkyl, —CH(C$_{1-4}$ alkyl)OCH$_2$C(Me)$_2$CH$_2$N(C$_{1-4}$ alkyl)$_2$, —CH(C$_{1-4}$ alkyl)O-benzyl, —CH(C$_{1-4}$ alkyl)OCH$_2$(1-Bn-piperidin-4-yl), —CH$_2$NH-benzyl, —CH$_2$N(C$_{1-4}$ alkyl)$_2$, —CH$_2$N(C$_{1-4}$ alkyl)-benzyl, —CH(C$_{1-4}$ alkyl)NH-benzyl, —CH$_2$(4-Bn-piperazin-1-yl), —CH(C$_{1-4}$ alkyl)NH(CH$_2$)$_n$-(5- to 6-membered heteroaryl), —CH(C$_{1-4}$ alkyl)N(C$_{1-4}$ alkyl)$_2$, —CH(C$_{1-4}$ alkyl)N(C$_{1-4}$ alkyl)(CH$_2$)$_n$-phenyl, —CH(C$_{1-4}$ alkyl)N(C$_{1-4}$ alkyl)(CH$_2$)$_n$-(5- to 6-membered heteroaryl), —CH(C$_{1-4}$ alkyl)N(benzyl)(CH$_2$)$_t$CN, —CH(C$_{1-4}$ alkyl)N(benzyl)(CH$_2$)$_t$OH, —CH(C$_{1-4}$ alkyl)N(benzyl)(CH$_2$)$_t$OC$_{1-4}$ alkyl, —CH(C$_{1-4}$ alkyl)N(benzyl)(CH$_2$)$_t$CO$_2$C$_{1-4}$ alkyl, —CH(C$_{1-4}$ alkyl)N(benzyl)(CH$_2$)$_t$CONH$_2$, —CH(C$_{1-4}$ alkyl)N(benzyl)(CH$_2$)$_t$CONHC$_{1-4}$ alkyl, —CH(C$_{1-4}$ alkyl)N(benzyl)(CH$_2$)$_t$CON(C$_{1-4}$ alkyl)$_2$, —CH(C$_{1-4}$ alkyl)N(benzyl))(CH$_2$)$_t$CON(C$_{1-4}$ alkyl)(benzyl), —CH(C$_{1-4}$ alkyl)-isoindolin-2-yl, —CH(C$_{1-4}$ alkyl)-(1,2,3,4-tetrahydroisoquinolin-2-yl), —CH(C$_{1-4}$ alkyl)(4-Bn-piperazin-1-yl), —COC$_{1-4}$ alkyl, —CO-phenyl, —CO-(5- to 6-membered heteroaryl), —CO(4-Bn-piperazin-1-yl), —CO$_2$H, —CO$_2$C$_{1-6}$ alkyl, —CO$_2$C$_{2-6}$ alkenyl, —CONH$_2$, —CONHC$_{1-6}$ alkyl, —CON(C$_{1-4}$ alkyl)$_2$, —CONH-benzyl, —CON(C$_{1-4}$ alkyl)-benzyl, —CONH-phenethyl, —CONHCH$_2$CH$_2$NH-phenyl, —NHCOC$_{1-4}$ alkyl, —NHCO—C$_{3-6}$ cycloalkyl, —NHCO-phenyl, —NHCO-benzyl, —NHCO-phenethyl, —NHCOCH$_2$OC$_{1-4}$ alkyl, —NHCOCH$_2$O-phenyl, —NHCOCH$_2$O-benzyl, —NHCO(5-phenoxy-furan-2-yl), —NHCOC(Me)$_2$O-phenyl, —NHCO$_2$C$_{1-4}$ alkyl, —NHCO$_2$-phenyl, —NHCO$_2$-benzyl, —NHSO$_2$(C$_{1-4}$ alkyl), C$_{1-6}$ alkyl substituted with 0-1 R$^a$, C$_{2-6}$ alkenyl substituted with 0-1 R$^a$, phenyl, benzyl, 4-morpholinyl, 1-pyrazolyl, 1-imidazolyl, or —NEt$_3^+$Cl$^-$; wherein phenyl, benzyl, phenethyl, phenoxy, and benzoxy are substituted with 0-3 R$^e$; wherein 5- to 6-membered heteroaryl is substituted with 0-3 R$^e$ and selected from furanyl, thienyl, pyrrolyl, oxazolyl, thiazolyl, imidazolyl, pyrazolyl, isoxazolyl, isothiazolyl, triazolyl, tetrazolyl, pyridinyl, pyridazinyl, pyrimidinyl, pyrazinyl, and triazinyl;

alternatively, R$^1$+R$^2$, R$^2$+R$^3$, or R$^3$+R$^4$, combine with the carbon atoms to which they are attached, form 5- or 6-membered carbocycle or heterocycle comprising: carbon atoms and 0-3 heteroatoms selected from N, NH, O, and S(O)$_p$, and substituted with 0-2 R$^b$;

R$^5$ is phenyl substituted with 0-2 R$^b$;

alternatively, R$^5$ is

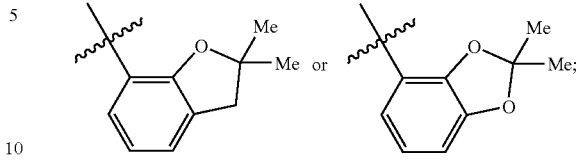

R$^7$ is H, F, Cl, Br, C$_{1-4}$ alkyl, OH, OC$_{1-4}$ alkyl, CF$_3$, OCF$_3$, NH$_2$, NHC$_{1-4}$ alkyl, N(C$_{1-4}$ alkyl)$_2$, CO$_2$H, —CO$_2$C$_{1-4}$ alkyl, —CONH$_2$, —CONHC$_{1-4}$ alkyl, or —CON(C$_{1-4}$ alkyl)$_2$;

R$^a$ is, independently at each occurrence, H, F, OCF$_3$, CF$_3$, OH, OC$_{1-4}$ alkyl, CN, NH$_2$, NHC$_{1-4}$ alkyl, N(C$_{1-4}$ alkyl)$_2$, —CONH$_2$, —CONHC$_{1-4}$ alkyl, or —CON(C$_{1-4}$ alkyl)$_2$;

R$^b$ is, independently at each occurrence, F, Cl, Br, C$_{1-4}$ alkyl, OH, OC$_{1-4}$ alkyl, CF$_3$, OCF$_3$, NH$_2$, NHC$_{1-4}$ alkyl, N(C$_{1-4}$ alkyl)$_2$, CO$_2$H, —CO$_2$C$_{1-4}$ alkyl, —CONH$_2$, —CONHC$_{1-4}$ alkyl, or —CON(C$_{1-4}$ alkyl)$_2$;

R$^e$ is, independently at each occurrence, F, Cl, Br, C$_{1-4}$ alkyl, OH, OC$_{1-4}$ alkyl, CF$_3$, OCF$_3$, NH$_2$, NHC$_{1-4}$ alkyl, N(C$_{1-4}$ alkyl)$_2$, NO$_2$, CO$_2$H, —CO$_2$C$_{1-4}$ alkyl, —CONH$_2$, —CONHC$_{1-4}$ alkyl, —CON(C$_{1-4}$ alkyl)$_2$, Ph, Bn, or OPh;

n, at each occurrence, is selected from 0, 1, 2, and 3; and t, at each occurrence, is selected from 1, 2, and 3;

provided that:

i) when R$^7$ is H or CF$_3$, then R$^1$, R$^2$, R$^3$, or R$^4$ are other than phenoxy; or ii) when R$^7$ is H, Cl, or CF$_3$, then R$^5$ is other than phenyl.

In a seventeenth embodiment, the present invention includes compounds of Formula (Ic), or a stereoisomer or pharmaceutically acceptable salts, solvates, or prodrugs thereof, within the scope of the sixteenth embodiment wherein:

R$^1$ is H, Me, t-Bu, OH, F, Cl, Br, CN, NH$_2$, NO$_2$, —CH$_2$OH, —CH(Me)OH, —CO$_2$Me, —CH$_2$NH(4-CF$_3$-Bn), —CH$_2$N(Me)Et, —CH$_2$N(Me)Bn, —CH$_2$N(Me)(4-CF$_3$-Bn), —CH$_2$(4-Bn-piperazin-1-yl), —CH(Me)N(Me)(Bn), —CO(4-Bn-1-piperazinyl), —CONH$_2$, —CONH-neopentyl, —CONHBn, —CONH(4-CF$_3$-Bn), —CON(Me)Et, —CON(Me)Bn, or —NEt$_3^+$Cl$^-$;

R$^2$ is H, Me, i-Pr, t-Bu, vinyl, Ph, F, Cl, Br, CF$_3$, OH, OMe, OEt, OPh, OBn, OCF$_3$, CN, NMe$_2$, NO$_2$, —COMe, —COPh, —CO-thien-2-yl, —CO$_2$Me, —CO$_2$Et, —CO$_2$-neopentyl, —CO$_2$CH$_2$CH═CH$_2$, —CH$_2$OH, —CH$_2$OEt, —CH(Me)OH, —CH(Me)OMe, —CH(Me)OCH$_2$C(Me)$_2$CH$_2$N(Me)$_2$, —CH(Me)OBn, —CH(Me)O(4-i-Pr-Bn), —CH(Me)O(3-CF$_3$-Bn), —CH(Me)O(4-CF$_3$-Bn), —CH(Me)O(4-OPh-Bn), —CH(Me)O(3,5-diCl-Bn), —CH(Me)OCH$_2$(1-Bn-piperidin-4-yl), —C(Me)$_2$OH, —CH$_2$NHBn, —CH$_2$NH(4-CF$_3$-Bn), —CH$_2$N(Me)Bn, —CH(Me)NHCH$_2$-pyridin-2-yl, —CH(Me)NHCH$_2$-pyridin-4-yl, —CH(Me)NHCH$_2$(6-Cl-pyridin-3-yl), —CH(Me)N(Me)(i-Bu), —CH(Me)N(Me)Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me)(3-CF$_3$-Bn), —CH(Me)N(Me)(4-CF$_3$-Bn), —CH(Me)N(Me)(3,4-diCl-Bn), —CH(Me)N(Me)CH$_2$CH$_2$Ph, —CH(Me)N(Me)CH$_2$-pyridin-2-yl, —CH(Me)N(Me)CH$_2$-pyridin-3-yl, —CH(Me)N(Me)CH$_2$-pyridin-4-yl, —CH(Me)N(Me)CH$_2$-furan-2-yl, —CH(Me)N(Me)CH$_2$-thien-2-yl, —CH(Me)N(Me)CH$_2$-(5-Me-thien-2-yl), —CH(Me)N(Me)CH$_2$-(5-Cl-thien-2-yl), —CH(Me)N(Et)Bn, —CH(Me)N(Et)(4-Me-Bn), —CH(Me)N(Et)(2-Cl-Bn), —CH(Me)N(Bn)CH$_2$CN, —CH(Me)N(Bn)CH$_2$CH$_2$OH, —CH(Me)N(Bn)CH$_2$CO$_2$Me, —CH(Me)N(Bn)CH$_2$CONMe$_2$, —CH(Me)N(Bn)CH$_2$CON(Me)(Bn), —CH(Me)-isoindolin-2-yl, —CH(Me)-(1,2,3,4-tetrahydroisoquinolin-2-yl), —CH(Me)(4-Bn-piperazin-1-yl), —CONH-neopentyl, —CONHBn, —CONH(4-CF$_3$-Bn), —CONH(4-NO$_2$-phenethyl), —CONHCH$_2$CH$_2$NHPh, 4-morpholinyl, or 1-pyrazolyl;

R$^3$ is H, Me, t-Bu, Ph, OMe, OBn, F, Cl, Br, CF$_3$, NO$_2$, —CO-2-thienyl, or 1-imidazolyl;

R$^4$ is H, Me, Et, i-Pr, F, Cl, Br, CF$_3$, NO$_2$, OMe, SMe, NH$_2$, NHMe, NHBn, —NH(4-OMe-Bn), —NH(4-CF$_3$-Bn), —NH(4-OCF$_3$-Bn), —CO$_2$Me, —NHCO-t-Bu, —NHCO-cyclopropyl, —NHCO-phenethyl, —NHCOCH$_2$OMe, —NHCOCH$_2$OPh, —NHCOCH$_2$OBn, —NHCOCH$_2$O-(4-t-Bu-Ph), —NHCO(4-Ph-Ph), —NHCO(5-(3,5-diCl-OPh)-furan-2-yl), —NHCOC(Me)$_2$O(−4-Cl-Ph), —NHCO$_2$Et, or —NHSO$_2$(i-Pr);

alternatively,

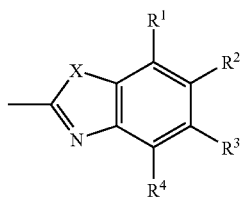

is

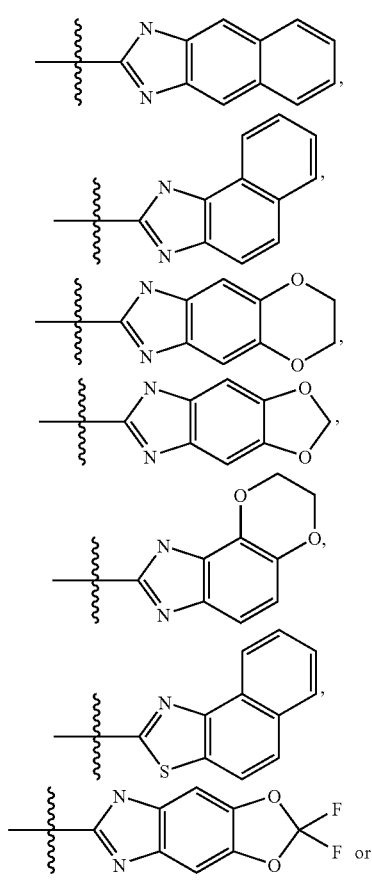

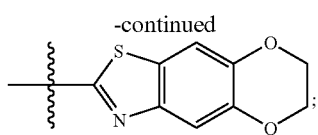

R$^5$ is Ph, 2-Et, 3-Et-Ph, 2-i-Pr-Ph, 2-t-Bu-Ph, 3-F-Ph, 2-Cl-Ph, 3-Cl-Ph, 3-Br-Ph, 3-CN-Ph, 2-CF$_3$-Ph, 3-CF$_3$-Ph, 2-OCF$_3$-Ph, 3-OCF$_3$-Ph, 3-Ph-Ph, 2,3-diCl-Ph, 2,5-diCl-Ph, 3,5-diCl-Ph, 2-F-3-CF$_3$-Ph, 2-F-5-CF$_3$-Ph, 2-Cl-5-CF$_3$-Ph, 3,5-diCF$_3$-Ph, or

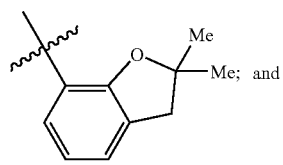

R$^7$ is H, Cl, OMe, NHMe, —CO$_2$Me, or —CONH$_2$;
provided that:
  i) when R$^7$ is H, then R$^2$ is other than OPh; or
  ii) when R$^7$ is H or CT, then R$^5$ is other than phenyl.

In a eighteenth embodiment, the present invention provides a compound selected from Examples 1 to 296 or a stereoisomer or pharmaceutically acceptable salts, solvates, or prodrugs form thereof.

In another embodiment, the present invention includes the compounds of Formula (Ic):

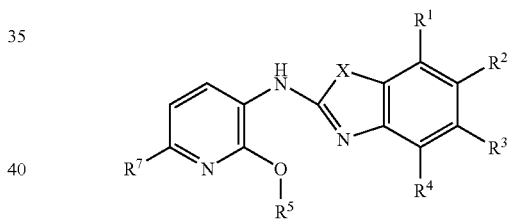

(Ic)

or a stereoisomer or pharmaceutically acceptable salts, solvates, or prodrugs thereof, wherein:
  X is NH, C or S;
  R$^1$, R$^2$, R$^3$, and R$^4$ are, independently at each occurrence, H, Me, t-Bu, Ph, F, Cl, Br, CF$_3$, OMe, OCF$_3$, CN, NO$_2$, —CO$_2$H, —CO$_2$Me, —CO$_2$Et, —COPh, —CO-2-thienyl, or 1-imidazolyl;
  alternatively, R$^1$+R$^2$, R$^2$+R$^3$, or R$^3$+R$^4$, combine with the carbon atoms to which they are attached, form 5- or 6-membered carbocycle or heterocycle comprising: carbon atoms and 0-3 heteroatoms selected from N, NH, O, and S(O)$_p$, and substituted with 0-1 R$^b$;
  R$^5$ is phenyl substituted with 0-2 R$^b$;
  R$^7$ is H, Cl, OCH$_3$, CO$_2$Me, or CONH$_2$; and
  R$^b$ is, independently at each occurrence, H, F, Cl, Br, C$_{1-4}$ alkyl, OH, CO$_2$H, NH$_2$, CF$_3$, OCF$_3$, or C$_{1-4}$ alkyloxy.

In another embodiment, the present invention includes compounds of Formula (Ic), or a stereoisomer or pharmaceutically acceptable salts, solvates, or prodrugs thereof, within the scope of the eleventh embodiment wherein:
  R$^1$ is H, Me, t-Bu or NO$_2$;
  R$^2$ is H, Me, t-Bu, Ph, F, Cl, CF$_3$, OMe, OCF$_3$, CN, NO$_2$, —CO$_2$H, —CO$_2$Me, —CO$_2$Et, —COPh, or —CO-thien-2-yl;

$R^3$ is H, Me, t-Bu, Ph, F, Cl, $CF_3$, $NO_2$, —CO-2-thienyl, or 1-imidazolyl;

$R^4$ is H, Me, F, Cl, Br, $CF_3$, or $NO_2$;

alternatively,

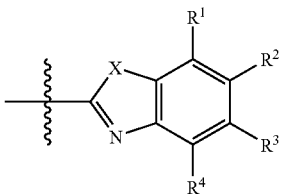

is

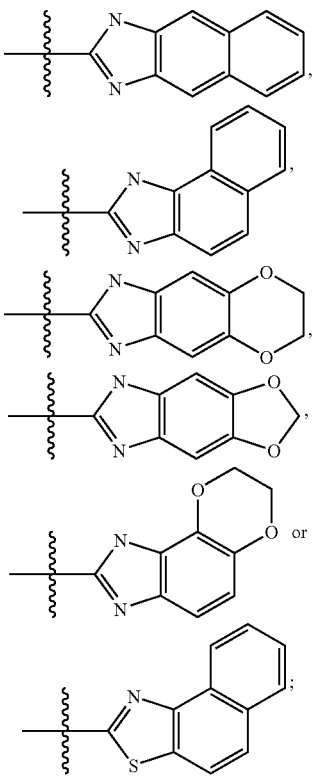

$R^5$ is Ph, 2-t-Bu-Ph, 2-Cl-Ph, 3-Et-Ph, 3-F-Ph, 3-Cl-Ph, 3-Br-Ph, 3-CN-Ph, 2-$CF_3$-Ph, 3-$CF_3$-Ph, 2-$OCF_3$-Ph, 3-$OCF_3$-Ph, 3-Ph-Ph, 2,3-diCl-Ph, 2,5-diCl-Ph, 3,5-diCl-Ph, 2-F-3-$CF_3$-Ph, 2-F-5-$CF_3$-Ph, 2-Cl-5-$CF_3$-Ph, or 3,5-di$CF_3$-Ph; and $R^7$ is H, CL, OMe, —$CO_2Me$, or —$CONH_2$.

In another embodiment the present invention provides a pharmaceutical composition comprising a pharmaceutically acceptable carrier and a therapeutically effective amount of at least one of the compounds of the present invention or a pharmaceutically acceptable salt, solvate, or prodrug form thereof.

In another embodiment the present invention provides a method for modulation of platelet reactivity comprising administering to a patient in need of such treatment a therapeutically effective amount of at least one of the compounds of the present invention or a pharmaceutically acceptable salt, solvate, or prodrug form thereof.

In another embodiment the present invention provides a method for treating thromboembolic disorders comprising: administering to a patient in need of such treatment a therapeutically effective amount of at least one of the compounds of the present invention or a pharmaceutically acceptable salt, solvate, or prodrug form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected from the group consisting of unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (e) stents, (d) cardiopulmonary bypass, (e) hemodialysis, and (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt, solvate, or prodrug form thereof in an amount effective to treat a thromboembolic disorder.

In another embodiment, the present invention provides a method for treating a thromboembolic disorder, comprising: administering to a patient in need thereof a therapeutically effective amount of a first and additional therapeutic agent(s), wherein the first therapeutic agent is a compound of Formula (I) or a pharmaceutically acceptable salt thereof and the additional therapeutic agent(s) are selected from an anti-coagulant agent, an anti-platelet agent, a thrombin inhibiting agent, a thrombolytic agent, and a fibrinolytic agent or a combination thereof.

In a preferred embodiment, the present invention provides a method for treating a thromboembolic disorder, wherein the second therapeutic agent is selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase.

In a preferred embodiment, the present invention provides a method for treating a thromboembolic disorder, wherein the additional therapeutic agent(s) are an anti-platelet agent or a combination thereof.

In a preferred embodiment, the present invention provides a method for treating a thromboembolic disorder, wherein the additional therapeutic agent(s) are the anti-platelet agent(s) clopidogrel and/or aspirin.

In another embodiment, the present invention provides a novel method, comprising: administering a compound of the present invention or a pharmaceutically acceptable salt form thereof in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The following are definitions of terms used in this specification. The initial definition provided for a group or term herein applies to that group or term throughout the present specification, individually or as part of another group, unless otherwise indicated.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

When any variable (e.g., $R^{2b}$, $R^{8b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$-$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Cycloalkyl" is intended to include saturated ring groups, having the specified number of carbon atoms. For example, "$C_3$-$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. For example, "$C_1$-$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3-, 4-, 5-, 6-, or 7-membered monocyclic or bicyclic or 7-, 8-, 9-, 10-, 11-, 12-, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, naphthyl, and indanyl. When the term "carbocycle" is used, it is intended to include "aryl".

As used herein, the term "bicyclic carbocycle" or "bicyclic carbocyclic group" is intended to mean a stable 9- or 10-membered carbocyclic ring system which contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_6$-$C_{10}$ aryl" or "aromatic residue", is intended to mean an aromatic moiety containing, if specified, the specified number of carbon atoms; for example phenyl or naphthyl. Unless otherwise specified, "aryl", "$C_6$-$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

As used herein, the term "aromatic heterocyclic system" or "heteroaryl" is intended to mean monocyclic and polycyclic aromatic hydrocarbon that include at least one heteroatom ring member such as sulfur, oxygen, or nitrogen. Preferred heteroaryl groups are stable 5-, 6-, or 7-membered monocyclic or 7-, 8-, 9-, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1.

Heteroaryl groups include, without limitation, pyridinyl, pyrimidinyl, pyrazinyl, pyridazinyl, triazinyl, furanyl, quinolyl, isoquinolyl, thienyl, imidazolyl, thiazolyl, indolyl, pyrryl, oxazolyl, benzofuranyl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional nontoxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Compounds of the present invention are, subsequent to their preparation, preferably isolated and purified to obtain a composition containing an amount by weight equal to or greater than 99% compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in viva to provide the bioactive agent (i.e., a compound of formula I) is a prodrug within the scope and spirit of the invention. Various forms of prodrugs are well known in the art. For examples of such prodrug derivatives, see:

a) *Design of Prodrugs,* edited by H. Bundgaard, (Elsevier, 1985), and *Methods in Enzymology,* Vol. 112, at pp. 309-396, edited by K. Widder, et. al. (Academic Press, 1985);

b) *A Textbook of Drug Design and Development,* edited by Krosgaard-Larsen and H. Bundgaard, Chapter 5, *"Design and Application of Prodrugs,"* by H. Bundgaard, at pp. 113-191 (1991);

c) H. Bundgaard, *Advanced Drug Delivery Reviews,* Vol. 8, p. 1-38 (1992);

d) H. Bundgaard, et al., *Journal of Pharmaceutical Sciences,* Vol. 77, p. 285 (1988); and e) N. Kakeya, et. al., *Chem Phar Bull.,* Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Therapeutically effective amount" is intended to include an amount of a compound of the present invention that is effective when administered alone or in combination to inhibit $P2Y_1$. "Therapeutically effective amount" is also intended to include an amount of the combination of compounds claimed that is effective to inhibit $P2Y_1$. The combination of compounds is preferably a synergistic combination. Synergy, as described, for example, by Chou and Talalay, *Adv. Enzyme Regul.* 1984, 22, 27-55, occurs when the effect (in this case, inhibition of $P2Y_1$) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

ABBREVIATIONS

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "M" for molar, "mmol" for millimole or millimoles, "min" for minute or minutes, "h" for hour or hours, "it" for room temperature, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" for thin layer chromatography, "$t_R$" for, and "α", "β", "R", "S", "E", and "Z" are stereochemical designations familiar to one skilled in the art.

Me—methyl
Et—ethyl
MeOH—methanol
EtOH—ethanol
i-PrOH—isopropanol
Ph—phenyl
Bn—benzyl
t-Bu—tertiary butyl
AcOH—acetic acid
EtOAc—ethyl acetate
2MeS-ADP—2 methylthio adenosine diphosphate
cDNA—complimentary DNA
DMEM—Dulbecco's modified Eagle media
DMF—dimethyl formamide
DMSO—dimethyl sulfoxide
DCE—1,2 dichloroethane
DCM—dichloromethane
DCC—dicyclohexylcarbodiimide
DIC or DIPCDI—diisopropylcarbodiimide
DIEA—diethylpropyl amine
dppf—1,1'-bis(diphenylphosphino)ferrocene
EDC or EDAC—1-[3-(dimethylamino)propyl]-3-ethylcarbodiimide hydrochloride
EDTA—ethylenediaminetetraacetic acid
FBS—Fetal Bovine Serum
HEPES—4-(2-hydroxyethyl)piperaxine-1-ethanesulfonic acid
HOBT—1-hydroxybenzotriazole hydrate
OTf—$OSO_2CF_3$
D-PBS—Dulbecco's Phosphate Buffered Saline
Pd/C—palladium on carbon
SCX—Strong Cation Exchanger
TEA—N,N,N-triethylamine
THF—tetrahydrofuran
TFA—trifluoroacetic acid
TRIS—tris(hydroxymethyl)aminomethane
EDC (or EDC.HCl) or EDCI (or EDCI.HCl) or EDAC 3-ethyl-3'-(dimethylamino)propyl-carbodiimide hydrochloride (or 1-(3-dimethylaminopropyl)-3-ethylcarbodiimide hydrochloride)

Solution ratios express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923).

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York, 1989. Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Schemes

Schemes 1 to 7 describe synthetic routes of making compounds of the invention. Schemes 1, 2, 3, 7, and 8 describe preparations of compounds of the invention from a key isothiocyanate intermediate 4.2 or an amine intermediate 4.1. Scheme 4 describes a preparation of the key isothiocyanate intermediate 4.2 from the corresponding amine 4.1. Schemes 5-6 describe a preparation of the amines 4.1 from commercially available starting materials. Scheme 7 describes an alternative general synthesis of compounds of the invention from intermediate 4.1.

Scheme 1 describes a two-step preparation of substituted benzimidazole, from the key isothiocyanate intermediate 1.1. 2-Amino substituted anilines are commercially available or can readily be prepared from commercially available materials by methods known to one skilled in the art of organic synthesis. Reaction of the thioisocyanate 1.1 with 1-amino substituted aniline 1.2 typically occurs at temperatures between 20° C. and 60° C. in a variety of solvents such as tetrahydrofuran, ethanol, dichloroethane or dioxane. The reaction leads to two isomeric thioureas 1.3 and 1.4, which can both be reacted subsequently to produce a single isomer of a benzimidazole 1.5. Transformation of the thiourea to an imidazole can be achieved with carbodiimide reagents at rt in an organic solvent such as dichloromethane, dichloroethane or dimethylformamide. Suitable carbodiimide reagents include EDC, DCC, or DIC. Alternative methods to convert 1.4 to 1.5 include treating 1.4 with yellow mercuric oxide and sulfur in boiling ethanol or treating 1.4 with methyl iodide in ethanol.

Scheme 1

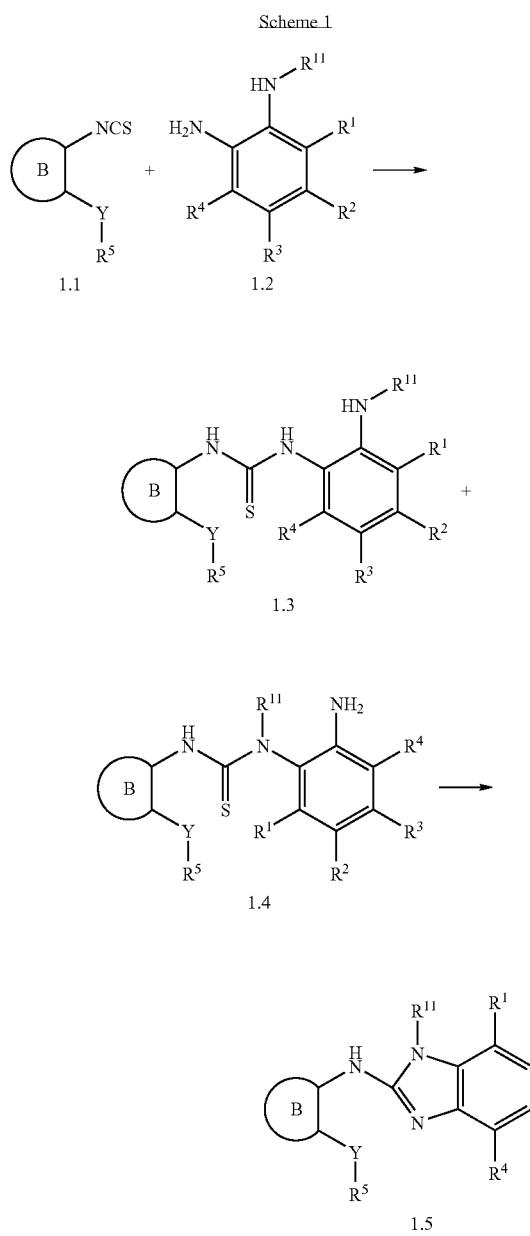

Scheme 2

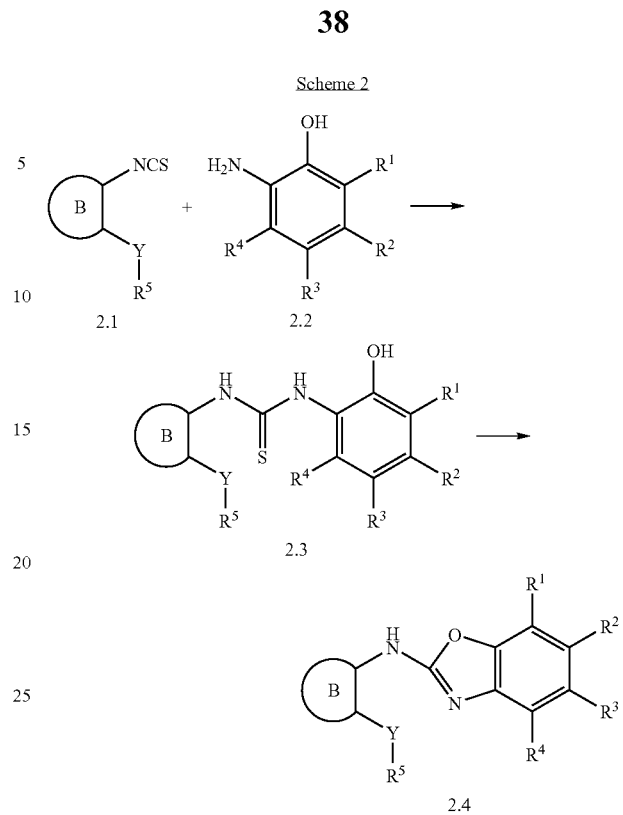

Scheme 2 describes a preparation of substituted benzoxazoles from the key isothiocyanate intermediate 2.1. 2-Amino substituted phenols are commercially available or can readily be prepared from commercially available materials by methods known to one skilled in the art of organic synthesis. Reaction of the thioisocyanate 2.1 with 1-amino substituted aniline 2.2 typically occurs at temperatures between 20° C. and 60° C. in a variety of solvents such as tetrahydrofuran, ethanol, dichloroethane or dioxane. The reaction leads to a thiourea 2.3, which can be reacted subsequently to produce a benzoxazole 2.4. Transformation of the thiourea to the benzoxazole can be achieved with carbodiimide reagents at rt in an organic solvent such as dichloromethane, dichloroethane or dimethylformamide. Suitable carbodiimide reagents include EDC, DCC, or DIC. Alternative methods to convert 2.3 to 2.4 include treating 2.3 with mercuric oxide in methanol or treating 2.3 with methyl iodide in ethanol.

Scheme 3 describes a preparation of substituted benzothiazoles from the key isothiocyanate intermediate 3.1. Substituted anilines such as 3.2 are commercially available or can readily be prepared by methods known to one skilled in the art of organic synthesis from commercially available materials. Reaction of the thioisocyanate 3.1 with the substituted aniline 3.2 typically occurs at temperatures between 20° C. and 60° C. in a variety of solvents such as tetrahydrofuran, ethanol, dichloroethane or dioxane. The reaction leads to a thiourea 3.3, which can be reacted subsequently to produce a benzothiazole 3.4. Transformation of the thiourea to the benzothiazole can be achieved by treatment with neat thionyl chloride, or by treatment with bromine in a solvent such as acetic acid or chloroform.

Scheme 3

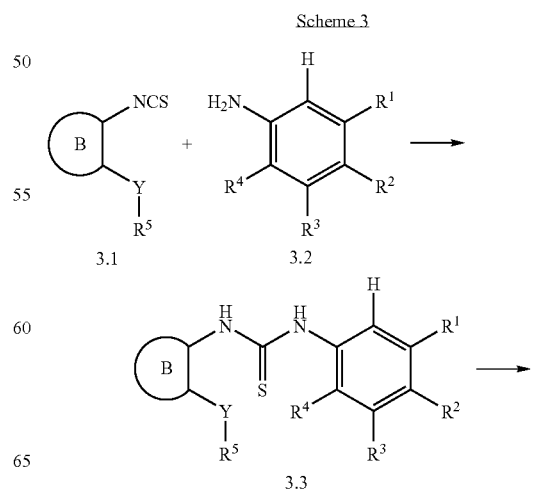

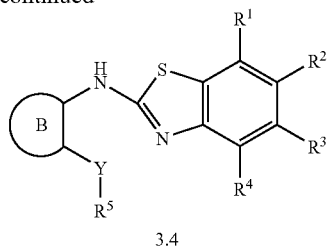

3.4

An alternative method is outlined in Scheme 3a. The key isothiocyanate intermediate 3.1 can be reacted with 2-amino substituted thiophenols 3.2b which are commercially available or can readily be prepared from commercially available materials by methods known to one skilled in the art of organic synthesis. Reaction of the thioisocyanate 3.1 with 2-amino substituted thiophenols 3.2b typically occurs at temperatures between 20° C. and 160° C. in different reaction-inert solvents such as tetrahydrofuran, pyridine, 1-methyl-2-pyrrolidinone.

Scheme 3a

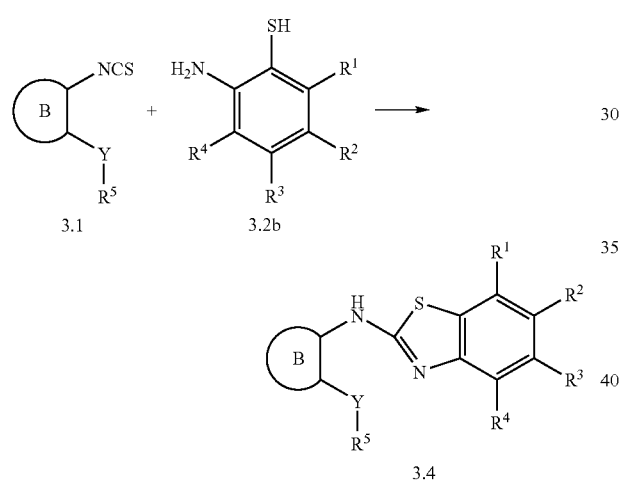

3.4

Scheme 4 outlines a preparation of the key isothiocyanate intermediate 4.2. Anilines 4.1 (prepared according to Schemes 5-6), can be treated with a thiophosgene equivalent in an organic solvent such as dichloromethane, dichloroethane or toluene, to produce the corresponding isothiocyanate. Thiophosgene equivalents include thiocarbonic acid O,O-dipyridin-2-yl ester1,1'-thiocarbonyldi-2,2'-pyridone, carbon disulfide, thiocarbonyl-diimidazole, and thiophosgene.

Scheme 4

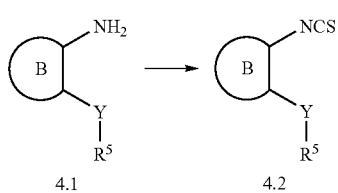

Scheme 5 outlines one possible preparation of amino derivatives 5.4, by aromatic nucleophilic substitution followed by reduction. Nitroaryl derivatives or nitroheteroaryl derivatives 4.1, substituted in the ortho position with a halogen (such as chlorine, fluorine or bromine), are commercially available or can readily be prepared by one skilled in the art of organic synthesis. They can be reacted with nucleophiles such as substituted alcohols, substituted amines, or substituted thiols to provide the corresponding ether, amine or thioether respectively. Typically, a nucleophile and a halonitro derivative are reacted in an organic solvent such as THF, DMF, toluene, dioxane or n-butanol, in presence of a base such as potassium carbonate, cesium carbonate, triethylamine, or DIEA. The temperature of the reaction is usually between rt and reflux. Occasionally, microwave irradiation can be used to accelerate the rate of reaction. The diaryl ethers are preferably synthesized by reacting an ortho chloro-nitroaryl derivative with a substituted phenol and cesium carbonate at 80° C. in DMF. The diaryl amines are preferably synthesized by reacting an ortho chloro-nitroaryl derivative with a substituted aniline and triethylamine in butanol at 210° C. using microwave irradiation.

Following aromatic nucleophilic substitution, the resulting nitro derivative 5.4 can be reduced to the corresponding aniline. Typical reducing conditions include hydrogenation in the presence of a metal catalyst such as palladium or platinum. Reduction of 5.4 or analogs may also be accomplished by treatment with reducing agents such as $SnCl_2$, or zinc powder with ammonium chloride.

Scheme 5

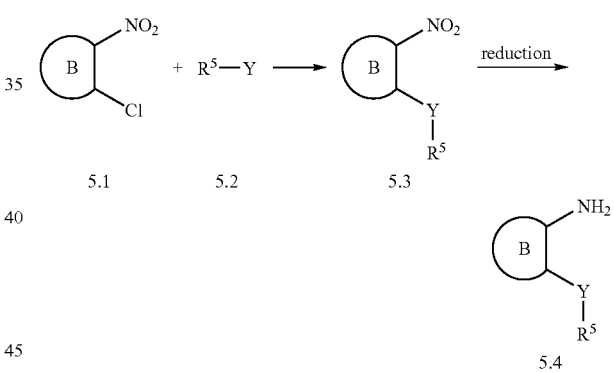

The preparation of substituted pyridine amines 6.2, 6.3, 6.4 or 6.5 is shown in Scheme 6. The pyridine aniline 6.1 (prepared as described in Scheme 5) can be brominated or chlorinated using agents such as N-bromosuccinimide or N-chlorosuccinimide in an organic solvent such as DMF. The resulting aromatic bromide can be converted to the corresponding nitrile by metal catalyzed cyanation. For example, reaction of the bromide 6.2 (X=Br) with copper (I) cyanide, tris-(dibenzylideneacetone)-bispalladium, diphenylphosphine ferrocene and tetrabutylammonium cyanide affords the corresponding nitrile 6.3. The resulting nitrile can be hydrolyzed to the corresponding carboxylic acid using methods know in the art of organic synthesis such as treatment with aqueous sodium hydroxide. Conversion of the corresponding carboxylic acid to the methyl ester can be accomplished by treatment with trimethylsilyl diazomethane or with hydrochloric acid in methanol. Alternatively, the nitrile 6.3 can be converted to the corresponding amide 6.5 by acidic or basic hydrolysis.

Scheme 6

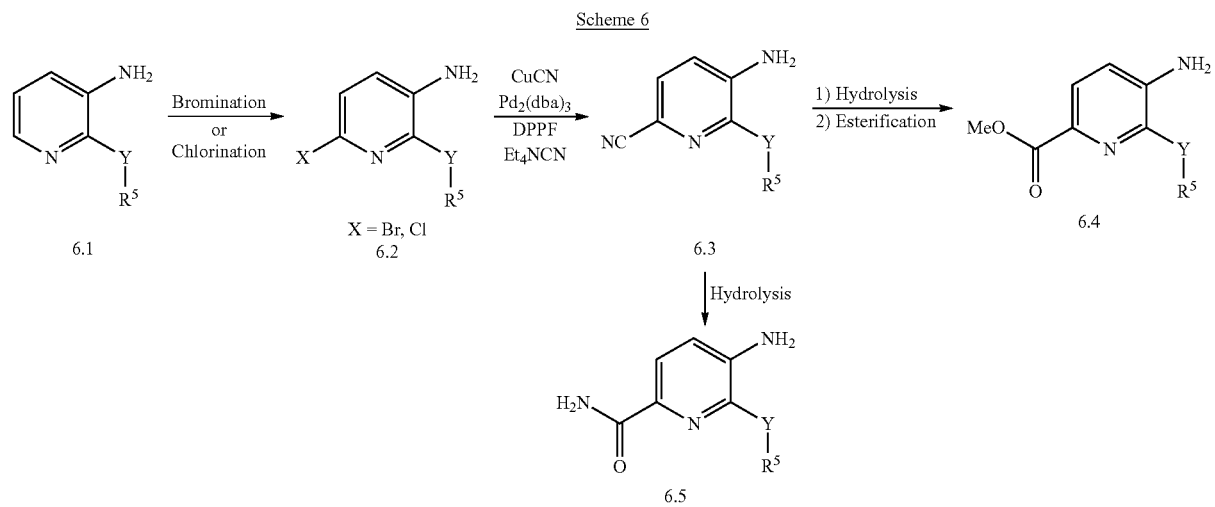

An alternative synthesis of the compounds of the invention involves the metal catalyzed coupling of the aniline 4.1 with an aryl or heteroaryl halide or triflate (Scheme 7). A variety of examples of such couplings are provided the following articles and book: Muci, A. R. et al., *Top. Curr. Chem.* 2002, 219, 131. and Hartwig, J. F., In Modern Amination Methods, Ricci, A., Ed., Wiley-VCH: Weinheim, Germany, 2000. The metal catalyst is usually palladium or nickel complexed with ligands such as a diphosphine or a ferrocene. FIG. 1 provides a non exhaustive list of possible heteroaryl halide or triflate that can be used in the reaction.

Scheme 7

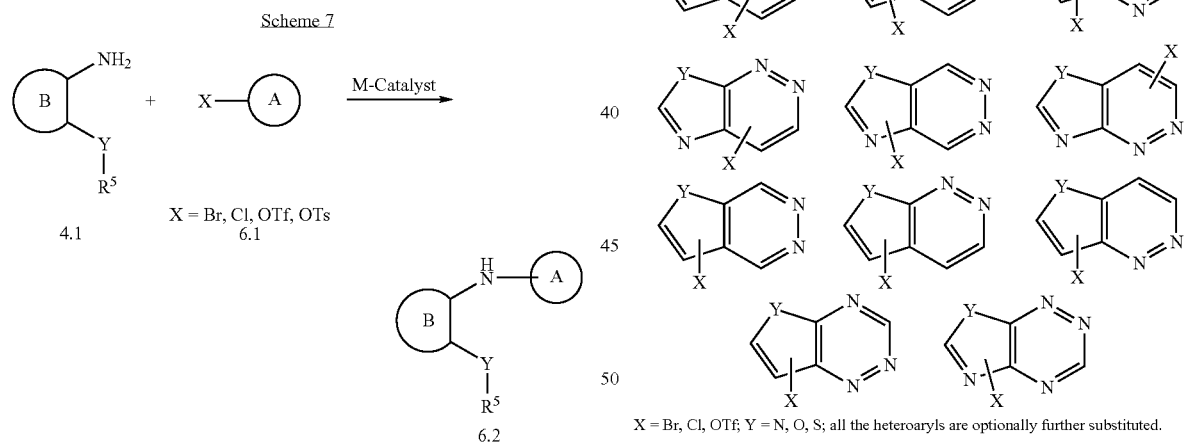

FIG. 1

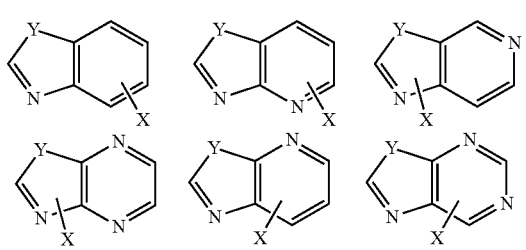

An alternative synthesis of the compounds of the invention involves the coupling of the boronic acid derivatives 8.3 (or boronate, borate) with commercially available or readily prepared by one skilled in the art amino compounds 8.4 according to the Scheme 8. Depending on the structure and substituents involved, the reaction is carried out with or without micro waves and molecular sieves, at temperatures between 0° C. and 200° C. in an appropriated organic solvent such as $CH_2Cl_2$, in the presence of a base such as pyridine or TEA. FIG. 2 provides a non exhaustive list of possible aryl or heteroaryl amines that can be used in the reaction.

The title compounds can also be prepared by one of the methods described in the reviewed article Modern Synthetic methods for cooper-mediated C(aryl)-O; C(aryl)-N and C(aryl)-S bond formation by Steven V. Lay and Andrew W. Thomas in *Angew. Chem. Int. Ed.* 2003, 42, 5400-5449. Alternatively other organometalloides such as siloxanes, stannanes or organobismuth reagents can be employed in place of boronic acid derivatives.

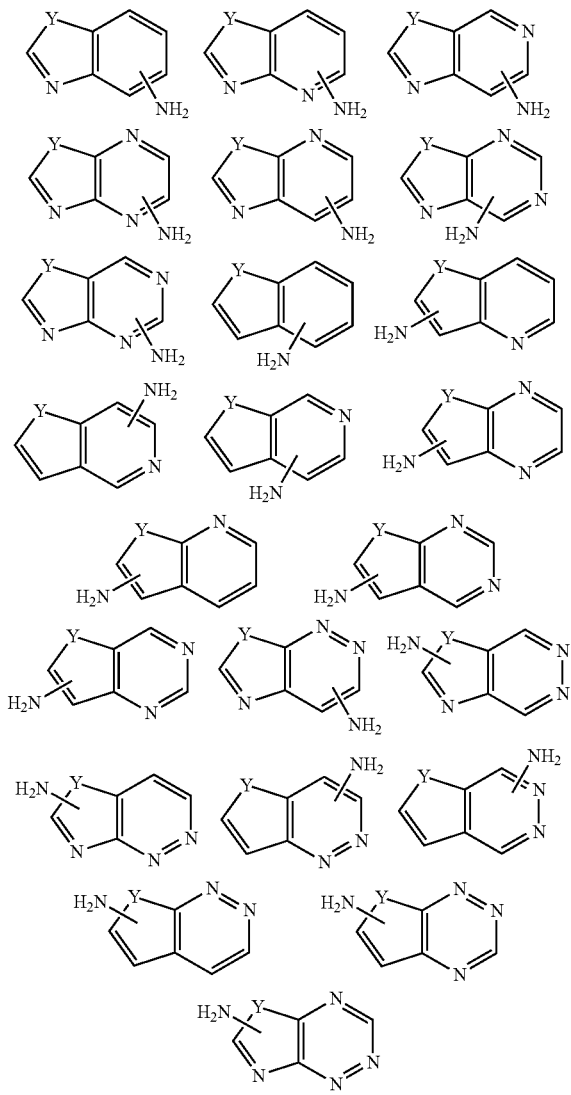

FIG. 2

Y = N, O, S; all the heteroaryls are optionally further substituted.

The amino derivative 8.1, is transformed to the corresponding halogeno intermediate 8.2 by well known diazotation reaction. In turn, 8.2 is transformed to the boronic acid compound 8.3 by the classical boronic acid derivatives preparation methods known in the literature (Pd-catalyzed borylation of aryl halides. Marshall, J. A., *Chemtracts* 2000, 13(4), 219-222; New methods for the synthesis of proximally functionalized arylboranes and silanes. Katz, H. E., *Organometallics* 1986, 5(11), 2308-11; Palladium-Catalyzed Borylation of Aryl Halides or Triflates with Dialkoxyborane: A Novel and Facile Synthetic Route to Arylboronates. Murata, M. et al., *Journal of Organic Chemistry* 2000, 65(1), 164-168).

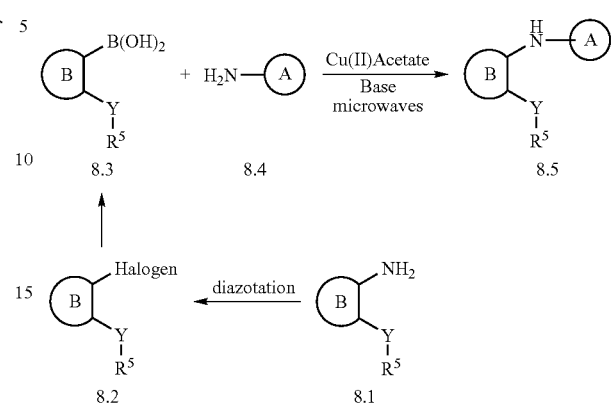

In another alternative synthesis of the compounds of the invention, the side chain functionalization can be achieved as depicted in Scheme 9. Compound 9.1 prepared according to one of the previous methods, is transformed to compounds 9.2 either by classical reductive amination procedure or by a two step reaction sequence that involves the formation of the intermediate halogeno compound 9.4. This compound is reacted with the appropriated nucleophile to yield the expected derivatives 9.5.

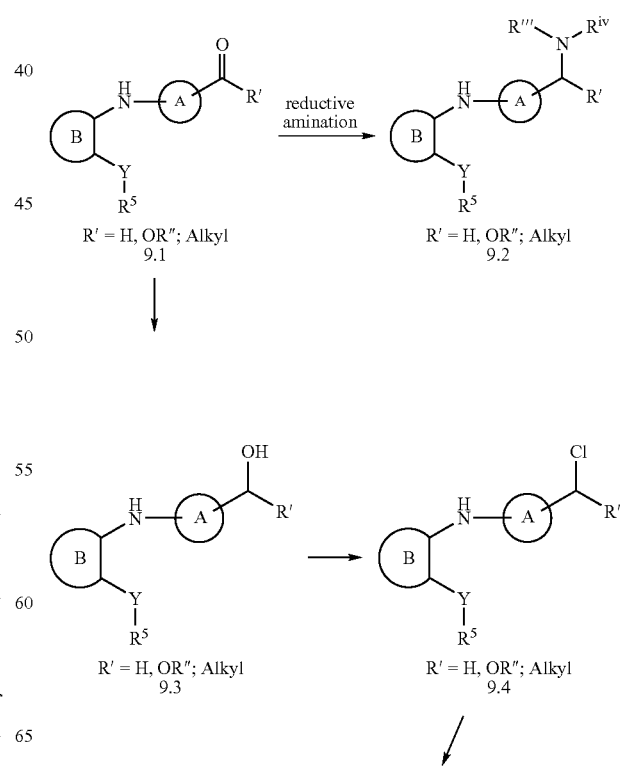

-continued

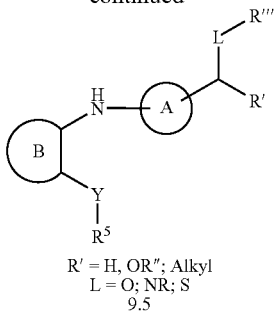

R' = H, OR''; Alkyl
L = O; NR; S
9.5

EXAMPLES

The following Examples have been prepared, isolated and characterized using the methods disclosed herein. The following Examples demonstrate a partial scope of the invention and are not meant to be limiting of the scope of the invention.

Example 1

[2-(2-tert-Butyl-phenoxy)-pyridin-3-yl]-(6-methyl-1H-benzoimidazol-2-yl)-amine

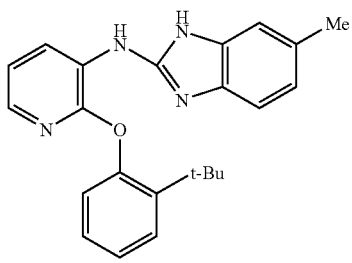

1a. 2-(2-tert-Butyl-phenoxy)-3-nitro-pyridine

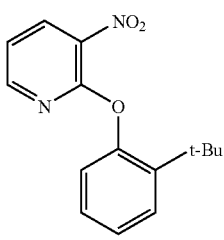

A solution of 2-chloro-3-nitropyridine (21.05 g, 132.7 mmol) in DMF (100 mL) was treated with 2-tert-butylphenol (23.5 mL, 152.6 mmol) and cesium carbonate (129.8 g, 398.3 mmol). The mixture was heated at 80° C. for 30 h. The reaction was cooled to rt, and the mixture was poured in water (1 L) with stirring. The yellow precipitate formed was filtered and washed with water, and recrystallized from ethanol to afford 1a as beige crystals (32.83 g, 90%). $^1$H NMR (400 MHz, CD$_3$OD) δ ppm 1.34 (s, 9H), 6.93 (m, 1H), 7.22 (m, 3H), 7.47 (m, 1H), 8.31 (dd, J=4.82, 1.75 Hz, 1H), 8.46 (dd, J=7.89, 1.75 Hz, 1H).

1b. 2-(2-tert-Butyl-phenoxy)-pyridin-3-ylamine

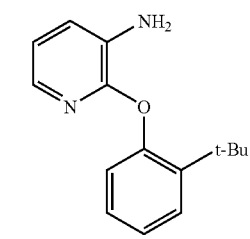

1a (7.2 g, 26.5 mmol) was dissolved in a 1:1 mixture of methanol and ethyl acetate (160 mL). Palladium on charcoal (10%, 360 mg, 0.33 mmol) was added, and the mixture was stirred overnight under hydrogen atmosphere. The reaction mixture was filtered over Celite® and concentrated to afford 7.2 g (100%) of 1b as a white powder. [M+H]$^+$=243.3.

1c. 2-(2-tert-Butyl-phenoxy)-3-isothiocyanatone

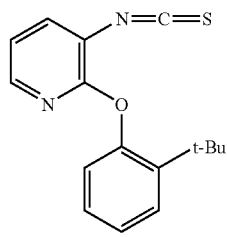

To a solution of N,N'-thiocarbonyl-diimidazole (4.4 g, 24.7 mmol) in DCM (20 mL) at 0° C. was added dropwise a solution of 1b (3.0 g, 12.4 mmol) in DCM (10 mL). The reaction mixture was slowly allowed to warm to rt. After 1 h, the mixture was concentrated. The oily residue was triturated with methanol, and the resulting white solid was filtered and rinsed with methanol. This afforded 1.72 g of the title compound 1c. The mother liquors were concentrated and triturated with methanol to afford another 200 mg of 1c. Overall yield: 54%. $^1$H NMR (400 MHz, CDCl$_3$) δ ppm 1.38 (s, 9H), 6.94 (m, 2H), 7.21 (m, 2H), 7.48 (m, 2H), 8.01 (dd, J=4.80, 1.77 Hz, 1H).

1d. 1-(2-Amino-4-methyl-phenyl)-3-[2-(2-tert-butyl-phenoxy)-pyridin-3-yl]-thiourea and 1-(2-Amino-5-methyl-phenyl)-3-[2-(2-tert-butyl-phenoxy)-pyridin-3-yl]-thiurea

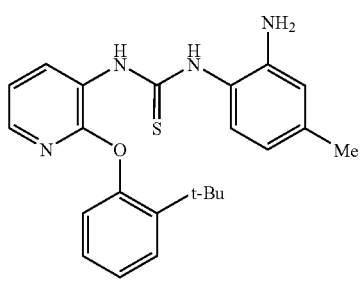

To a solution of 2,3-diamino toluene (45 mg, 0.368 mmol) in DCE (2 mL) was slowly added 1c (50 mg, 0.176 mmol). The reaction was stirred 18 h at rt and concentrated. The crude mixture containing 1d and 1d' was used in the next step without further purification. [M+H]$^+$=407.4.

Example 1

To a solution of the mixture prepared in 1d in dichloroethane (2 mL) was added EDC (50 mg, 261 mmol) and the mixture was stirred overnight at rt. More EDC (20 mg, 104 mmol) was added to the reaction, and the mixture was stirred another 18 h at rt. The mixture was concentrated and purified by preparative HPLC (continuous gradient from 0% B to 100% B; A=90:10:0.1 H$_2$O:MeOH:TFA; B=90:10:0.1 MeOH:H$_2$O:TFA) to afford Example 1 (55 mg, 75% yield) as a pink powder. [M+H]$^+$=373.5. $^1$H NMR (400 MHz, CD$_3$OD) δ ppm 1.13 (s, 9H), 2.39 (s, 3H), 6.95 (dd, J=7.96, 1.39 Hz, 1H), 7.13 (m, 4H), 7.24 (m, 2H), 7.35 (dd, J=7.83, 1.52 Hz, 1H), 7.98 (dd, J=7.71, 1.64 Hz, 1H), 8.12 (dd, J=4.80, 1.77 Hz, 1H).

Example 2

(6-tert-Butyl-1H-benzoimidazol-2-yl)-[2-(2-tert-butyl-phenoxy)-6-methoxy-pyridin-3-yl]-amine

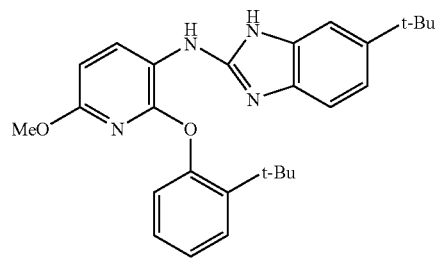

2a. 2-(2-tert-Butyl-phenoxy)-6-methoxy-3-nitropyridine

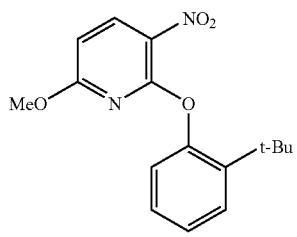

A solution of 2-chloro-6-methoxy-3-nitropyridine (5.20 g, 27.6 mmol) in DMF (50 mL) was treated with 2-tert-butylphenol (4.9 mL, 31.7 mmol) and cesium carbonate (27.0 g, 82.8 mmol). The mixture was heated at 80° C. for 18 h. The reaction was allowed to cool to rt, the mixture was poured into water (500 mL) with stirring. The brown precipitate formed was filtered and washed with water, and recrystallized twice from ethanol to afford 2a as brown crystals (6.66 g, 80%). [M+H]$^+$=303.2.

2b. 2-(2-tert-Butyl-phenoxy)-6-methoxy-pyridin-3-ylamine

To a solution of 2a (580 mg, 1.9 mmol) in a 1:1 mixture of ethyl acetate and methanol (6 mL) was added palladium on charcoal (10% wt, 300 mg, 0.28 mmol). The mixture was stirred under 40 psi atmosphere of hydrogen. After 30 min, the solution was filtered over Celite® and the resulting solution was concentrated to afford the title compound 2b as a dark solution (500 mg, 96% yield). 2b was used in the next step without any further purification. [M+H]+=273.21. ¹H NMR (500 MHz, CD₃OD) δ ppm 1.43 (m, 9H), 3.58 (m, 3H), 6.33 (d, J=8.25 Hz, 1H), 6.93 (d, J=8.25 Hz, 1H), 7.09 (m, 2H), 7.17 (t, J=7.70 Hz, 1H), 7.41 (d, J=8.25 Hz, 1H).

2c. 2-(2-tert-Butyl-phenoxy)-3-isothiocyanato-6-methoxy-pyridine

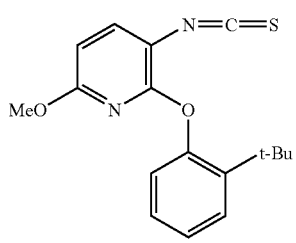

To a solution of N,N'-thiocarbonyl-diimidazole (1.3 g, 7.3 mmol) in DCM (30 mL) at 0° C. was added dropwise a solution of 2b (1.0 g, 3.67 mmol) in DCM (20 mL). After stirring at 0° C. for 1 h, the reaction mixture was slowly allowed to rt. After 1 h, the mixture was concentrated. Column chromatography on silica gel using 20% ethyl acetate in hexanes as eluent afforded 1.05 g (91% yield) of 2c as a yellow oil. [M+H]+=315.09. ¹H NMR (500 MHz, CDCl₃) δ ppm 1.37 (m, 9H), 3.55 (s, 3H), 6.35 (d, J=8.25 Hz, 1H), 6.96 d, J=7.70 Hz, 1H), 7.14 (t, J=7.42 Hz, 1H), 7.19 (t, J=7.70 Hz, 1H), 7.42 (d, J=8.25 Hz, 2H).

2d. 1-(2-Amino-4-tert-butyl-phenyl)-3-[2-(2-tert-butyl-phenoxy)-6-methoxy-pyridin-3-yl]-thiourea and 1-(2-Amino-5-tert-butyl-phenyl)-3-[2-(2-tert-butyl-phenoxy)-6-methoxy-pyridin-3-yl]-thiourea

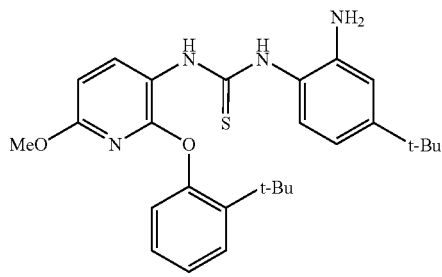

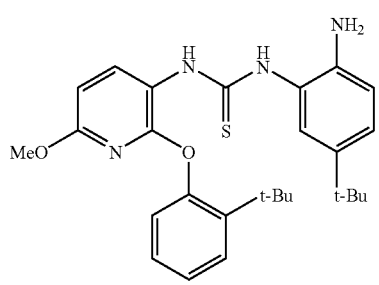

To a solution of 4-(tert-butyl)-1,2-diaminobenzene (20 mg, 0.12 mmol) in DCE (1 mL) was slowly added 2c (19 mg, 0.06 mmol). The reaction was stirred 18 h at rt and concentrated. The crude mixture containing 2d and 2d' was used in the next step without further purification.

Example 2

To a solution of the mixture from 2d in dichloroethane (2 mL) was added EDC (23 mg, 0.12 mmol) and the mixture was stirred overnight at rt. The mixture was concentrated and purified by preparative HPLC (continuous gradient from 20% B to 100% B; A=90:10:0.1 H₂O:MeOH:TFA; B=90:10:0.1 MeOH:H₂O:TFA) to afford Example 2 (22 mg, 66% yield). [M+H]+=445.28.

Example 3

(6-tert-Butyl-1H-benzoimidazol-2-yl)-[2-(3-trifluoromethyl-phenoxy)-pyridin-3-yl]-amine

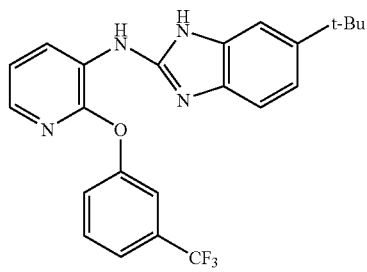

3a. 3-Nitro-2-(3-trifluoromethyl-phenoxy)-pyridine

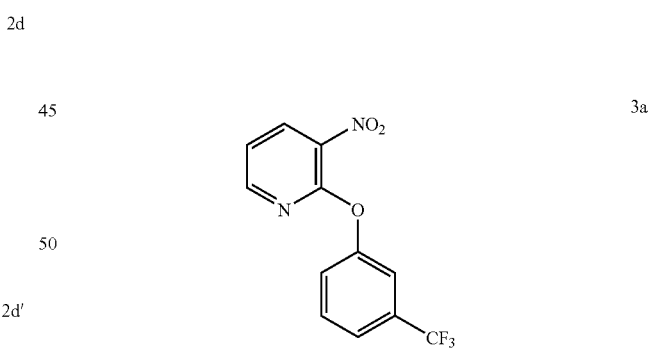

A solution of 2-chloro-6-methoxy-3-nitropyridine (20 g, 125 mmol) in DMF (120 mL) was treated with 3-trifluoromethylphenol (21 g, 129 mmol) and cesium carbonate (50 g, 154 mmol). The mixture was heated at 70° C. for 14 h. The reaction was concentrated. The residue was dissolved in ethyl acetate and washed with brine, 5% lithium chloride, and aqueous HCl and brine. After concentration, purification was achieved by column chromatography on silica gel using a continuous gradient from 0% to 40% ethyl acetate in hexanes as eluent afforded 21 g (60% yield) of 3a as a white crystals. [M+H]+=285.17.

3b. 2-(3-Trifluoromethyl-phenoxy)-pyridin-3-ylaine

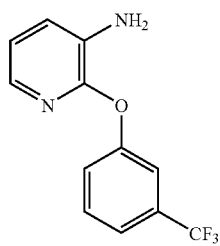

To a solution of 3a (20 g, 70 mmol) in a 1:4 mixture of ethyl acetate and methanol (250 mL) was added palladium on charcoal (10% wt, 1.0 g, 0.90 mmol), and the mixture was stirred under an atmosphere of hydrogen. After 3 h, the solution was filtered over Celite® and the resulting solution was concentrated. 3b was recrystallized from ethyl acetate to afford 17.5 g of white crystals (97% yield). [M+H]$^+$=255.20.

3c. 3-Isothiocyanato-2-(3-trifluoromethyl-phenoxy)-pyridine

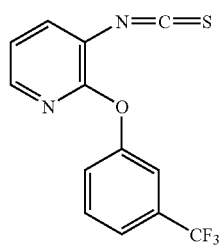

To a solution of N,N'-thiocarbonyl-diimidazole (2.45 g, 13.7 mmol) in DCM (50 mL) at 0° C. was added dropwise a solution of 3b (2.0 g, 6.90 mmol) and triethylamine (0.7 ml, 5 mmol) in DCM (20 mL). After stirring at 0° C. for 1 h, the reaction mixture was slowly allowed to rt. After 3 h, the mixture was concentrated and purified by column chromatography on silica gel using a continuous gradient from 0% to 40% ethyl acetate in hexanes as eluent afforded 1.3 g (91% yield) of 3c as a white crystals. $^1$H NMR (500 MHz, CDCl$_3$) δ ppm 7.02 (dd, J=7.71, 4.93 Hz, 1H), 7.41 (d, J=8.08 Hz, 1H), 7.51 (m, 4H), 7.99 (dd, J=5.05, 1.77 Hz, 1H).

3d. 1-(2-Amino-4-tert-butyl-phenyl)-3-[2-(3-trifluoromethyl-phenoxy)-pyridin-3-yl]-thiourea and 1-(2-Amino-5-ter-butyl-phenyl)-3-[2-(3-trifluoromethyl-phenoxy)-pyridin-3-yl]-thiourea

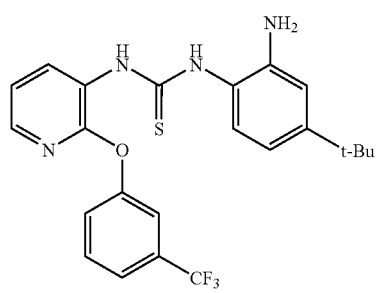

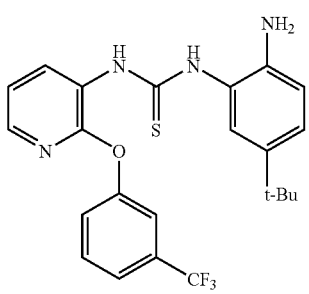

To a solution of 4-(tert-butyl)-1,2-diaminobenzene (20 mg, 0.12 mmol) in DCE (1 mL) was slowly added 3c (19 mg, 0.06 mmol). The reaction was stirred 18 h at rt and concentrated. The crude mixture containing 3d and 3d' was used in the next step without further purification.

Example 3

To a solution of the mixture prepared in 3d in dichloroethane (2 mL) was added EDC (23 mg, 0.12 mmol) and the mixture was stirred overnight at rt. The mixture was concentrated and purified by preparative HPLC (continuous gradient from 20% B to 100% B; A=90:10:0.1 H$_2$O:MeOH:TFA; B=90:10:0.1 MeOH:H$_2$O:TFA) to afford Example 3 (14 mg, 21% yield). [M+H]$^+$=427.15.

Example 4

[2-(2-tert-Butyl-phenoxy)-pyridin-3-yl]-(5-methyl-benzooxazol-2-yl)-amine

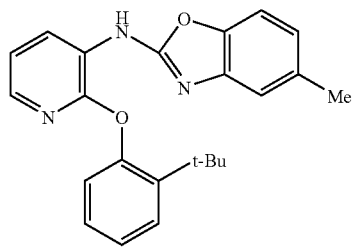

4a. 1-[2-(2-tert-Butyl-phenoxy)-pyridin-3-yl]-3-(2-hydroxy-5-methyl-phenyl)-thiourea

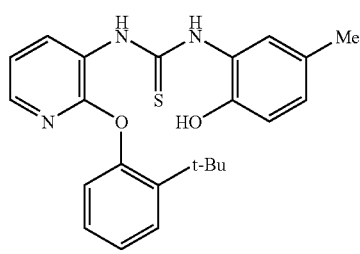

Compound 1c (20 mg, 0.07 mmol) and 2-amino-p-cresol (9 mg, 0.06 mmol) were mixed in DCE (1.0 mL) and stirred for 2 days at rt. The reaction mixture was concentrated. Half of the crude reaction mixture was used in the next step without further purification. The other half was purified by preparative HPLC (continuous gradient from 30% B to 100% B; A=90:10:0.1 H$_2$O:MeOH:TFA; B=90:10:0.1 MeOH:H$_2$O:TFA) to afford 12 mg (90%) of 4a. [M+H]$^+$=408.39. $^1$H NMR (400 MHz, CD$_3$OD) δ ppm 1.23 (d, J=2.27 Hz, 9H), 2.11 (s, 3H), 6.72 (m, 1H), 6.84 (m, 2H), 7.10 (m, 3H), 7.20 (s, 1H), 7.37 (dd, J=7.83, 1.77 Hz, 1H), 7.80 (dd, J=4.80, 1.77 Hz, 1H), 8.60 (d, J=7.83 Hz, 1H).

Example 4

To a solution of the crude reaction mixture prepared in 4a (12 mg, 0.035 mmol) in dichloroethane (1 mL) was added EDC (10 mg, 0.052 mmol), and the mixture was stirred overnight at rt. The mixture was concentrated and purified by preparative HPLC (continuous gradient from 30% B to 100% B; A=90:10:0.1 H$_2$O:MeOH:TFA; B=90:10:0.1 MeOH:H$_2$O:TFA) to afford Example 4 (3 mg, 23% yield) as a white powder. [M+H]$^+$=374.37. $^1$H NMR (400 MHz, CD$_3$OD) δ ppm 1.28 (m, 9H), 2.35 (s, 3H), 6.91 (m, 2H), 7.14 (m, 5H), 7.39 (dd, J=7.83, 1.52 Hz, 1H), 7.75 (dd, J=4.93, 1.64 Hz, 1H), 8.50 (dd, J=7.83, 1.52 Hz, 1H).

Examples 5 to 92

Examples 5 to 92 listed in Tables 1-2 below were prepared in an identical manner to examples 1-4 above. 1c, 2c, or 3c (0.06 mmol) were reacted with the appropriately substituted 2-amino aniline or 2-amino phenol (0.12 mmol) in DCE (1 mL) for 18 h at rt. After concentration, the resulting thiourea was reacted with EDC (0.12 mmol) for 18 h at rt. The crude reaction mixture was concentrated and purified by preparative HPLC (continuous gradient from 30% B to 100% B; A=90:10:0.1 H$_2$O:MeOH:TFA; B=90:10:0.1 MeOH:H$_2$O:TFA) to afford the desired compound in 5-70% yield.

TABLE 1

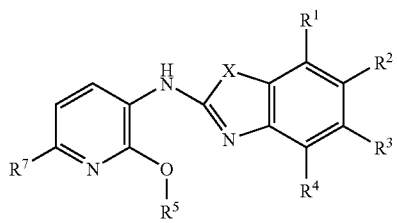

| Ex. No. | X | R$^1$ | R$^2$ | R$^3$ | R$^4$ | R$^5$ | R$^7$ | MS (M + 1) |
|---|---|---|---|---|---|---|---|---|
| 5 | NH | NO$_2$ | Me | H | H | 2-t-Bu-Ph | H | 418.17 |
| 6 | NH | H | t-Bu | H | H | 2-t-Bu-Ph | H | 415.23 |
| 8 | O | H | H | Cl | H | 2-t-Bu-Ph | H | 394.07 |
| 9 | O | H | H | t-Bu | H | 2-t-Bu-Ph | H | 416.21 |
| 10 | NH | H | H | H | NO$_2$ | 2-t-Bu-Ph | H | 404.11 |
| 11 | NH | H | Cl | Cl | H | 2-t-Bu-Ph | H | 427.08 |
| 12 | NH | H | Me | Me | H | 2-t-Bu-Ph | H | 387.15 |
| 13 | NH | Me | H | H | H | 2-t-Bu-Ph | H | 373.14 |
| 14 | NH | H | CO$_2$Me | H | H | 2-t-Bu-Ph | H | 417.17 |
| 16 | NH | H | CF$_3$ | H | Cl | 2-t-Bu-Ph | H | 461.08 |
| 17 | NH | H | H | F | H | 2-t-Bu-Ph | H | 377.12 |
| 18 | NH | H | H | CF$_3$ | H | 2-t-Bu-Ph | H | 427.14 |
| 19 | NH | H | CF$_3$ | H | Br | 2-t-Bu-Ph | H | 505.04 |
| 20 | NH | H | F | Cl | H | 2-t-Bu-Ph | H | 411.11 |
| 21 | NH | H | OMe | H | H | 2-t-Bu-Ph | H | 389.14 |
| 22 | NH | Me | Me | H | H | 2-t-Bu-Ph | H | 387.16 |
| 23 | O | H | H | Ph | H | 2-t-Bu-Ph | H | 436.25 |
| 24 | NH | H | F | F | H | 2-t-Bu-Ph | H | 395.12 |

TABLE 1-continued

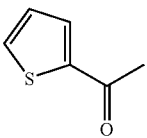

| Ex. No. | X | R¹ | R² | R³ | R⁴ | R⁵ | R⁷ | MS (M + 1) |
|---|---|---|---|---|---|---|---|---|
| 25 | NH | H | Cl | Me | H | 2-t-Bu-Ph | H | 407.12 |
| 26 | NH | H | CN | H | H | 2-t-Bu-Ph | H | 384.11 |
| 27 | NH | H | F | H | F | 2-t-Bu-Ph | H | 395.11 |
| 29 | NH | H | H | 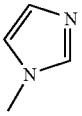 | H | 2-t-Bu-Ph | H | 469.13 |
| 30 | NH | Me | H | 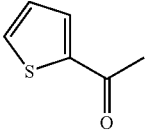 | H | 2-t-Bu-Ph | H | 439.19 |
| 32 | NH | H | H | H | NO₂ | 2-t-Bu-Ph | OMe | 434.16 |
| 33 | NH | H | Cl | Cl | H | 2-t-Bu-Ph | OMe | 457.08 |
| 34 | NH | H | H | NO₂ | H | 2-t-Bu-Ph | OMe | 434.17 |
| 35 | NH | H | COPh | H | H | 2-t-Bu-Ph | OMe | 493.2 |
| 36 | NH | H | Me | H | H | 2-t-Bu-Ph | OMe | 403.16 |
| 37 | NH | H | Me | Me | H | 2-t-Bu-Ph | OMe | 417.25 |
| 38 | NH | Me | H | H | H | 2-t-Bu-Ph | OMe | 403.25 |
| 39 | NH | H | H | Cl | H | 2-t-Bu-Ph | OMe | 423.21 |
| 40 | NH | H | CO₂Me | H | H | 2-t-Bu-Ph | OMe | 447.22 |
| 42 | NH | H | CF₃ | H | Cl | 2-t-Bu-Ph | OMe | 491.16 |
| 43 | NH | H | H | F | H | 2-t-Bu-Ph | OMe | 407.15 |
| 44 | NH | H | H | CF₃ | H | 2-t-Bu-Ph | OMe | 457.14 |
| 45 | NH | H | CF₃ | H | Br | 2-t-Bu-Ph | OMe | 535.06 |
| 46 | NH | H | F | Cl | H | 2-t-Bu-Ph | OMe | 441.17 |
| 47 | NH | H | OMe | H | H | 2-t-Bu-Ph | OMe | 419.19 |
| 48 | NH | Me | Me | H | H | 2-t-Bu-Ph | OMe | 417.21 |
| 49 | NH | H | F | F | H | 2-t-Bu-Ph | OMe | 425.16 |
| 50 | NH | H | CO₂Et | H | H | 2-t-Bu-Ph | OMe | 461.22 |
| 51 | NH | H | Cl | Me | H | 2-t-Bu-Ph | OMe | 437.21 |
| 52 | NH | H | CN | H | H | 2-t-Bu-Ph | OMe | 414.24 |
| 53 | NH | H | F | H | F | 2-t-Bu-Ph | OMe | 425.22 |
| 56 | NH | H | CF₃ | H | CF₃ | 2-t-Bu-Ph | OMe | 525.14 |
| 57 | NH | H | H | 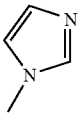 | H | 2-t-Bu-Ph | OMe | 499.14 |
| 58 | NH | Me | H | | H | 2-t-Bu-Ph | OMe | 469.18 |
| 61 | O | H | H | t-Bu | H | 3-CF₃-Ph | H | 428.13 |
| 62 | NH | H | H | H | NO₂ | 3-CF₃-Ph | H | 416.07 |
| 63 | NH | H | Cl | Cl | H | 3-CF₃-Ph | H | 439 |
| 64 | NH | H | H | NO₂ | H | 3-CF₃-Ph | H | 416.07 |
| 65 | NH | H | Me | H | H | 3-CF₃-Ph | H | 385.08 |
| 66 | NH | H | Me | Me | H | 3-CF₃-Ph | H | 399.11 |
| 67 | NH | Me | H | H | H | 3-CF₃-Ph | H | 385.07 |
| 68 | NH | H | H | Cl | H | 3-CF₃-Ph | H | 405.04 |
| 69 | NH | H | CO₂Me | H | H | 3-CF₃-Ph | H | 429.09 |
| 71 | NH | H | CF₃ | H | Cl | 3-CF₃-Ph | H | 473.01 |
| 72 | NH | H | H | F | H | 3-CF₃-Ph | H | 389.06 |

TABLE 1-continued

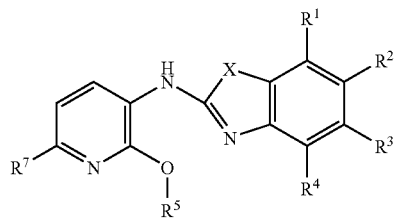

| Ex. No. | X | R¹ | R² | R³ | R⁴ | R⁵ | R⁷ | MS (M + 1) |
|---|---|---|---|---|---|---|---|---|
| 73 | NH | H | CF₃ | H | H | 3-CF₃-Ph | H | 439.07 |
| 74 | NH | H | CF₃ | H | Br | 3-CF₃-Ph | H | 516.98 |
| 75 | NH | H | F | Cl | H | 3-CF₃-Ph | H | 423.04 |
| 76 | NH | H | OMe | H | H | 3-CF₃-Ph | H | 401.08 |
| 77 | NH | Me | Me | H | H | 3-CF₃-Ph | H | 399.1 |
| 78 | NH | H | Ph | H | H | 3-CF₃-Ph | H | 448.09 |
| 79 | NH | H | F | F | H | 3-CF₃-Ph | H | 407.06 |
| 80 | NH | H | Cl | Me | H | 3-CF₃-Ph | H | 419.08 |
| 81 | NH | H | CN | H | H | 3-CF₃-Ph | H | 396.05 |
| 82 | NH | H | F | H | F | 3-CF₃-Ph | H | 407.06 |
| 85 | NH | H | CF₃ | H | CF₃ | 3-CF₃-Ph | H | 507.05 |
| 87 | NH | H | Cl | H | H | 2-t-Bu-Ph | H | 393.09 |
| 88 | NH | H | COPh | H | H | 2-t-Bu-Ph | H | 463.28 |
| 89 | NH | H | CO₂Et | H | H | 2-t-Bu-Ph | H | 431.67 |
| 91 | NH | H |  | H | H | 3-CF₃-Ph | H | 481.04 |
| 92 | O | H | Me | H | H | 2-t-Bu-Ph | H | 372.37 |

TABLE 2

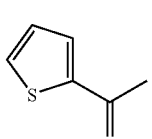

| Ex. No. | (fused ring) | R⁵ | R⁷ | MS (M + 1) |
|---|---|---|---|---|
| 7 | 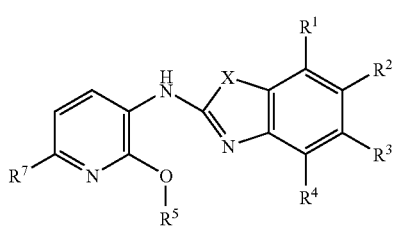 | 2-t-Bu-Ph | H | 409.17 |
| 15 | 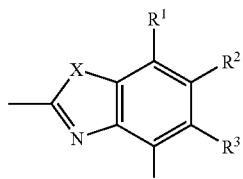 | 2-t-Bu-Ph | H | 409.17 |
| 28 | 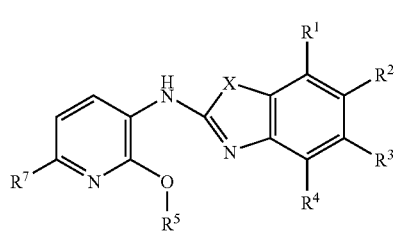 | 2-t-Bu-Ph | H | 417.17 |
| 31 | 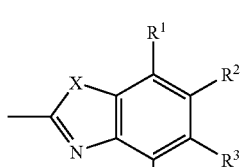 | 2-t-Bu-Ph | H | 403.15 |

TABLE 2-continued
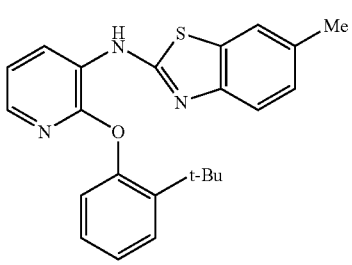
| Ex. No. | R⁵ | R⁷ | MS (M + 1) |
|---|---|---|---|
| 41 | 2-t-Bu-Ph | OMe | 439.24 |
| 54 | 2-t-Bu-Ph | OMe | 447.16 |
| 55 | 2-t-Bu-Ph | OMe | 447.17 |
| 59 | 2-t-Bu-Ph | OMe | 433.16 |
| 60 | 3-CF₃-Ph | H | 421.11 |
| 70 | 3-CF₃-Ph | H | 421.11 |
| 83 | 3-CF₃-Ph | H | 429.09 |
| 84 | 3-CF₃-Ph | H | 429.09 |
| 86 | 3-CF₃-Ph | H | 415.07 |
| 90 | 2-t-Bu-Ph | H | 417.17 |
Example 93
N-(2-(2-tert-Butylphenoxy)pyridin-3-yl)-6-methyl-benzo[d]thiazol-2-amine 93a. 1-(2-(2-tert-Butylphenoxy)pyridin-3-yl)-3-p-tolylthiourea

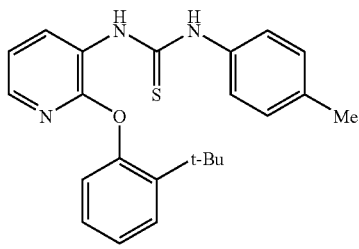

93a

To a solution of 4-amino toluene (8 mg, 0.075 mmol) in DCE (2 mL) was slowly added 1e (20 mg, 0.07 mmol). The reaction was stirred 18 h at rt and concentrated. The crude mixture was dissolved in methanol and filtered through an SCX cartridge. Half of the material obtained was carried to the next step without further purification. The other half was purified by preparative HPLC (continuous gradient from 0% B to 100% B; A=90:10:0.1 $H_2O$:MeOH:TFA; B=90:10:0.1 MeOH:$H_2O$:TFA) to afford 93a (13 mg, 94% yield) as a white powder. $[M+H]^+=392.39$.

Example 93

Half of the crude material obtained in 93a was treated with thionyl chloride (0.5 mL) for 1 h at rt. The mixture was concentrated and the residue was purified by preparative HPLC (continuous gradient from 30% B to 100% B; A=90:10:0.1 $H_2O$:MeOH:TFA; B=90:10:0.1 MeOH:$H_2O$:TFA) to afford Example 93 (5 mg, 36% yield) as a white powder. $[M+H]^+=390.38$.

Examples 94 and 95

N-(2-(2-tert-Butylphenoxy)pyridin-3-yl)-5-methyl-benzo[d]thiazol-2-amine and N-(2-(2-tert-Butylphenoxy)pyridin-3-yl)-7-methylbenzo[d]thiazol-2-amine

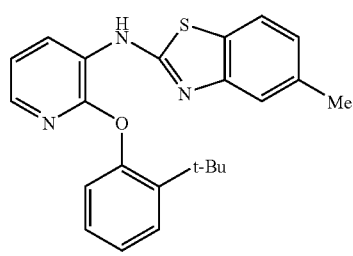

94

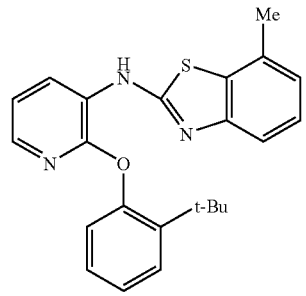

95

94a. 1-(2-(2-tert-Butylphenoxy)pyridin-3-yl)-3-m-tolylthiourea

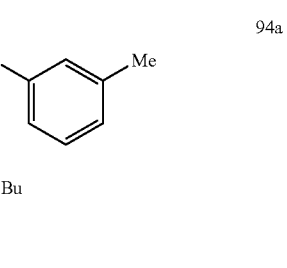

94a

To a solution of 3-amino toluene (8 mg, 0.075 mmol) in DCE (2 mL) was slowly added 1c (20 mg, 0.07 mmol). The reaction was stirred 48 h at rt and concentrated. The crude mixture was dissolved in methanol and filtered through an SCX cartridge. The material obtained containing mainly 94a was carried to the next step without further purification. $[M+H]^+=392.34$.

Examples 94 and 95

The crude reaction mixture from 94a was treated with thionyl chloride (0.5 mL) and the mixture was heated at 50° overnight. The mixture was concentrated and purified by preparative HPLC (continuous gradient from 40% B to 100% B; A=90:10:0.1 $H_2O$:MeOH:TFA; B=90:10:0.1 MeOH:$H_2O$:TFA) to afford Example 94 (7 mg, 25% yield) as a white powder; ($[M+H]^+=390.39$. $^1$H NMR (400 MHz, $CD_3OD$) δ ppm 1.32 (s, 9H), 2.42 (s, 3H), 6.95 (d, J=7.83 Hz, 1H), 7.06 (d, J=8.08 Hz, 1H), 7.15 (m, 2H), 7.21 (m, 1H), 7.45 (m, 2H), 7.58 (d, J=8.08 Hz, 1H), 7.82 (dd, J=4.80, 1.52 Hz, 1H), 8.68 (dd, J=7.83, 1.52 Hz, 1H)); and Example 95 (5 mg, 18% yield) also as a white powder; ($[M+H]^+=390.39$. $^1$H NMR (400 MHz, $CD_3OD$) δ ppm 1.33 (d, J=5.56 Hz, 9H), 2.46 (s, 3H), 6.95 (d, J=7.83 Hz, 1H), 7.03 (d, J=7.33 Hz, 1H), 7.15 (m, 2H), 7.22 (m, 1H), 7.28 (t, J=7.83 Hz, 1H), 7.45 (t, J=6.69 Hz, 2H), 8.73 (dd, J=7.96, 1.64 Hz, 1H)).

Example 96

6-tert-Butyl-N-(2-(2-tert-butyl-phenoxy)pyridin-3-yl)benzo[d]thiazol-2-amine

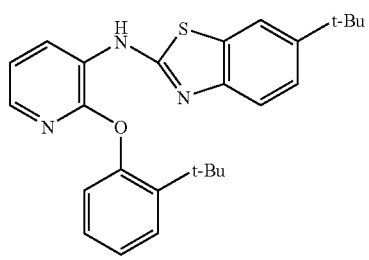

96

96a. 1-(2-(2-tert-Butylphenoxy)pyridin-3-yl)-3-(4-tert-butylphenyl)thiourea

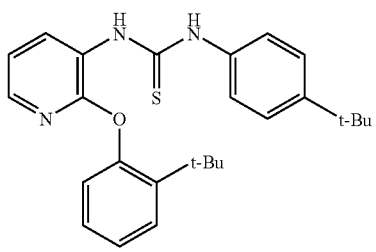

96a

To a solution of 4-tert-butyl aniline (30 mg, 0.20 mmol) in DCE (2 mL) was slowly added 1c (50 mg, 0.17 mmol). The reaction was stirred 48 h at rt and concentrated. 96a was crystallized from methanol to afford 40 mg (52% yield) of white crystals. [M+H]$^+$=434.04.

Example 96

Compound 96a (20 mg, 0.046 mmol) was treated with thionyl chloride (1 mL) overnight at 60° C. The mixture was concentrated and the residue was purified by preparative HPLC (continuous gradient from 40% B to 100% B; A=90:10:0.1 H$_2$O:MeOH:TFA; B=90:10:0.1 MeOH:H$_2$O:TFA) to afford Example 96 (8.5 mg, 41% yield) as a white powder. [M+H]$^+$=432.01.

Examples 97 and 98

5-tert-Butyl-N-(2-(2-tert-butylphenoxy)pyridin-3-yl)benzo[d]thiazol-2-amine and 7-tert-Butyl-N-(2-(2-tert-butylphenoxy)pyridin-3-yl)benzo[d]thiazol-2-amine

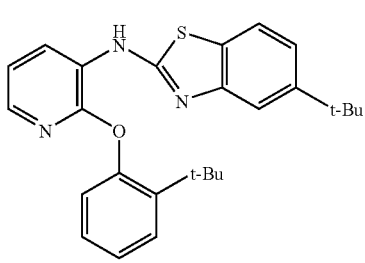

97

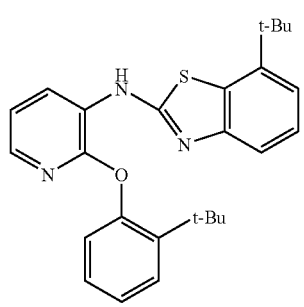

98

97a. 1-(2-(2-tert-Butylphenoxy)pyridin-3-yl)-3-(3-tert-butylphenyl)thiourea

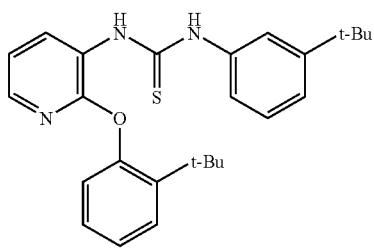

97a

To a solution of 3-tert-butylaniline (104 mg, 0.70 mmol) in DCE (3 mL) was slowly added 1c (100 mg, 0.35 mmol). The reaction was stirred 18 h at rt and concentrated. The crude mixture was dissolved in methanol and filtered through an SCX cartridge and concentrated to afford 97a (158 mg, quantitative) as a yellow oil. This material was carried to the next step without further purification.

Examples 97 and 98

The crude reaction mixture from 97a (158 mg, 0.36 mmol) was treated with thionyl chloride (5.0 mL) and the mixture was heated at 50° C. overnight. The mixture was concentrated and purified by column chromatography on silica gel using a stepwise gradient from 0% to 10% ethyl acetate in Hexanes as eluent. The fractions containing Examples 97 and 98 were further purified by preparative HPLC (continuous gradient from 60% B to 100% B; A=90:10:0.1 H$_2$O:MeOH:TFA; B=90:10:0.1 MeOH:H$_2$:TFA) to afford Example 97 (5 mg, 3% yield) as a white powder; ([M+H]$^+$=432.18. $^1$H NMR (400 MHz, CD$_3$OD) δ ppm 1.35 (s, 9H) 1.38 (s, 9H) 6.94 (d, J=8.25 Hz, 1H) 7.15 (m, 2H) 7.22 (t, J=7.70 Hz, 1H) 7.28 (d, J=8.25 Hz, 1H) 7.47 (d, J=8.25 Hz, 1H) 7.60 (d, J=8.25 Hz, 1H) 7.67 (s, 1H) 7.73 (d, J=4.95 Hz, 1H) 8.86 (d, J=7.70 Hz, 1H)); and Example 98 (2.3 mg, 2% yield) also as a white powder; ([M+H]$^+$=432.12. $^1$H NMR (400 MHz, CD$_3$OD) δ ppm 1.35 (m, 9H) 1.47 (m, 9H) 6.95 (d, J=8.25 Hz, 1H) 7.18 (m, 4H) 7.30 (t, J=7.70 Hz, 1H) 7.47 (d, J=7.70 Hz, 1H) 7.50 (d, J=7.70 Hz, 1H) 7.73 (d, J=4.40 Hz, 1H) 8.86 (d, J=7.70 Hz, 1H)).

Example 99

N-(2-(2-tert-Butylphenoxy)pyridin-3-yl)-6-(trifluoromethyl)benzo[d]thiazol-2-amine

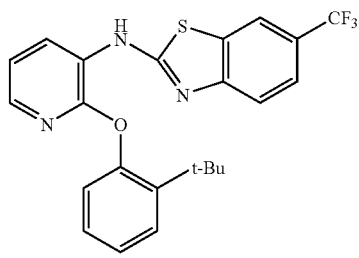

99

99a. 1-(2-(2-tert-Butylphenoxy)pyridin-3-yl)-3-(4-(trifluoromethyl)phenyl)thiourea

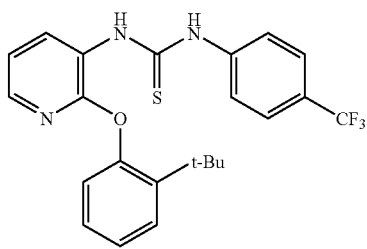

99a

To a solution of 4-trifluoromethylaniline (13 mg, 0.081 mmol) in DCE (0.5 mL) was slowly added 1e (20 mg, 0.07 mmol). The reaction was stirred 48 h at rt and concentrated. The crude mixture was dissolved in methanol and filtered through an SCX cartridge. The material obtained containing mainly 99a was carried to the next step without further purification. [M+H]$^+$=445.96.

Example 99

Half of the crude mixture from 99a was treated with thionyl chloride (0.2 ml) overnight at 60° C. The mixture was concentrated and the residue was and purified twice by preparative HPLC (continuous gradient from 40% B to 100%, then continuous gradient from 60% B to 100%, B; A=90:10:0.1 H$_2$O:MeOH:TFA; B=90:10:0.1 MeOH:H$_2$O:TFA) to afford Example 99 (1 mg, 6% yield) as a white powder. [M+H]$^+$=444.10.

Example 100

N-(2-(2-tert-Butylphenoxy)pyridin-3-yl)-6-(trifluoromethoxy)benzo[d]thiazol-2-amine

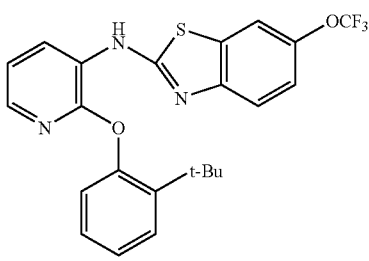

100

100a. 1-(2-(2-tert-Butylphenoxy)pyridin-3-yl)-3-(4-(trifluoromethoxy)phenyl)thiourea

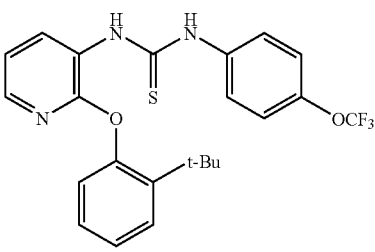

100a

To a solution of 4-trifluoromethoxyaniline (15 mg, 0.081 mmol) in DCE (0.5 mL) was slowly added 1c (20 mg, 0.07 mmol). The reaction was stirred 48 h at rt and concentrated. The crude mixture was dissolved in methanol and filtered through an SCX cartridge. The material obtained containing mainly 100a was carried to the next step without further purification. [M+H]$^+$=461.98.

Example 100

Half of the crude mixture from 100a was treated with thionyl chloride (0.2 ml) overnight at 60° C. The mixture was concentrated and the residue was purified by preparative HPLC (continuous gradient from 40% B to 100%, B; A=90:10:0.1 H$_2$O:MeOH:TFA; B=90:10:0.1 MeOH:H$_2$O:TFA) to afford Example 100 (2.1 mg, 15% yield) as a white powder. [M+H]$^+$=459.98.

Example 101

N-(2-(2-tert-Butylphenoxy)pyridin-3-yl)-6-phenyl-benzo[d]thiazol-2-amine

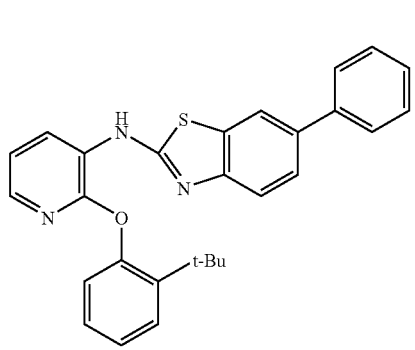

101a. 1-(2-(2-tert-Butylphenoxy)pyridin-3-yl)-3-(4-biphenyl)thiourea

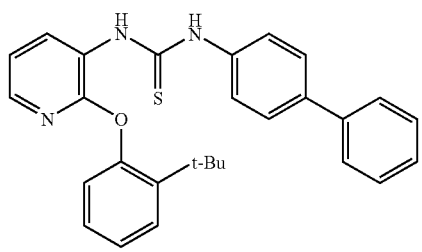

To a solution of 4-biphenylaniline (14 mg, 0.081 mmol) in DCE (0.5 mL) was slowly added 1c (20 mg, 0.07 mmol). The reaction was stirred 48 h at rt and concentrated. 101a was crystallized from methanol. [M+H]$^+$=454.02.

Example 101

Half of the crystals from 101a were treated with thionyl chloride (0.2 mL) overnight at 60° C. The mixture was concentrated and the residue was and purified by preparative HPLC (continuous gradient from 40% B to 100%, B; A=90:10:0.1 H$_2$O:MeOH:TFA; B=90:10:0.1 MeOH:H$_2$O:TFA) to afford Example 101 (6 mg, 38% yield over 2 steps) as a white powder. [M+H]$^+$=452.01.

Example 102

N-(2-(2-tert-Butylphenoxy)pyridin-3-yl)naphtho[1,2-d]thiazol-2-amine

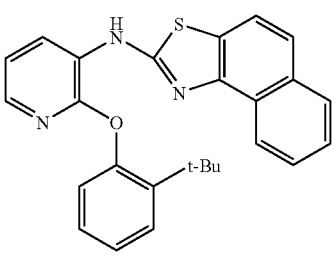

102a. 1-(2-(2-tert-Butylphenoxy)pyridin-3-yl)-3-(naphthalen-1-yl)thiourea

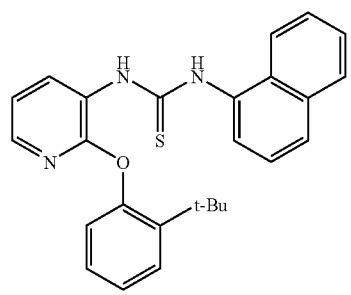

A solution of 1b (40 mg, 0.17 mmol) and 1-naphtylisothiocyanate (34 mg, 0.18 mmol) in dioxane (2 mL) was heated at 60° C. for 6 h. More 1-naphtylisothiocyanate (34 mg, 0.18 mmol) was added and the mixture was heated at 60° C. for 8 days. The mixture was concentrated and the residue was purified by column chromatography on silica gel using a continuous gradient from 0% to 40% ethyl acetate in hexanes as eluent to afford 102a which was directly used in the next step. [M−H]$^-$=426.18.

Example 102

Half of the material obtained in 102a was treated with thionyl chloride (0.5 mL) at rt for 5 h. The mixture was concentrated and the residue was triturated in methanol to afford Example 102 (1 mg, 3% yield over 2 steps) as a white powder. [M+H]$^+$=426.11.

Example 103

N-(2-(2-tert-Butylphenoxy)pyridin-3-yl)-4,6-dimethylbenzo[d]thiazol-2-amine

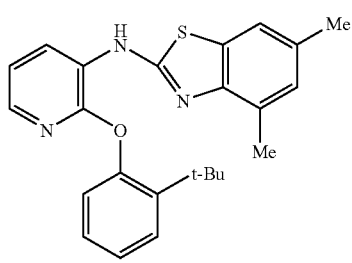

103a. 1-(2-(2-tert-Butylphenoxy)pyridin-3-yl)-3-(2,4-dimethylphenyl)thiourea

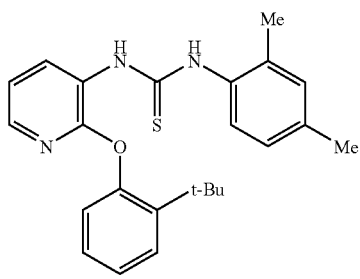

A solution of 1b (40 mg, 0.17 mmol) and 2,5-dimethylphenylisothiocyanate (30 mg, 0.18 mmol) in dioxane (2 mL) was heated at 60° C. for 6 h. More 2,5-dimethylphenylisothiocyanate (30 mg, 0.18 mmol) was added and the mixture was heated at 60° C. for 8 days. The mixture was concentrated and the residue was purified by column chromatography on silica gel using a continuous gradient from 0% to 40% ethyl acetate in hexanes as eluent. Half of the material was carried to the next step without further purification, the other half was purified by preparative HPLC (continuous gradient from 40% B to 100%, B; A=90:10:0.1 H$_2$O:MeOH:TFA; B=90:10:0.1 MeOH:H$_2$O:TFA) to afford 103a (6 mg, 36%). [M+H]$^+$=406.16.

Example 103

Half of the material obtained in 103a was treated with thionyl chloride (0.5 mL) at rt for 5 h. The mixture was concentrated and the residue was purified by preparative HPLC (continuous gradient from 50% B to 100%, B; A=90:10:0.1 H$_2$O:MeOH:TFA; B=90:10:0.1 MeOH:H$_2$O:TFA) to afford Example 103 (3 mg, 10% yield over two steps) as a white powder. [M+H]$^+$=404.10.

Example 104

N-(2-(2-tert-Butylphenoxy)pyridin-3-yl)-4,6-dichlorobenzo[d]thiazol-2-amine

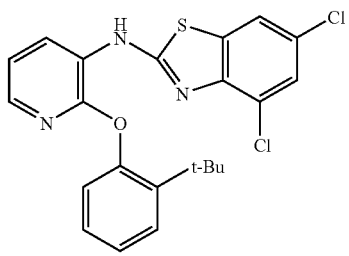

104a. 1-(2-(2-tert-Butylphenoxy)pyridin-3-yl)-3-(2,4-dichlorophenyl)thiourea

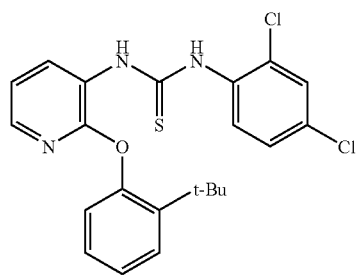

A solution of 1b (40 mg, 0.17 mmol) and 2,5-dichlorophenylisothiocyanate (37 mg, 0.18 mmol) in dioxane (2 mL) was heated at 60° C. for 6 h. More 2,5-dichlorophenylisothiocyanate (37 mg, 0.18 mmol) was added and the mixture was heated at 60° C. for 8 days. The mixture was concentrated and the residue was purified by column chromatography on silica gel using a continuous gradient from 0% to 40% ethyl acetate in hexanes as eluent. Half of the material was carried to the next step without further purification, the other half was purified by preparative HPLC (continuous gradient from 40% B to 100%, B; A=90:10:0.1 H$_2$O:MeOH:TFA; B=90:10:0.1 MeOH:H$_2$O:TFA) to afford 104a (8 mg, 43%). $^1$H NMR (400 MHz, CD$_3$OD) δ ppm 1.38 (m, 9H), 6.93 (dd, J=7.83, 1.52 Hz, 1H), 7.15 (m, 3H), 7.31 (dd, J=8.59, 2.27 Hz, 1H), 7.44 (dd, J=7.83, 1.77 Hz, 1H), 7.52 (d, J=2.53 Hz, 1H), 7.68 (d, J=8.59 Hz, 1H), 7.90 (dd, J=5.05, 1.77 Hz, 1H), 8.35 (dd, J=7.71, 1.89 Hz, 1H).

Example 104

Half of the material obtained in 104a was treated with thionyl chloride (0.5 mL) at rt for 5 h. The mixture was concentrated and the residue was purified by preparative HPLC (continuous gradient from 50% B to 100%, B; A=90:10:0.1 H$_2$O:MeOH:TFA; B=90:10:0.1 MeOH:H$_2$O:TFA) to afford Example 104 (3 mg, 10% yield over two steps) as a white powder. [M+H]$^+$=443.96.

Example 105

N-(2-(2-tert-Butylphenoxy)pyridin-3-yl)-4-methyl-6-(trifluoromethoxy)benzo[d]thiazol-2-amine

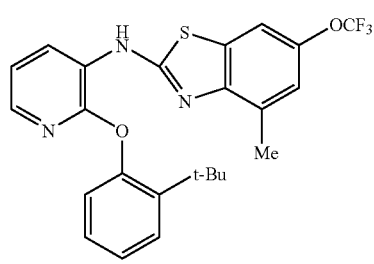

105

105a. 1-(2-(2-tert-Butylphenoxy)pyridin-3-yl)-3-(2-methyl-4-(trifluoromethoxy)phenyl)thiourea

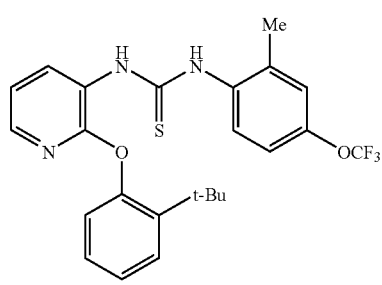

105a

To a solution of 4-trifluoromethoxy-1-methyl-aniline (32 mg, 0.17 mmol) in THF (1 mL) was slowly added 1c (40 mg, 0.14 mmol). The reaction was stirred 18 h at 60° C. and concentrated. The residue was purified by column chromatography on silica gel using a continuous gradient from 0% to 40% ethyl acetate in hexanes as eluent to afford 105a (36 mg, 45%). [M+H]$^+$=476.08.

Example 105

Compound 105a (30 mg, 0.06 mmol) was treated with thionyl chloride (0.5 ml) 2 days at rt. The mixture was concentrated and the residue was purified by preparative HPLC (continuous gradient from 40% B to 100%, B; A=90:10:0.1 H$_2$O:MeOH:TFA; B=90:10:0.1 MeOH:H$_2$O:TFA) to afford Example 105 (25 mg, 83% yield) as a white powder. [M+H]$^+$= 474.06.

Example 106

3-(3-(6-tert-Butyl-1H-benzo[d]imidazol-2-ylamino)pyridin-2-yloxy)benzonitrile

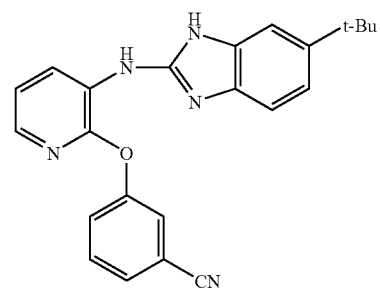

106

106a. 3-(3-Nitropyridin-2-yloxy)benzonitrile

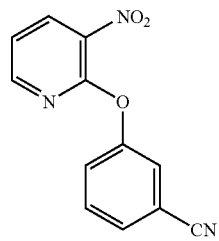

106a

3-Cyanophenol (187 mg, 1.06 mmol) was dissolved in DMF (1 mL) and cesium carbonate (360 mg, 1.1 mmol) was added followed by a solution of 2-chloro-3-nitropyridine (158 mg, 1.0 mmol) in DMF (1 mL). The reaction mixture was heated with shaking at 80° C. for 18 h. The mixture was concentrated. The residue was dissolved in ethyl acetate (4 mL) and washed with water (0.6 mL), saturated NaHCO$_3$ (0.5 mL) and water (2×0.5 mL). The organic phase was concentrated and the resulted mixture containing mainly 106a was used in the next step without further purification.

106b. 3-(3-Aminopyridin-2-yloxy)benzonitrile

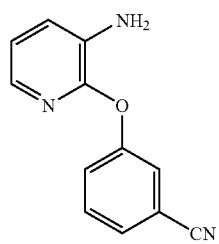

106b

The crude reaction mixture from 106a was dissolved in ethanol (4 mL) and ethyl acetate (1 mL). Zinc dust (1.3 g, 20 mmol) was added to the mixture along with ammonium chloride (300 mg, 5.7 mmol). The mixture was shaken at rt for 18 h. The reaction mixture was filtered over Celite®, and concentrated to afford mainly 106b which was used in the next step without further purification. [M+H]$^+$=212.32.

106c.
3-(3-Isothiocyanatopyridin-2-yloxy)benzonitrile

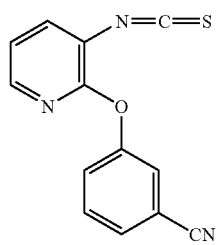

106c

A solution of the crude mixture from 106b (16.2 mg, 0.06 mmol) in DCM (1 ml) was added dropwise to a solution of N,N-thiocarbonyl diimidazole (21.3 mg, 0.12 mmol) in DCM (0.5 mL) at 0° C. The reaction mixture was shaken at 0° C. for 1 h, then at rt for 2 h. The mixture was concentrated. The residue was dissolved in DCM (0.5 mL) and passed through an SPE tube containing 2 g of silica. The product was eluted using 10-20% ethyl acetate in hexane and, after concentration, was used in the next step without any further purification.

Example 106

The crude mixture from 106c (0.06 mmol) was dissolved in DCE (0.5 mL) and a solution of 4-(tert-butyl)-1,2-diaminobenzene (20 mg, 0.12 mmol) in DCE (0.5 mL) was added. The mixture was shaken at rt for 6 h, then a solution of EDC (23 mg, 0.12 mmol) in DCM (0.5 mL) was added and the mixture was shaken 18 h at rt. Another solution of EDC (23 mg, 0.12 mmol) in DCM (0.5 mL) was added and the mixture was shaken at rt for another 5 h. The mixture was concentrated and purified by preparative HPLC (continuous gradient from 40% B to 101%, B; A=90:10:0.1 H$_2$O:MeOH:TFA; B=90:10:0.1 MeOH:H$_2$O-TFA) to afford Example 106 (8.2 mg, 35% yield over 4 steps) as a white powder. [M+H]$^+$= 384.09.

Examples 107 to 122

Examples 107 to 122 listed in Tables 3 below were prepared in an identical manner to Example 106 above. The corresponding phenol (1.06 mmol) was dissolved in DMF (1 mL) and cesium carbonate (360 mg, 1.11 mmol) was added followed by a solution of 2-chloro-3-nitropyridine (158 mg, 1.0 mmol) in DMF. The reaction mixture was heated with shaking at 80° C. for 18 h. The mixture was concentrated. The residue was dissolved in ethyl acetate (4 mL) and washed with water (0.6 mL), saturated NaHCO$_3$ (0.5 mL) and water (2×0.5 ml). The organic phase was concentrated and the resulting mixture was dissolved in ethanol (4 mL) and ethyl acetate (1 mL). Zinc dust (1.3 g, 20 mmol) was added to the mixture along with ammonium chloride (300 mg, 5.7 mmol). The mixture was shaken at rt for 18 h. The reaction mixture was filtered over Celite®, and concentrated to afford mainly the corresponding aniline which was used in the next step without further purification.

A solution of the crude aniline obtained (0.06 mmol) in DCM (1 mL) was added dropwise to a solution of N,N-thiocarbonyl diimidazole (21.3 mg, 0.12 mmol) in DCM (0.5 mL) at 0° C. The reaction mixture was shaken at 0° C. for 1 h, then at rt for 2 h. The mixture was concentrated. The residue was dissolved in DCM (0.5 ml) and passed through an SPE tube containing 2 g of silica. The product was eluted using 10-20% ethyl acetate in hexane and was concentrated. The residue obtained was dissolved in DCE (0.5 mL) and a solution of 4-(tert-butyl)-1,2-diaminobenzene (20 mg, 0.12 mmol) in DCE (0.5 mL) was added. The mixture was shaken at rt for 6 h, then a solution of EDC (23 mg, 0.12 mmol) in DCM (0.5 mL) was added and the mixture was shaken 18 h at rt. Another solution of EDC (23 mg, 0.12 mmol) in DCM (0.5 mL) was added and the mixture was shaken at rt for another 5 h. The mixture was concentrated and purified by preparative HPLC (continuous gradient from 40% B to 100%, B; A=90:10:0.1 H$_2$O:MeOH:TFA; B=90:10:0.1 MeOH:H$_2$O:TFA) to afford the desired compound in 10-60% yield.

TABLE 3

| Ex. No. | R$^5$ | MS (M + 1) |
|---|---|---|
| 107 | 3-OCF$_3$-phenyl | 443.09 |
| 108 | 3-Et-phenyl | 387.13 |
| 109 | 3-Ph-phenyl | 435.14 |
| 110 | 3-Cl-phenyl | 393.06 |
| 111 | 3-F-phenyl | 377.06 |
| 112 | 2-Cl-phenyl | 393.05 |
| 113 | 3-Br-phenyl | 436.98 |
| 114 | 3,5-diCF$_3$-phenyl | 495.09 |
| 115 | 2-Cl-5-CF$_3$-phenyl | 461.06 |
| 116 | 2,3-diCl-phenyl | 427.05 |
| 117 | 2,5-diCl-phenyl | 427.03 |
| 118 | 3,5-diCl-phenyl | 427.01 |
| 119 | 2-F-3-CF$_3$-phenyl | 445.03 |
| 120 | 2-F-5-CF$_3$-phenyl | 445.07 |
| 121 | phenyl | 359.06 |
| 122 | 2-CF$_3$-phenyl | 427.09 |

Example 123

Methyl 5-(6-tert-butyl-1H-benzo[d]imidazol-2-ylamino)-6-(2-tert-butylphenoxy)picolinate

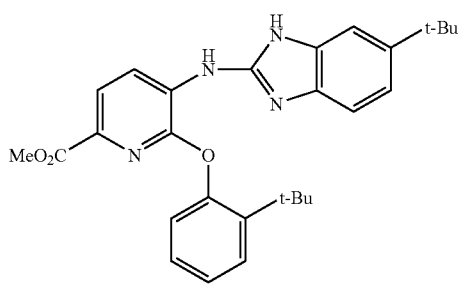

123a. 6-Bromo-2-(2-tert-butylphenoxy)pyridin-3-amine

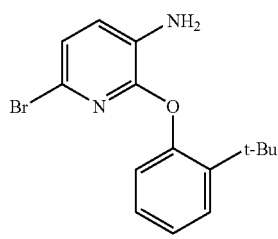

A solution of N-bromosuccinimide (2.32 g, 13.0 mmol) in DMF (20 ml) was added to a cold (−20° C.) solution of 1b (2.76 g, 11.4 mmol) in DMF (25 ml). The reaction rapidly turned dark red. HPLC analysis after 5 min showed that the reaction was complete. The reaction was quenched with a freshly prepared solution of sodium thiosulfate (40 ml, 10% aqueous). A precipitate formed. The mixture was warmed to rt and was diluted with water (60 ml). The solid was filtered, washed with water and dried overnight under reduced pressure to give 123a (3.82 g, 96% yield) as brown solid. [M+H]$^+$=321.14. $^1$H NMR (500 MHz, CDCl$_3$) δ ppm 1.40 (s, 9H), 3.91 (s, 2H), 6.93 (m, 2H), 7.00 (d, J=8.07 Hz, 1H), 7.12 (t, J=7.73 Hz, 1H), 7.20 (t, J=7.73 Hz, 1H), 7.41 (d, J=8.07 Hz, 1H).

123b. 6-Cyano-2-(2-tert-butylphenoxy)pyridin-3-amine

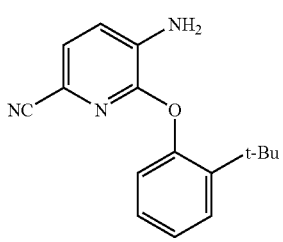

A mixture of 123a (1000 mg, 3.1 mmol), copper cyanide (1120 mg, 12.5 mmol), tris(dibenzylideneacetone)dipalladium(0) (114 mg, 0.12 mmol), 1,1'-Bis (diphenylphosphino) ferrocene (276 mg, 0.5 mmol) and tetraethylammonium cyanide (486 mg, 3.1 mmol) in dioxane (16 ml) was heated at 105° C. for 4.5 h. The reaction was completed as determined by TLC (30% ethyl acetate in heptane). The mixture was cooled to rt, diluted with ether (50 ml) filtered over Celite® and concentrated to give 1.3476 g of yellow foam. The foam was recrystallized from 30% ethyl acetate in heptane to give 123b (753.6 mg, 91% yield) as a brown powder. [M+H]$^+$=268.13. $^1$H NMR (500 MHz, CDCl$_3$) δ ppm 1.36 (s, 9H), 4.53 (s, 2H), 6.96 (dd, J=7.97, 4.12 Hz, 2H), 7.17 (t, J=7.42 Hz, 1H), 7.24 (m, 2H), 7.44 (d, J=7.70 Hz, 1H).

123c. Methyl 5-Amino-6-(2-tert-butylphenoxy)picolinate and 5-Amino-6-(2-tert-butylphenoxy)-picolinamide

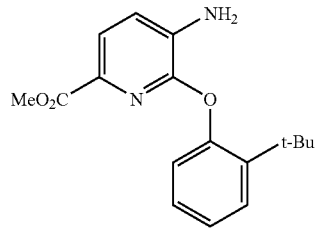

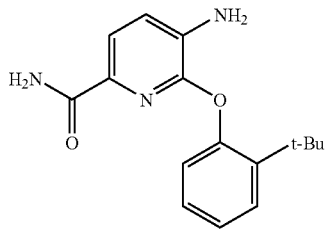

Sodium hydroxide (225 mg, 5.62 mmol) was dissolved in ethanol/water (1:1 500 μL) and 123b (150 mg, 0.56 mmol) was added. The mixture was microwaved at 185° C. for 10 min. HPLC analysis showed that the reaction was completed. Water (3 mL) was added and the mixture was extracted with ethyl acetate (3×5 mL). Some of the acid was also extracted. The aqueous layer was acidified with acetic acid and was extracted with ethyl acetate (3×5 mL). The organic layer were combined and washed with brine, dried with magnesium sulfate, filtered and concentrated to give 155.1 mg of yellow solid.

Trimethylsilyl diazomethane (2M in dichloromethane, 1100 μL, 2.2 mmol) was added to the mixture of acid and amide in methanol (3 mL), the mixture was stirred for 1 h. The reaction did not appear to go completion even after adding excess reagent (the amide and the acid had the same retention time by HPLC). TLC analysis showed the starting material to be a mixture of the amide and the acid. The sample was concentrated and was purified by flash chromatography (eluting with heptane to 70% ethyl acetate in heptane) to give 123c as a white solid (69.3 mg, 44% yield); ([M+H]$^+$=301.26. $^1$H NMR (500 MHz, CDCl$_3$) δ ppm 1.42 (s, 9H); 3.81 (s, 3H); 4.35 (s, 2H); 7.01 (dd, J=8.06, 1.35 Hz, 1H); 7.04 (d, J=8.07 Hz, 1H); 7.11 (d, J=7.39 Hz, 1H); 7.19 (d, J=38.07 Hz, 1H); 7.42 (dd, J=8.07, 1.34 Hz, 1H); 7.77 (d, J=8.07 Hz, 1H)); and 123c' (54 mg, 36%); ([M+H]$^+$=286.21. $^1$H NMR (500 MHz, CDCl$_3$) δ ppm 1.37 (s, 9H); 4.39 (s, 2H); 5.51 (s, 1H); 6.98 (d, J=6.72 Hz, 1H); 6.99 (s, 1H); 7.09 (d, J=7.39 Hz, 1H); 7.15 (t, J=7.73 Hz, 1H); 7.21 (td, J=7.56, 1.68 Hz, 1H); 7.45 (dd, J=8.07, 1.34 Hz, 1H); 7.76 (d, J=8.07 Hz, 1H)).

Example 123

A solution of the aniline 123c (18 mg, 0.06 mmol) in DCM (1 mL) was added dropwise to a solution of N,N-thiocarbonyl diimidazole (21.3 mg, 0.12 mmol) in DCM (0.5 mL) at 0° C. The reaction mixture was shaken at 0° C. for 1 h, then at rt for 2 h. The mixture was concentrated. The residue was dissolved in DCM (0.5 mL) and passed through an SPE tube containing 2 g of silica. The product was eluted using 10-20% ethyl acetate in hexane and was concentrated. The residue obtained was dissolved in DCE (0.5 mL) and a solution of 4-(tert-butyl)-1,2-diaminobenzene (20 mg, 0.12 mmol) in DCE (0.5 mL) was added. The mixture was shaken at rt for 6 h, then a solution of EDC (23 mg, 0.12 mmol) in DCM (0.5 mL) was added and the mixture was shaken 18 h at rt. Another solution of EDC (23 mg, 0.12 mmol) in DCM (0.5 mL) was added and the mixture was shaken at rt for another 5 h. The mixture was concentrated and purified by preparative HPLC (continuous gradient from 40% B to 100%, B; A=90:10:0.1 H$_2$O:MeOH:TFA; B=90:10:0.1 MeOH:H$_2$O:TFA) to afford Example 123 (1.7 mg, 3% yield) as a colorless oil. [M+H]$^+$=473.15.

Example 124

5-(6-tert-Butyl-1H-benzo[d]imidazol-2-ylamino)-6-(2-tert-butylphenoxy)picolinamide

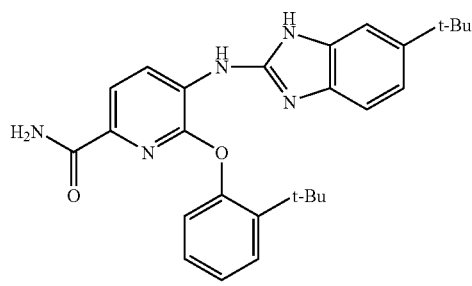

A solution of the aniline 123c' (17 mg, 0.06 mmol) in DCM (1 mL) was added dropwise to a solution of N,N-thiocarbonyl diimidazole (21.3 mg, 0.12 mmol) in DCM (0.5 mL) at 0° C. The reaction mixture was shaken at 0° C. for 1 h, then at rt for 2 h. The mixture was concentrated. The residue was dissolved in DCM (0.5 mL) and passed through an SPE tube containing 2 g of silica. The product was eluted using 10-20% ethyl acetate in hexane and was concentrated. The residue obtained was dissolved in DCE (0.5 mL) and a solution of 4-(tert-butyl)-1,2-diaminobenzene (20 mg, 0.12 mmol) in ACE (0.5 mL) was added. The mixture was shaken at rt for 6 h, then a solution of EDC (23 mg, 0.12 mmol) in DCM (0.5 mL) was added and the mixture was shaken 18 h at rt. Another solution of EDC (23 mg, 0.12 mmol) in DCM (0.5 mL) was added and the mixture was shaken at rt for another 5 h. The mixture was concentrated and purified by preparative HPLC (continuous gradient from 40% B to 100%, B; A=90:10:0.1 H$_2$O:MeOH: TFA; B=90:10:0.1 MeOH:H$_2$O:TFA) to afford Example 124 (1.3 mg, 3% yield) as a colorless oil. [M+H]$^+$=458.15.

Example 125

6-tert-Butyl-N-(2-(2-tert-butylphenoxy)-6-chloropyridin-3-yl)-1H-benzo[d]imidazol-2-amine

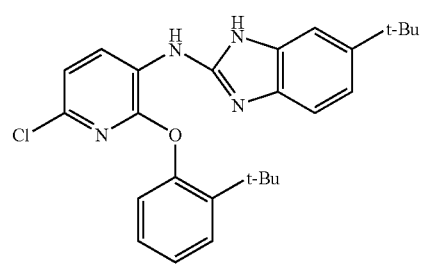

125a. 2-(2-tert-Butyl-phenoxy)-6-chloro-pyridin-3-ylamine

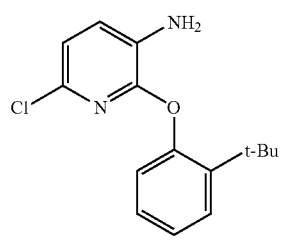

A solution of N-chlorosuccinimide (556 mg, 4.2 mmol) in DMF (10 ml) was added to a solution of 1b (960 mg, 4.0 mmol) in DMF (15 ml) at rt. The reaction was heated at 40° C. for 30 min. The reaction mixture was cooled to rt and the reaction was quenched with saturated aqueous sodium thiosulfate (Na$_2$S$_2$O$_3$) solution (100 mL). The mixture was extracted with ethyl acetate (3×20 ml) and the organic layers were washed with aqueous sodium thiosulfate solution, brine and were dried over sodium sulfate. The solvents were removed under reduced pressure and the dark red oil was purified by chromatography on silica (continuous gradient 0 to 40% Hexane/EtOAc) to give 125a as an off-white solid (746 mg, 68% yield). [M+H]$^+$=277.11. $^1$H NMR (500 MHz, CDCl$_3$): 7.41 (d, 1H, J=7.4 Hz), 7.20 (t 1H, J=7.4 Hz), 7.11 (t, 1H, J=7.4 Hz), 7.01 (d, 1H, J=8.1 Hz), 6.93 (d, 1H, J=8.1 Hz), 6.85 (d, 1H, J=8.1 Hz), 3.91 (s, 1H), 1.39 (s, 9H).

Example 125

A solution of 125a (20 mg, 0.07 mmol) in DCM (0.5 mL) was added to a solution of N,N-thiocarbonyl diimidazole (26.0 mg, 0.13 mmol) in DCM (0.5 mL) at 0° C. The mixture was allowed to rt. After 5 h, more N,N-thiocarbonyl diimidazole (26.0 mg, 0.13 mmol) was added and the mixture was heated at 50° C. for 18 h. The reaction mixture was split into two equal portions. Half of the reaction mixture was treated with 4-(tert-butyl)-1,2-diaminobenzene (26 mg, 0.16 mmol) for 5 days at rt. The mixture was concentrated and the residue was purified by prep-HPLC (continuous gradient from 40% B to 100%, B; A=90:10:0.1 H$_2$O:MeOH:TFA; B=90:10:0.1 MeOH:H$_2$O:TFA). The fractions containing the thiourea were concentrated and the residue was treated with a solution of EDC (23 mg, 0.12 mmol) in DCE (0.5 mL) for 18 h at rt. The mixture was concentrated and the residue was purified by prep-HPLC (continuous gradient from 40% B to 100%, B; A=90:10:0.1 H$_2$O:MeOH:TFA; B=90:10:0.1 MeOH:H$_2$O:TFA) to afford Example 125 (2.5 mg, 16% yield) as a white powder. [M+H]$^+$=449.02.

Example 126

N2-(2-(2-tert-Butylphenoxy)pyridin-3-yl)-5-methyl-3H-benzo[d]imidazole-2,4-diamine

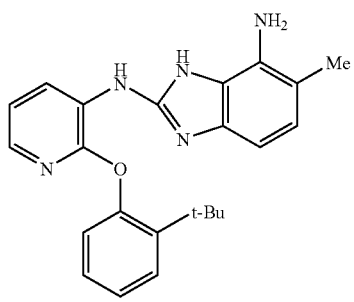

126

Example 5 (10.1 mg, 0.019 mmol) was dissolved into ethanol (2-0 ml). Palladium on charcoal (10%, 4.5 mg) was added and the mixture was stirred for 4 h under hydrogen atmosphere. The reaction mixture was filtered over Celite® and concentrated to afford 9.7 mg of a dark blue oil as crude product. This oil was purified by preparative HPLC (continuous gradient from 20% B to 100% B; A=90:10:0.1 H$_2$O:CH$_3$CN:TFA; B=90:10:0.1 CH$_3$CN:H$_2$O:TFA) to afford Example 126 (4.4 mg, 46% yield) as a colorless oil. [M+H]$^+$=388.11.

Example 127

N-(2-(2-tert-Butylphenoxy)pyridin-3-yl)-1H-benzo[d]imidazol-2-amine

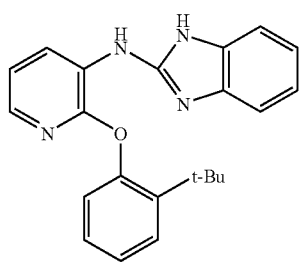

127

To a solution of o-phenylenediamine (15.2 mg, 0.1406 mmol) in DCE (1.0 ml) was added 1c (20 mg, 0.0703 mmol). The reaction was stirred overnight at rt. EDC (27 mg, 0.1406 mmol) was added and the reaction was again stirred overnight at rt. The mixture was concentrated and purified by preparative HPLC (continuous gradient from 20% B to 100% B; A=90:10:0.1 H$_2$O:CH$_3$CN:TFA; B=90:10:0.1 CH$_3$CN:H$_2$O:TFA) to afford Example 127 (25 mg, 75% yield) as a white solid. [M+H]$^+$=359.05.

Example 128

N-(2-(2-tert-Butylphenoxy)pyridin-3-yl)-1H-imidazo[4,5-b]pyridin-2-amine

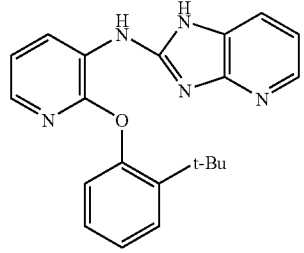

128

To a solution of 2,3-diaminopyridine (15.3 mg, 0.1406 mmol) in DCE (1.0 ml) was added 1c (20 mg, 0.0703 mmol). The reaction was stirred overnight at rt. EDC (27 mg, 0.1406 mmol) was added and the reaction was again stirred overnight at rt. The mixture was concentrated and purified by preparative HPLC (continuous gradient from 20% B to 100% B; A=90:10:0.1 H$_2$O:CH$_3$CN:TFA; B=90:10:0.1 CH$_3$CN:H$_2$O:TFA) to afford Example 128 (11.3 mg, 34% yield) as an off-white solid. [M+]$^+$=360.09.

Examples 129 to 132

Examples 129 to 132 depicted in Table 4 were prepared using the synthesis methods described as above, and the reaction of the appropriated derivatives.

TABLE 4

| Ex. No. | | MS (M + 1) |
|---|---|---|
| 129 | 5,6-dichloro-2-methyl-1H-benzimidazole | 461 |

TABLE 4-continued

| Ex. No. | Structure (R¹, R², R³, R⁴) | MS (M + 1) |
|---|---|---|
| 130 | 2-methyl-5-morpholino-1H-benzimidazole | 444 |
| 131 | 2-methyl-1H-benzimidazole-4-carboxylic acid methyl ester (CO₂Me) | 417 |
| 132 | 2-methyl-N-methyl-1H-benzimidazol-5-amine (NMe) | 402 |

Example 133

6-tert-Butyl-N-(2-(2-(trifluoromethoxy)phenoxy)pyridin-3-yl)-1H-benzo[d]imidazol-2-amine

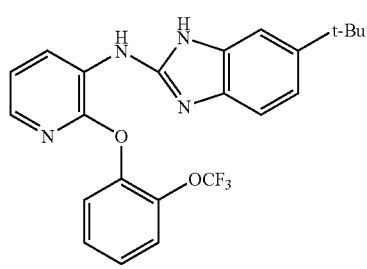

133a. 2-(2-(Trifluoromethoxy)phenoxy)pyridin-3-amine

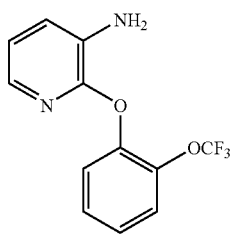

133a was prepared according to the procedure described in 1b. [M+H]+=271.

133b. 3-Isothiocyanato-2-(2-(trifluoromethoxy)phenoxy)pyridine

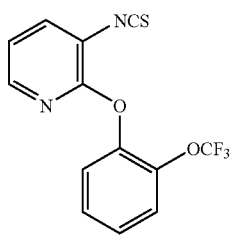

A solution of 133a (16.21 mg, 0.0600 mmol) in anhydrous DCM (1.0 ml) was added dropwise to a cold solution of thiocarbonyl diimidazole (21.39 mg, 0.1200 mmol) in anhydrous DCM (0.50 ml). The reaction was stirred at 0° C. for 1 h and then warmed to rt with stirring for 2 h. The mixture was concentrated down to afford crude 133b which was taken directly onto the next step without purification.

Example 133

To a solution of 133b (0.060 mmol) in DCE (1 mL) was added 4-(tert-butyl)-1,2-diaminobenzene (29.57 mg, 0.180 mmol). The reaction was stirred overnight at rt. EDC (92.04 mg, 0.480 mmol) was added and the reaction was again stirred overnight at rt. The mixture was concentrated and purified by preparative HPLC (continuous gradient from 20% B to 100% B; A=90:10:0.1 H$_2$:CH$_3$CN:TFA; B=90:10:0.1 CH$_3$CN:H$_2$O:TFA) to afford Example 133 (17.7 mg, 53% yield) as an orange solid. [M+H]⁺=443.12.

Example 134

6-tert-Butyl-N-(2-(2,2-dimethyl-2,3-dihydrobenzofuran-7-yloxy)pyridin-3-yl)-1H-benzo[d]imidazol-2-amine

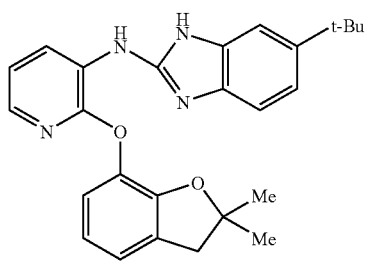

134

134a. 2-(2,2-Dimethyl-2,3-dihydrobenzofuran-7-yloxy)-3-nitropyridine

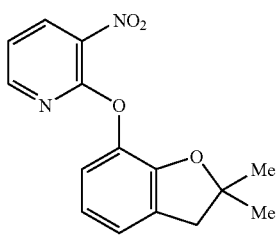

134a

A solution of 2-chloro-3-nitropyridine (4.9 g, 30.9 mmol) in DMF (50 mL) was treated with 2,2-dimethyl-2,3-dihydrobenzofuran-7-ol (5.3 mL, 46.4 mmol) and cesium carbonate (30.2 g, 92.7 mmol). The mixture was heated at 80° C. for 10 h. The reaction was cooled to rt, and the mixture was poured in water (200 mL) with stirring. The yellow precipitate formed was filtered and washed with water, and recrystallized from ethanol (50 mL) to afford 134a as brown crystals (6.5 g, 73% yield). [M+H]$^+$=287.16. $^1$H NMR (500 MHz, deuterochloroform) δ ppm 8.38 (dd, 1H, J=1.7 Hz, J=5.0 Hz), 8.31 (dd, 1H, J=5.0 Hz, J=1.7 Hz), 7.12 (dd, 1H, J=10.0 Hz, J=5.0 Hz), 7.05 (d, 1H, J=5.0 Hz), 7.00 (d, 1H, J=10.0 Hz), 6.86 (t, 1H, J=10.0 Hz), 3.05 (s, 2H), 1.39 (s, 6H); $^{13}$C (125 MHz, deuterochloroform) δ (ppm), 155.42, 151.76, 150.16, 136.03, 135.40, 134.04, 129.76, 122.60, 121.06, 120.37, 118.07, 88.40, 43.07, 27.98.

134b. 2-(2,2-Dimethyl-2,3-Dihydrobenzofuran-7-yloxy)pyridin-3-Amine

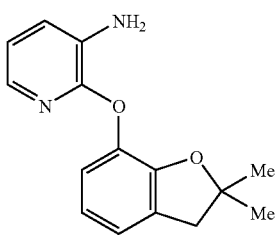

134b 134a (3.27 g, 11.4 mmol) was dissolved in a 1:1 mixture of methanol and ethyl acetate (80 mL). Palladium on charcoal (10%, 1.2 g, 1.1 mmol) was added, and the mixture was stirred 1 h under hydrogen atmosphere (40 psi). The reaction mixture was filtered over Celite® and concentrated to afford 2.78 g (97% yield, 100% pure) of 134b as an off-white solid. [M+H]$^+$=257.17; in NMR (500 MHz, deuterochloroform) δ ppm 7.53 (d, 1H, J=5.0 Hz), 6.97 (d, 2H, J=10.0 Hz), 6.95 (d, 1H, J=5.0 Hz), 6.80 (m, 2H), 3.97 (br, 2H), 3.05 (s, 2H), 1.44 (s, 6H); $^{13}$C (125 MHz, deuterochloroform) δ (ppm), 151.60, 150.18, 137.70, 135.60, 131.52, 129.47, 121.77, 121.30, 120.96, 120.27, 119.02, 87.80, 43.19, 28.08.

134c. 2-(2,2-Dimethyl-2,3-dihydrobenzofuran-7-yloxy)-3-isothiocyanatopyridine

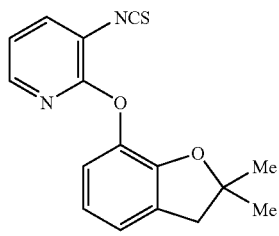

134c

A solution of 134b (15.38 mg, 0.0600 mmol) in anhydrous DCM (1.0 ml) was added dropwise to a cold solution of thiocarbonyl diimidazole (21.39 mg, 0.1200 mmol) in anhydrous DCM (0.50 ml). The reaction was stirred at 0° C. for 1 h and then warmed to rt with stirring for 2 h. The mixture was concentrated down to afford crude 134e which was taken directly onto the next step without purification.

Example 134

To a solution of 134c (0.060 mmol) in DCE (1 mL) was added 4-(tert-butyl)-1,2-diaminobenzene (29.57 mg, 0.180 mmol). The reaction was stirred overnight at rt. EDC (92.04 mg, 0.480 mmol) was added and the reaction was again stirred overnight at rt. The mixture was concentrated and purified by preparative HPLC (continuous gradient from 20% B to 100% B; A=90:10:0.1 H$_2$O; —CH$_3$CN:TFA; B=90:10: 0.1 CH$_3$CN:H$_2$O:TFA) to afford Example 134 (16.8 mg, 52% yield) as an orange solid. [M+H]$^+$=429.33.

Example 135

6-tert-Butyl-N-(2-(2-tert-butylphenoxy)phenyl)-1H-benzo[d]imidazol-2-amine

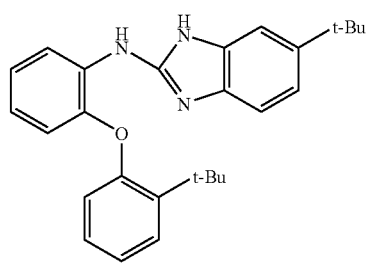

135

135a. 2-(2-tert-Butylphenoxy)benzenamine

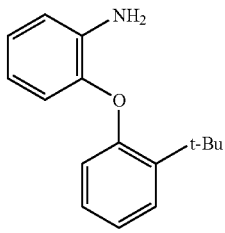

A mixture of 2-chloronitrobenzene (9.5 g, 60 mmol), 2-t-butyl phenol (9.04 g, 60.2 mmol) and potassium carbonate (10.6 g) in DMF was heated at 130° C. for 6 days. The reaction was cooled to rt and partitioned between diethyl ether (400 mL) and water (500 mL). The organic layer was separated and the aqueous layer was extracted with ether (3×100 mL). The combined organic layers were dried over magnesium sulfate, filtered and evaporated to give 1-tert-butyl-2-(2-nitrophenoxy)benzene (20 g). $[M+H]^+=216.23$.

To a solution of 1-tert-butyl-2-(2-nitrophenoxy)benzene (20 g, crude) in MeOH/THF (1:1, 200 mL) was added 10% Pd/C (2 g). The mixture was hydrogenated under 75 psi overnight. The mixture was filtered through Celite® cake and the filtrate was evaporated to give the crude product as a black oil. Purification by flash chromatography (0-30% EtOAc/hexane) provided 135a (11 g) as a brown solid.

135b. 1-tert-Butyl-2-(2-isothiocyanatophenoxy)benzene

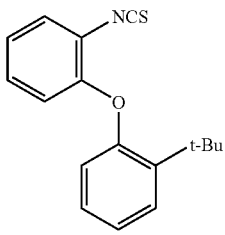

A solution of 135a (14.48 mg, 0.0600 mmol) in anhydrous DCM (1.0 ml) was added dropwise to a cold solution of thiocarbonyl diimidazole (21.39 mg, 0.1200 mmol) in anhydrous DCM (0.50 ml). The reaction was stirred at 0° C. for 1 h and then warmed to rt with stirring for 2 h. The mixture was concentrated down to afford crude 135b which was taken directly onto the next step without purification.

Example 135

To a solution of 135b (0.060 mmol) in DCE (1 mL) was added 4-(tert-butyl)-1,2-diaminobenzene (29.57 mg, 0.180 mmol). The reaction was stirred overnight at rt. EDC (92.04 mg, 0.480 mmol) was added and the reaction was again stirred overnight at rt. The mixture was concentrated and purified by preparative HPLC (continuous gradient from 20% B to 100% B; A=90:10:0.1 H₂O:CH₃CN:TFA; B=90:10:0.1 CH₃CN:H₂O:TFA) to afford Example 135 (14.9 mg, 47% yield) as an orange solid. $[M+H]^+=414.36$.

Example 136

N5-(6-tert-Butyl-1H-benzo[d]imidazol-2-yl)-6-(2-tert-butylphenoxy)-N2-methylpyridine-2,5-diamine

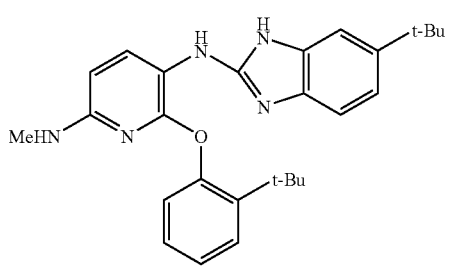

136a. 6-(2-tert-Butyl-phenoxy)-5-nitro-pyridin-2-ol

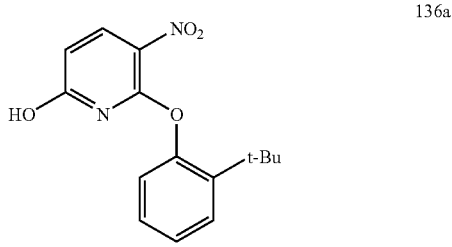

Sodium iodide (10.6 g, 71 mmol) was added to a green solution of 2a (4.26 g, 14 mmol) in acetonitrile (80 mL) in a vessel covered with aluminum foil to protect from light, followed by chlorotrimethylsilane (8.9 mL, 71 mmol) and water (0.4 mL, 21 mmol). The yellow-orange mixture was refluxed overnight in the dark. HPLC analysis showed that although some starting pyridine was still present, decomposition also appeared to be occurring. The reaction was quenched with saturated sodium thiosulfate solution (30 mL). The resulting mixture was extracted with ethyl acetate (3×50 mL). The combined organic layer was washed with brine (30 mL), dried over sodium sulfate, and concentrated to give a yellow oil. The oil was purified by SiO₂ chromatography (120 g), loaded with CH₂Cl₂ and eluted using a gradient of ethyl acetate in hexanes to afford 136a (2.34 g, 58% yield) as a yellow waxy solid, HPLC purity 100%, 3.66 min (Method A); $[M+H]^+=$ 289.17; in $^1$H NMR (500 MHz, CDCl₃) δ ppm 8.42 (d, 1H, J=5.0 Hz), 7.48 (m, 1H), 7.18 (m, 2H), 6.92 (m, 1H), 6.33 (d, 1H, J=10.0 Hz), 1.37 (s, 9H); $^{13}$C (125 MHz, CDCl₃) δ (ppm), 163.87, 155.70, 150.61, 142.05, 139.87, 127.86, 126.83, 125.98, 122.98, 104.62, 34.68, 30.17.

136b. 2-(2-tert-Butylphenoxy)-6-chloro-3-nitropyridine

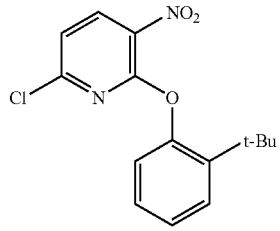

2,4,6-Trimethylpyridine (1.6 mL) was added dropwise into 136a (2.32 g, 8.0 mmol) in phosphorus oxychloride (3.2 mL) at 0° C. The reaction mixture was heated at 130° C. for 20 h. The reaction was stopped at ~70% conversion as determined by HPLC. The dark brown solution was poured into water (40 mL) with stirring, and stirred for 15 min. The brown precipitate was filtered, air dried, and purified by SiO$_2$ chromatography (120 g), loaded with a CH$_2$Cl$_2$ and eluted using a gradient of ethyl acetate in hexanes to afford 136b (1.91 g, 77% yield) as an amber colored oil; HPLC purity 100%, 3.95 min (Method A); $^1$H NMR (500 MHz, CDCl$_3$) δ ppm 8.36 (d, 1H, J=10.0 Hz), 7.47 (d, 1H, J=5.0 Hz), 7.23 (m, 2H), 7.16 (d, 1H, J=10.0 Hz), 6.95 (d, 1H, J=10.0 Hz), 1.36 (s, 9H); $^{13}$C (125 MHz, CDCl$_3$) δ (ppm), 155.30, 153.23, 150.87, 141.45, 137.72, 133.22, 127.59, 126.91, 125.79, 123.04, 118.39, 34.60, 30.25.

136c. 6-(2-tert-Butylphenoxy)-N-methyl-5-nitropyridin-2-amine

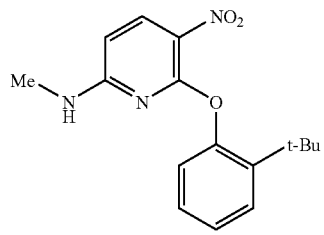

Methylamine (280 μL, 0.56 mmol) was added into a solution of 136b (157 mg, 0.51 mmol) in 1,4-dioxane at 0° C. (1 mL) over 1 h and the resulting reaction mixture was stirred at rt. After 72 h, 40% of the starting chloride remained by HPLC. Another 1.1 eq of methylamine was added at −10° C. over 30 min. The reaction was allowed to warm to rt, stir for 30 min and was then diluted with water (1 mL) and extracted with ethyl acetate (3×1 mL). The combined organic layer was washed with brine (1 mL), dried over sodium sulfate, and concentrated to give a yellow oil. The oil was purified by SiO$_2$ chromatography (12 g) using a gradient of ethyl acetate in hexanes to afford 136c (94 mg, 61% yield) as a yellow oil; HPLC purity 100%, 3.76 min (Method A); [M+H]$^+$=302.24.

136d. 6-(2-tert-Butylphenoxy)-N2-methylpyridine-2,5-diamine

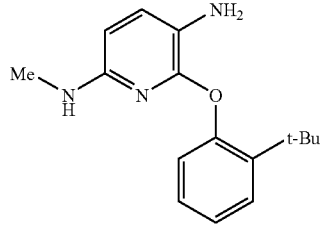

136c was converted to 136d (85 mg, 89% yield) as a pink solid as previously described for 2b. HPLC purity 89%, 2.71 min (Method A); [M+H]$^+$=272.2; $^1$H NMR (500 MHz, CDCl$_3$) δ ppm 1.42 (s, 9H) 2.71 (s, 3H) 6.01 (d, J=8.25 Hz, 1H) 6.91 (d, J=8.25 Hz, 1H) 7.06 (m, 2H) 7.14 (t, J=7.15 Hz, 1H) 7.39 (d, J=7.70 Hz, 1H); $^{13}$C NMR (500 MHz, CDCl$_3$) δ ppm 153.34, 152.02, 150.34, 140.56, 127.67, 126.93, 126.52, 123.39, 121.89, 99.47, 34.68, 30.37, 29.84.

136e. 6-(2-tert-Butylphenoxy)-5-isothiocyanato-N-methylpyridin-2-amine

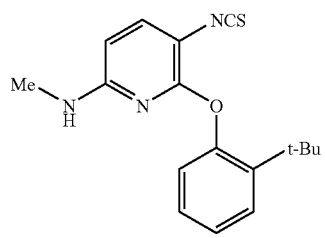

A solution of 136d (16.28 mg, 0.0600 mmol) in anhydrous DCM (1.0 mL) was added dropwise to a cold solution of thiocarbonyl diimidazole (21.39 mg, 0.1200 mmol) in anhydrous DCM (0.50 mL). The reaction was stirred at 0° C. for 1 h and then warmed to rt with stirring for 2 h. The mixture was concentrated down and the residue was flushed through a plug of silica gel with 10% EtOAc in hexanes. Concentration of the eluent afforded 136e.

Example 136

To a solution of 136e (0.060 mmol) in DCE (1 mL) was added 4-(tert-butyl)-1,2-diaminobenzene (19.71 mg, 0.120 mmol). The reaction was stirred overnight at rt. EDC (23.01 mg, 0.120 mmol) was added and the reaction was again stirred overnight at rt. The mixture was concentrated and purified by preparative HPLC (continuous gradient from 20% B to 100% B; A=90:10:0.1 H$_2$O:CH$_3$CN:TFA; B=90:10:0.1 CH$_3$CN:H$_2$O:TFA) to afford Example 136 (5.4 mg, 16% yield) as an orange solid. [M+H]$^+$=444.28.

Example 137

6-tert-Butyl-N-(4-(2-tert-butylphenoxy)pyridin-3-yl)-1H-benzo[d]imidazol-2-amine

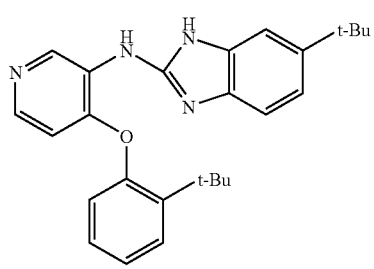

137a. 4-(2-tert-Butylphenoxy)-3-nitropyridine

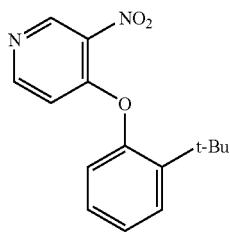

A mixture of 4-chloro-3-nitropyridine (1.29 g, 8.17 mmol), potassium carbonate (1.70 g, 12.3 mmol) and 2-tert-butylphenol (1.30 mL, 8.46 mmol) were stirred in dioxane (8 nit) at 105° C. for 3 days. The mixture was cooled to rt, water (15 mL) was added and the solid was filtered and washed with water. The solid oiled out and the mixture was extracted with ether (3×30 mL), washed with brine (15 mL) dried with magnesium sulfate, filtered and concentrated to give 3.644 g of yellow oil. The oil was applied on a ISCO column (120 g, dry load washed with a little heptane) using a gradient of ethyl acetate in hexanes. 137a (1.332 g, 59% yield) was obtained as a yellow oil, 3.69 min, 100% pure by HPLC. $^1$H NMR (500 MHz, deuterochloroform) δ ppm 1.37 (s, 9H) 6.78 (d, J=6.05 Hz, 1H) 6.92 (m, J=9.41 Hz, 1H) 7.27 (m, 2H) 7.51 (m, 1H) 8.54 (d, J=6.05 Hz, 1H) 9.15 (s, 1H); $^{13}$C (125 MHz, deuterochloroform) δ (ppm), 30.17, 34.72, 112.29, 121.65, 126.48, 127.74, 128.32, 137.14, 142.36, 147.47, 151.56, 154.43, 158.17.

137b. 4-(2-tert-Butylphenoxy)pyridin-3-amine

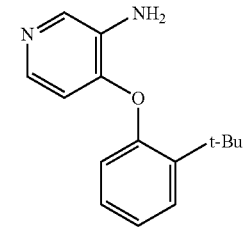

137a (1.332 g, 4.891 mmol) was dissolved in a 1:1 mixture of methanol and ethyl acetate (30 mL). Palladium on charcoal (10%, 200 mg, 0.188 mmol) was added, and the mixture was stirred 2 h under hydrogen atmosphere (40 psi). The reaction mixture was filtered over Celite® and concentrated to afford 1.16 g (98% yield, 100% pure) of 4-(2-tert-butylphenoxy)pyridin-3-amine (137b) as a white solid. [M+H]$^+$=243.17. $^1$H NMR (500 MHz, deuterochloroform) δ ppm 8.07 (s, 1H), 7.75 (d, 1H, J=5.0 Hz), 7.32 (d, 1H, J=10.0 Hz), 7.03 (m, 2H), 6.77 (d, 1H, J=5.0 Hz), 6.41 (d, 1H, J=5.0 Hz), 4.26 (br, 2H), 1.27 (s, 9H); $^{13}$C (125 MHz, deuterochloroform) δ (ppm), 152.89, 150.65, 140.96, 139.93, 137.42, 134.21, 127.13, 126.93, 124.22, 120.56, 110.45, 34.19, 29.86.

137c. 4-(2-tert-Butylphenoxy)-3-isothiocyanatopyridine

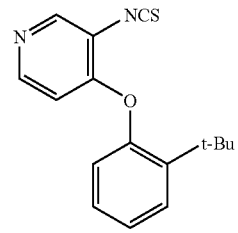

A solution of 137b (14.54 mg, 0.0600 mmol) in anhydrous DCM (1.0 mL) was added dropwise to a cold solution of thiocarbonyl diimidazole (21.39 mg, 0.1200 mmol) in anhydrous DCM (0.50 mL). The reaction was stirred at 0° C. for 1 h and then warmed to rt with stirring for 2 h. The mixture was concentrated down to afford crude 137c which was taken directly onto the next step without purification.

Example 137

To a solution of 137c (0.060 mmol) in DCE (1.0 mL) was added 4-(tert-butyl)-1,2-diaminobenzene (29.57 mg, 0.180 mmol). The reaction was stirred overnight at rt. EDC (92.04 mg, 0.480 mmol) was added and the reaction was again stirred overnight at rt. The mixture was concentrated and purified by preparative HPLC (continuous gradient from 20% B to 100% B; A=90:10:0.1 H$_2$O:CH$_3$CN:TFA; B=90:10:0.1 CH$_3$CN:H$_2$O:TFA) to afford Example 137 (11.7 mg, 37% yield) as a tan solid. [M+H]$^+$=415.28.

Example 138

2-(2-(2-tert-Butylphenoxy)pyridin-3-ylamino)-3H-benzo[d]imidazol-5-ol

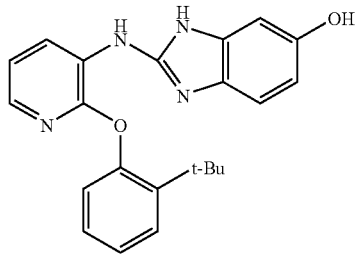

138a. 3,4-Diaminophenol

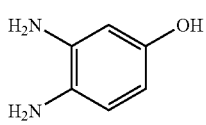

4-Amino-3-nitrophenol (1.09 g, 7.072 mmol) was dissolved into ethanol (50 ml). Palladium on charcoal (10%, 220 mg) was added and the mixture was stirred for 3.5 h under hydrogen atmosphere. The reaction mixture was filtered over Celite® and concentrated to afford 138a (930 mg, 100% yield) as a dark brown solid.

Example 138

To a suspension of 138a (870 mg, 7.03 mmol) in THF (50 ml) under argon was added 1e (1.00 g, 3.516 mmol). The reaction was stirred overnight at rt to generate the thiourea intermediates. EDC (1.35 g, 7.03 mmol) was added and the reaction was stirred at rt over the weekend. The resulting black precipitate was filtered off and washed with THF. The THF filtrate was concentrated down to yield a reddish-brown oil. This crude product was purified by chromatography on silica using a gradient of 0 to 10% of (1% NH$_4$OH in MeOH) in DCM to afford Example 138 (1.08 g, 82% yield) as an orange solid. [M+H]$^+$=375.14.

Example 139

N2-(2-(2-tert-Butylphenoxy)pyridin-3-yl)benzo[d]oxazole-2,4-diamine

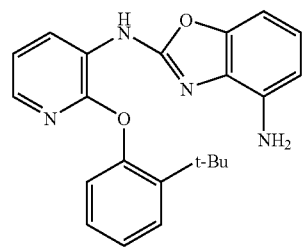

To a solution of 138a (1.31 g, 10.54 mmol) in THF (50 ml) was added 1e (1.50 g, 5.27 mmol). The reaction was stirred at rt for 4 h. EDC (2.02 g, 10.54 mmol) was then added and the reaction was stirred at rt overnight. Analysis of the reaction solution showed it was only 50% complete. Extra EDC (1.00 g) and extra THF (20 ml) were added to drive the reaction to completion with stirring overnight. The resulting precipitates were filtered off and washed with THF. The THF filtrate was concentrated down to yield a mixture of two regioisomeric products. The combined products were purified by chromatography on silica using a gradient of 0 to 10% of (1% NH$_4$OH in MeOH) in DCM. The two regioisomers were then separated by chromatography on silica using a gradient of 0-50% EtOAc in hexanes to afford Example 139 (940 mg, [M+H]$^+$=375.11) as an orange solid and Example 140, see below, (550 mg, [M+H]$^+$=375.13) as a tan solid.

Example 140

2-(2-(2-tert-Butylphenoxy)pyridin-3-ylamino)-1H-benzo[d]imidazol-4-ol

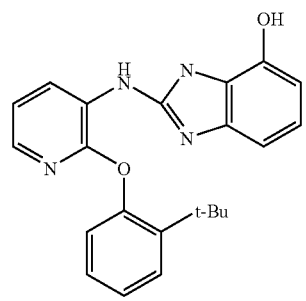

Example 140 was obtained according the experimental procedure of Example 139. [M+H]$^+$=375.13.

Example 141

N-(2-(2-tert-Butylphenoxy)pyridine-3-yl)-1-methyl-1-pyrrolo[2,3-b]pyridine-5-amine

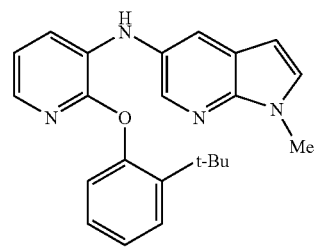

141a. 2-(2-tert-Butylphenoxy)-3-iodopyridine

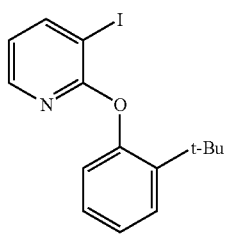

A solution of sodium nitrite (157 mg, 2.28 mmol) in water (1 mL) was added to a mixture of 2-(2-tert-butylphenoxy)-3-aminopyridine (prepared above according to 1b) (500 mg, 2.07 mmol) in (1:1) conc. HCl:water (14 mL) at 0° C. The mixture was stirred at 0° C. for 15 min and a solution of potassium iodide (1.0 g, 6.22 mmol) in water (2 mL) was added. The mixture was stirred at 60° C. for 1.5 h and allowed to cool down to rt. A solution of sodium bisulfite was added and the mixture was extracted with ethyl acetate (3×50 mL). The combined organic layers were dried (anhydrous sodium sulfate), filtered and evaporated. The residue was purified by flash-chromatography (dichloromethane:hexanes/20:100) to afford 394 mg (56%) of 2-(2-tert-butylphenoxy)-3-iodopyridine. $(M+H)^+=354$.

141b. N-(2-(2-tert-Butylphenoxy)pyridine-3-yl)-1-(triisopropylsilyl)-1H-pyrrolo[2,3-b]pyridine-5-amine

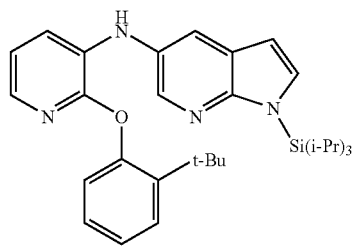

A mixture of 2-(2-tert-butylphenoxy)-3-iodopyridine (prepared as above) (177 mg, 0.50 mmol), N-triisopropylsilyl 5-amino-7-azaindole (see Heureux, A. L. et al., *Tetrahedron Lett.* 2004, 45, 2317) (145 mg, 0.50 mmol), dppf (8.2 mg, 0.015 mmol), $Pd_2(dba)_3$ (9.1 mg, 0.010 mmol), sodium tert-butoxide (72 mg, 0.64 mmol) in toluene (8.0 mL) was heated in a seal tube at 110° C. for 16 h. The mixture was allowed to cool and saturated ammonium chloride (30 mL) was added and the mixture was extracted with ethyl acetate (3×25 mL). The combined organic layers were dried (anhydrous sodium sulfate), filtered and evaporated to yield a residue was purified by reverse phase preparative HPLC to provide 141b. $(M+H)^+=375$.

Example 141

A solution of tetrabutylammonium fluoride in THF (1M, 0.34 mL, 0.34 mmol) was added to a solution of 141b (177 mg, 0.34 mmol) in THF (2.0 mL). The mixture was stirred at rt for 1.5 h and evaporated under reduced pressure. The residue was purified by reverse phase preparative HPLC to provide a compound (50 mg, 0.14 mmol) which was dissolved in THF (1.0 mL). Sodium hydride (60% oil, 24 mg, 0.35 mmol) was added and the resulting mixture was stirred at rt for 10 min. Iodomethane (10 L, 0.15 mmol) was added and the mixture was stirred at rt for 4 h. Saturated ammonium chloride was added and the separated aqueous layer was extracted with ethyl acetate (3×20 mL). The combined organic layers were dried (anh. $Na_2SO_4$), filtered and evaporated. The residue was purified by reverse phase preparative HPLC to provide Example 141. $[M+H]^+=373$. $^1H$ NMR (400 MHz, DMSO-d6) δ ppm 1.34 (s, 9H), 3.82 (s, 3H), 6.42 (d, J=3.5 Hz, 1H), 6.90 (dd, J=7.8, 4.8 Hz, 1H), 6.93 (dd, J=8.1, 1.5 Hz, 1H), 7.13 (dt, J=7.8, 1.5 Hz, 2H), 7.25 (m, 2H), 7.45 (m, 2H), 7.51 (d, J=3.5 Hz, 1H), 7.84 (d, J=3.5 Hz, 1H), 8.23 (d, J=3.5 Hz, 1H).

Example 142

1-(2-(2-(2-tert-Butylphenoxy)pyridin-3-ylamino)-3H-benzo[d]imidazol-5-yl)ethanone

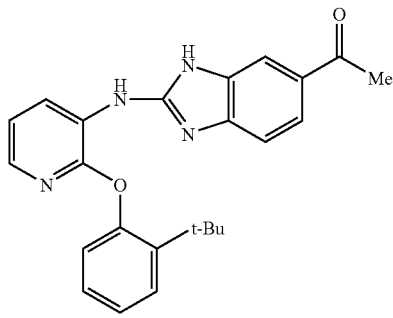

142

142a. 1-(3,4-Diaminophenyl)ethanone

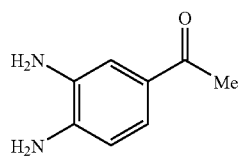

To a solution of 4-methylcarbonyl-2-nitro-benzenamine (500 mg, 2.775 mmol) in EtOAc (16 mL) was added SnCl$_2$.2H$_2$O (3.130 g, 13.88 mmol). The reaction mixture was refluxed for 2.5 h, cooled to rt, and diluted with H$_2$O (130 mL). The pH of the mixture was adjusted to 7-8 by addition of saturated NaHCO$_3$ solution and the aqueous phase was extracted with EtOAc (2×120 mL). The combined organic extracts were washed with brine (2×60 mL) and dried over MgSO$_4$. After the removal of the solvent under vacuum, 142a was obtained as a red orange solid (418 mg).

142b. 1-(4-Acetylphenyl)-3-(2-(3-(trifluoromethylphenoxy)pyridin-3-yl)thiourea (142ba)

1-(3-Acetylphenyl)-3-(2-(3-(trifluoromethylphenoxy)pyridin-3-yl)thiourea (142bb)

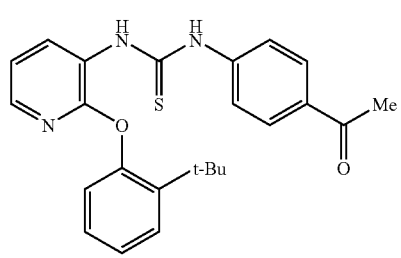

142ba

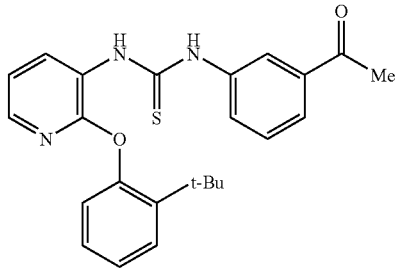

142bb

To a suspension of 142a (100 mg, 0.666 mmol) in DCE (4 mL), was slowly added 2-(2-tert-butylphenoxy)-3-isothiocyanatopyridine (94 mg, 0.332 mmol) prepared according to 1c. The reaction mixture was stirred at rt over night and concentrated. The crude mixture was used in the next step without further purification.

Example 142

To a solution of the mixture 142ba and 142bb in dichloroethane (3 mL), was added EDC (78 mg, 0.41 mmol). The mixture was stirred overnight at rt, volatiles evaporated and the residue purified by preparative HPLC (continuous gradient from 30% B to 65% B; A=90:10:0.1 H$_2$O:MeOH:TFA; B=90:10:0.1 MeOH:H$_2$O:TFA) to yield Example 142. t$_R$=5.195 min (Shimadzu YMC S5 ODS 4.6×50 min Ballistic flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{24}$H$_{25}$N$_4$O$_2$ [M+H]$^+$ 401.1978, found 401.1959.

Example 143

1-(2-(2-(2-tert-Butylphenoxy)pyridin-3-ylamino)-3H-benzo[d]imidazol-5-yl)ethanol

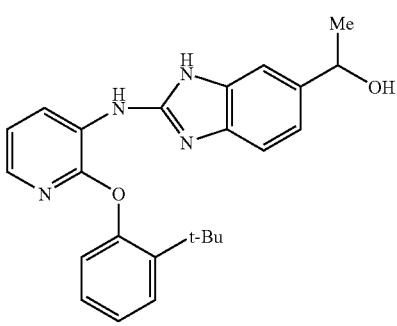

143

Example 142 (180 mg, 0.449 mmol) was dissolved in MeOH (5 mL) and the solution was cooled to 0° C. NaBH$_4$ (17 mg, 0.449 mmol) was added portionwise over 2 min. The mixture was allowed to warm to ambient temperature over 0.5 h, volatiles were evaporated and the residue was purified by column chromatography on silica gel ISCO system (eluting with a continuous gradient from 0% to 50% ethyl acetate in hexane over 30 min). Example 143 was obtained as a yellow solid (170 mg, 94%). t$_R$=4.59 min (Shimadzu Phenomenex S5 ODS 4.6×50 mm Luna C18; flow rate 2.5 mL/mn; detection at 220 nM; Gradient elution 0% to 100% B over 8 min;

(A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{24}$H$_{27}$N$_4$O$_2$ [M+H]$^+$ 403.2134. found 403.2137.

Example 144

6-(1-((4-(Trifluoromethyl)benzyl)(methyl)amino)ethyl)-N-(2-(2-tert-butylphenoxypyridin-3-yl)-1H-benzo[d]imidazol-2-amine

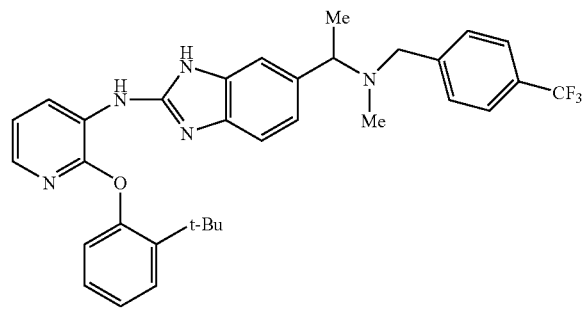

144

Example 143 (23 mg, 0.057 mmol) was mixed with DCE (1.5 mL) and the mixture was cooled to 0° C. SOCl$_2$ (0.043 mL, 0.586 mmol) was added slowly and the mixture allowed to warm to rt and stirred overnight. Volatiles were evaporated under reduced pressure, and traces of SOCl$_2$ were removed by coevaporation of DCE (4×3 mL). The crude intermediate was mixed with 4-trifluorobenzylamine (20 µL) and stirred for 1 h at rt. Volatiles were evaporated and the residue purified by preparative HPLC (Eluting with continuous gradient from 5% B to 65% B; A=90:10:0.1 H$_2$O:MeOH:TFA; B=90:10:0.1 MeOH:H$_2$O:TFA) to yield Example 144. t$_R$=4.958 min (Shimadzu YMC Combiscreen ODS-A 4.6×50 mm; flow rate 2.5 mL/mn; detection at 220 nM; Gradient elution 0% to 100% B over 8 min; (A 10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{33}$H$_{35}$F$_3$N$_5$O [M+H]$^+$ 574.2794. found 574.2797.

Example 145

(2-(2-(2-tert-Butylphenoxy)pyridin-3-ylamino)-3H-benzo[d]imidazol-5-yl)methanol

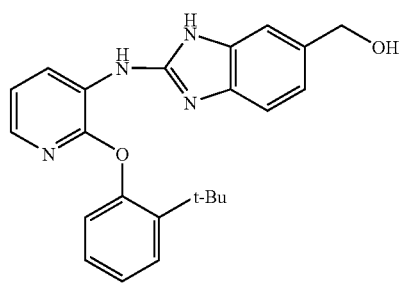

145

A solution of methyl 2-(2-(2-tert-butylphenoxy)pyridin-3-ylamino)-3H-benzo[d]imidazole-5-carboxylate (Example 14, 65 mg, 0.156 mmol), in dry THF (6 mL) was added to a cooled (0° C.) solution of LiAlH$_4$ in THF (0.39 mL, 1.0 M solution). After 2 h, the reaction was allowed to warm to rt and stirred for 24 h. The mixture was cooled to 0° C., the excess of LiAlH$_4$ was destroyed very with a saturated solution of NH$_4$Cl. The product was extracted with EtOAc (4×20 mL), dried over MgSO$_4$ and evaporated to yield a white solid. Example 145 was obtained after preparative HPLC purification (continuous gradient from 10% B to 60% B; A=90:10:0.1 H$_2$O:MeOH:TFA; B=90:10:0.1 MeOH:H$_2$O:TFA). t$_R$=4.589 min (Shimadzu Phenomenex S5 ODS 4.6×50 mm Luna 4.6× 50 mm; flow rate 2.5 mL/inn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{23}$H$_{25}$N$_4$O$_2$ [M+H]$^+$ 389.1978. found 389.1972.

Example 146

2-(2-(2-tert-Butylphenoxy)pyridin-3-ylamino)-3H-benzo[d]imidazole-5-carboxylic acid

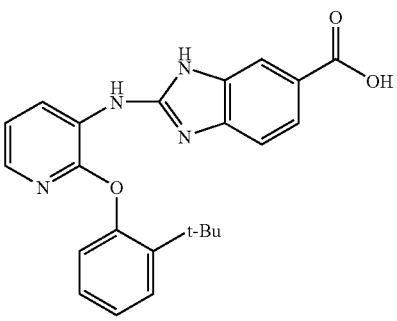

146

Methyl 2-(2-(2-tert-butylphenoxy)pyridin-3-ylamino)-3H-benzo[d]imidazole-5-carboxylate (Example 14, 526 mg, 1.263 mmol) was dissolved in a mixture of 1N NaOH (8 mL) and dioxane (3 mL) and stirred for 24 h. The reaction mixture was cooled to 0° C. and 1 N HCl was added dropwise to adjust the PH to 2~3. The mixture was extracted with EtOAc (4×25 mL), dried over MgSO$_4$ and evaporated to yield Example 146 as a white solid (402 mg). LC-MS (ESI) 403.08 [M+H]$^+$, t$_R$=2.84 min (over 4 mm).

Example 147

N-(4-(Trifluoromethyl)benzyl)-2-(2-(2-tert-butylphenoxy)pyridin-3-ylamino)-3H-benzo[d]imidazole-5-carboxamide

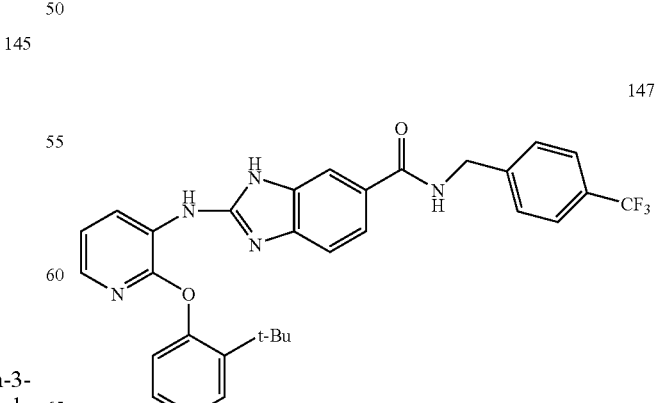

147

Example 146 (23 mg, 0.0571 mmol), EDAC (22 mg, 0.114 mmol), HOBT hydrate (23 mg, 0.0571 mmol) were with 1 mL anhydrous DMF and cooled to 0° C. To this mixture under $N_2$ atmosphere, was added 24 µL of TEA, followed by 4-trifluoromethylbenzylamine (8 µL, 0.0571 mmol). The reaction was allowed to warm to rt and stirring continued for 24 h. EtOAc (50 mL) was added, and the mixture washed with $H_2O$ (2×20 mL), dried over $MgSO_4$ and evaporated to yield a brown oil. This was purified by preparative HPLC (continuous gradient from 20% B to 75% B; A=90:10:0.1 $H_2O$:MeOH:TFA; B=90:10:0.1 MeOH:$H_2O$:TFA) to afford Example 147. $t_R$=6.371 min (Shimadzu Phenomenex S5 ODS 4.6×50 nm n Luna 4.6×50 mm; flow rate 2.5 mL/mn; detection at 220 nM; Gradient elution 0% to 100% B over 8 min; (A 10% MeOH, 90% $H_2O$, 0.2% $H_3PO_4$ & B=90% MeOH, 10% $H_2O$, 0.2% $H_3PO_4$). HRMS (ESI) m/z calcd for $C_{31}H_{29}F_3N_5O_2$ [M+H]$^+$ 560.2273. found 560.2300.

Examples 148 to 211

Examples 148 to 163 listed in Table 5 below were prepared by using the appropriated reagents according to the method of Example 147.

Examples 164 to 211 listed in Table 5 below were prepared by reacting the appropriated reagents according to the method of Example 144.

TABLE 5

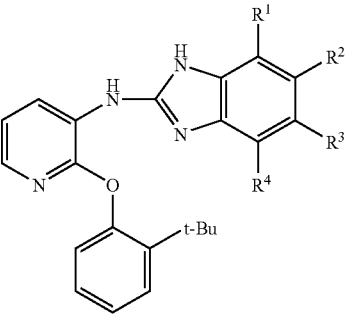

| Ex. No. | | $t_R$ min | HRMS [M + H]$^+$ |
|---|---|---|---|
| 148 | 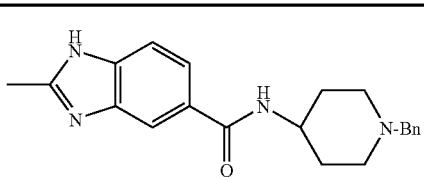 | 4.392 | 575.3149 |
| 149 | 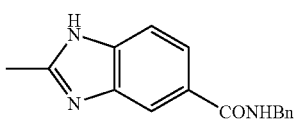 | 5.722 | 492.2400 |
| 150 | 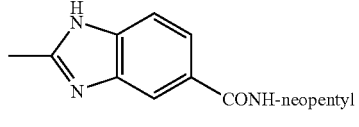 | 5.798 | 472.2719 |
| 151 | 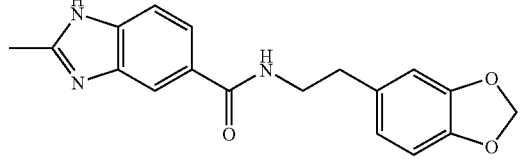 | 5.81 | 550.2463 |

TABLE 5-continued
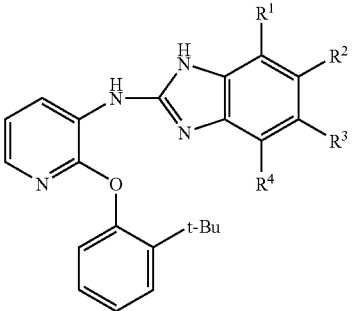
| Ex. No. | R⁴ | $t_R$ min | HRMS [M + H]⁺ |
|---|---|---|---|
| 152 | 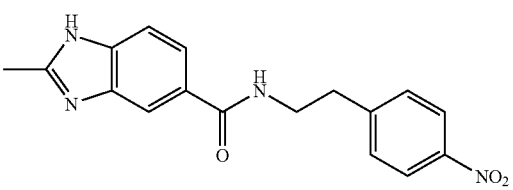 | 5.905 | 551.2412 |
| 153 | 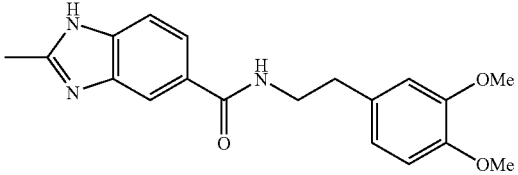 | 5.602 | 566.2780 |
| 154 | 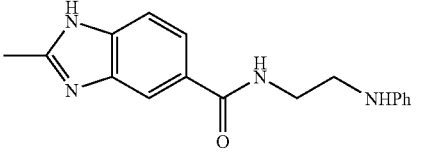 | 5.092 | 571.3048 |
| 155 | 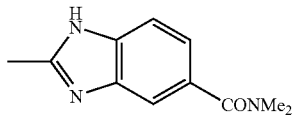 | 4.36 | 430.2180 |
| 156 | 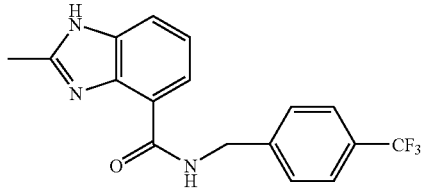 | 7.618 | 560.2252 |
| 157 | 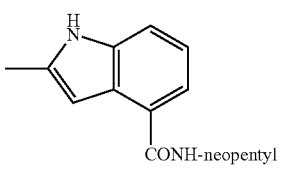 | 7.448 | 472.2710 |

103
104
TABLE 5-continued
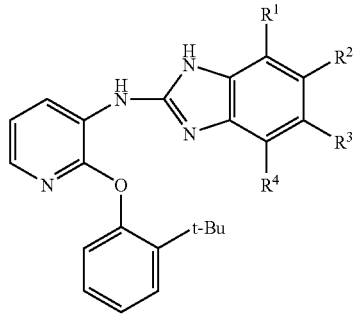
| Ex. No. |  | $t_R$ min | HRMS [M + H]$^+$ |
|---|---|---|---|
| 158 | 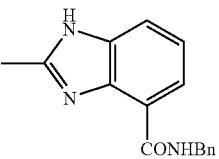 | 5.853 | 506.2560 |
| 159 |  | 7.214 | 492.2419 |
| 160 | 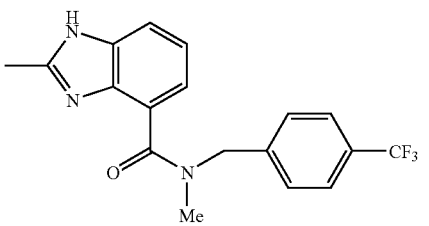 | 5.125 | 444.2383 |
| 161 | 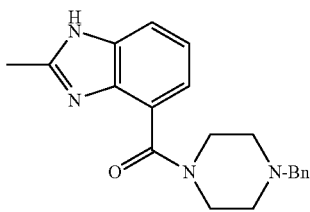 | 6.520 | 574.2435 |
| 162 | | 3.792 | 561.2953 |

TABLE 5-continued
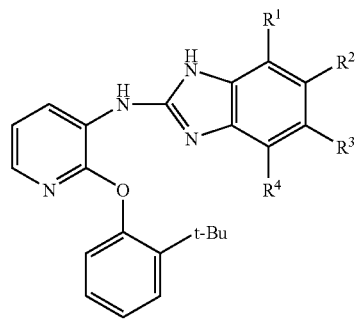
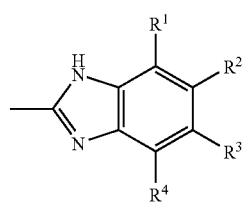
| Ex. No. | R⁴ | t_R min | HRMS [M + H]⁺ |
|---|---|---|---|
| 163 | (2-methylbenzimidazole-4-CONH₂) | 4.863 | 402.1947 |
| 164 | (2-methylbenzimidazole-5-CH₂NH-CH₂-C₆H₄-4-CF₃) | 4.63 | 546.2435 |
| 165 | (2-methylbenzimidazole-5-CH₂-N(Me)(Bn)) | 4.029 | 492.2774 |
| 166 | (2-methylbenzimidazole-5-CH₂-NHBn) | 4.109 | 478.2623 |
| 167 | (2-methylbenzimidazole-5-CH(Me)-N(Me)(Et)) | 3.177 | 444.2759 |
| 168 | (2-methylbenzimidazole-5-CH(Me)-N(Me)(Bn)) | 3.905 | 506.2914 |
| 169 | (2-methylbenzimidazole-5-CH(Me)-piperidinyl) | 3.363 | 470.2926 |

TABLE 5-continued
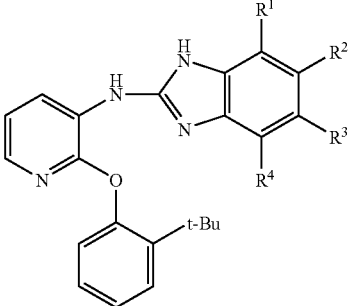
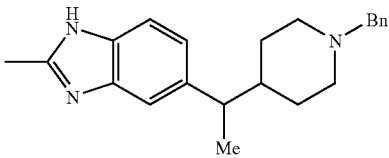
| Ex. No. | R¹ R² R³ R⁴ | $t_R$ min | HRMS [M + H]⁺ |
|---|---|---|---|
| 170 | 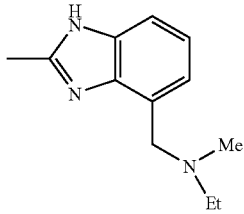 | 3.74 | 561.3361 |
| 171 | 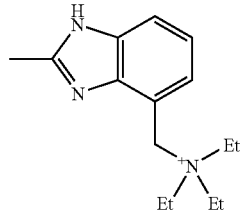 | 3.23 | 430.2624 |
| 172 | 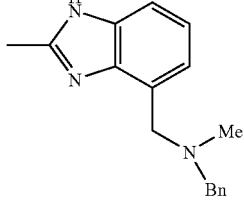 | 3.949 | 372.3065 |
| 173 | 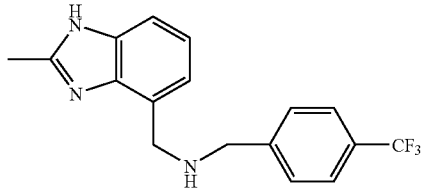 | 4.357 | 492.2743 |
| 174 | | 5.15 | 546.2462 |

TABLE 5-continued

| Ex. No. | | $t_R$ min | HRMS [M + H]+ |
|---|---|---|---|
| 175 | 2-methyl-4-((4-benzylpiperazin-1-yl)methyl)-1H-benzimidazole | 3.913 | 547.3168 |
| 176 | 2-methyl-4-((N-methyl-N-(4-trifluoromethylbenzyl)amino)methyl)-1H-benzimidazole | 5.633 | 560.2620 |
| 177 | 2-methyl-5-(1-(N-ethyl-N-benzylamino)ethyl)-1H-benzimidazole | 4.268 | 520.3079 |
| 178 | 2-methyl-5-(1-(N-methyl-N-(4-fluorobenzyl)amino)ethyl)-1H-benzimidazole | 4.375 | 524.2831 |
| 179 | 2-methyl-5-(1-(N-methyl-N-(4-trifluoromethylbenzyl)amino)ethyl)-1H-benzimidazole | 4.958 | 574.2797 |

TABLE 5-continued
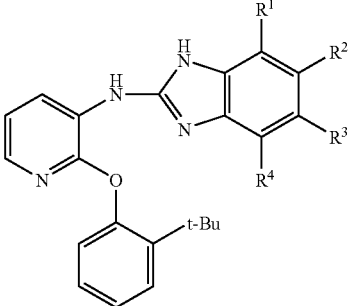
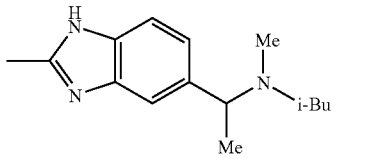
| Ex. No. | | $t_R$ min | HRMS [M + H]+ |
|---|---|---|---|
| 180 | 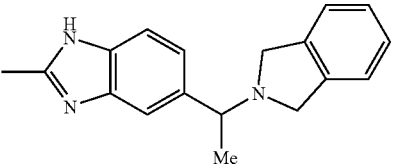 | 3.835 | 472.3078 |
| 181 | 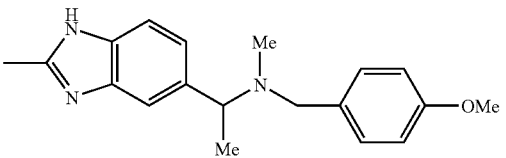 | 3.958 | 504.2754 |
| 182 | 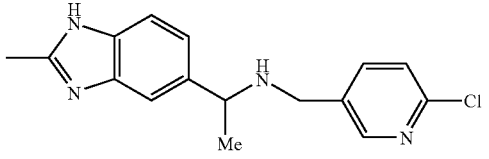 | 4.405 | 536.3026 |
| 183 | 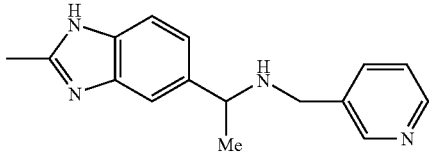 | 3.713 | 527.2329 |
| 184 | 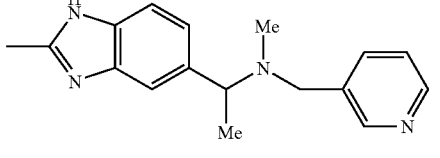 | 2.923 | 493.2711 |
| 185 | | 2.925 | 507.2861 |

TABLE 5-continued
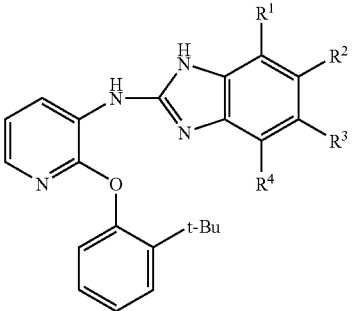
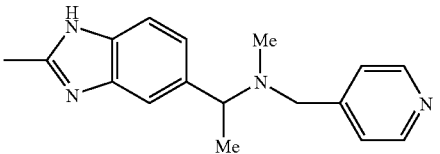
| Ex. No. | R⁴ | $t_R$ min | HRMS [M + H]⁺ |
|---|---|---|---|
| 186 | 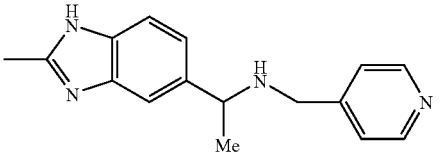 | 2.862 | 507.2867 |
| 187 | 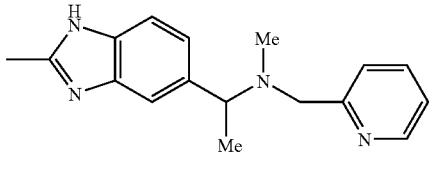 | 2.75 | 493.2730 |
| 188 | 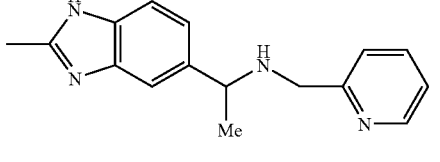 | 3.458 | 507.2887 |
| 189 | 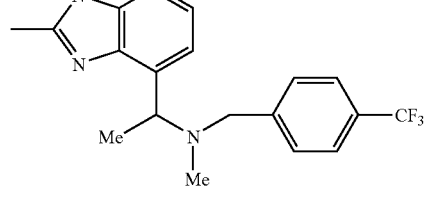 | 3.475 | 493.2727 |
| 190 | 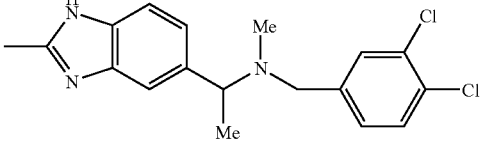 | 6.325 | 574.2793 |
| 191 |  | 5.570 | 574.2157 |

TABLE 5-continued

| Ex. No. | | $t_R$ min | HRMS [M + H]⁺ |
|---|---|---|---|
| 192 | (2-methyl-1H-benzimidazol-5-yl)-CH(Me)-N(Me)-CH₂-(3-CF₃-C₆H₄) | 5.287 | 574.2819 |
| 193 | (2-methyl-1H-benzimidazol-5-yl)-CH(Me)-N(Me)-CH₂-(2-thienyl) | 4.555 | 512.2496 |
| 194 | (2-methyl-1H-benzimidazol-5-yl)-CH(Me)-N(Me)-CH₂CH₂-Ph | 4.868 | 520.3096 |
| 195 | (2-methyl-1H-benzimidazol-5-yl)-CH(Me)-N(Me)-CH₂-(2-furyl) | 4.370 | 496.2704 |
| 196 | (2-methyl-1H-benzimidazol-5-yl)-CH(Me)-N(Et)-CH₂-(2-Cl-C₆H₄) | 4.887 | 554.2695 |
| 197 | (2-methyl-1H-benzimidazol-5-yl)-CH(Me)-N(Bn)-CH₂-CO₂Me | 6.473 | 578.3143 |

TABLE 5-continued

| Ex. No. | | $t_R$ min | HRMS [M + H]$^+$ |
|---|---|---|---|
| 198 | | 5.273 | [M + Na] + 572.2621 |
| 199 | | 4.688 | 536.52 |
| 200 | | 4.733 | 492.2756 |
| 201 | | 5.59 | 506.2928 |
| 202 | | 6.54 | 574.2146 |

TABLE 5-continued
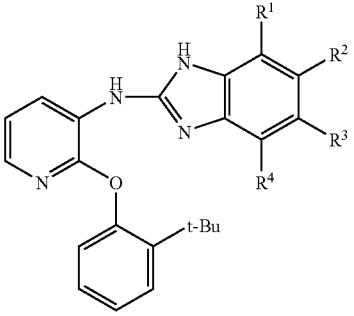
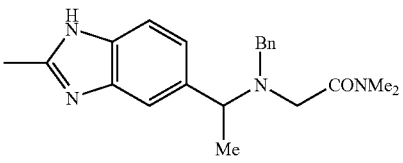
| Ex. No. | | $t_R$ min | HRMS [M + H]$^+$ |
|---|---|---|---|
| 203 | 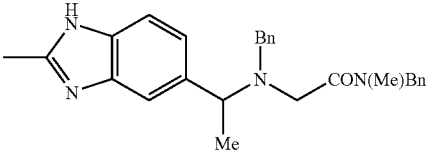 | 4.785 | 577.3303 |
| 204 | 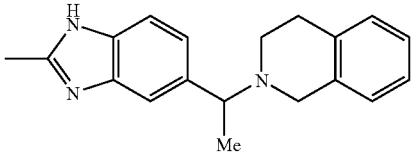 | 5.737 | 653.10 |
| 205 | 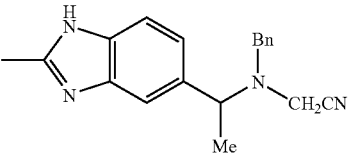 | 4.64 | 518.2923 |
| 206 | 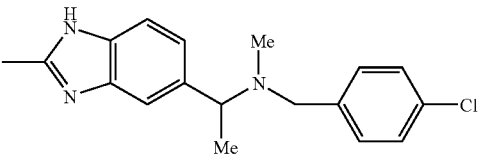 | 6.88 | 531.2856 |
| 207 | 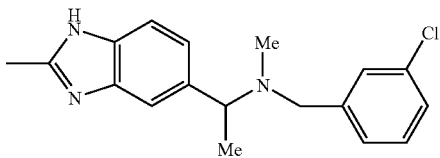 | 4.83 | 540.2526 |
| 208 | | 5.06 | 540.2508 |

TABLE 5-continued
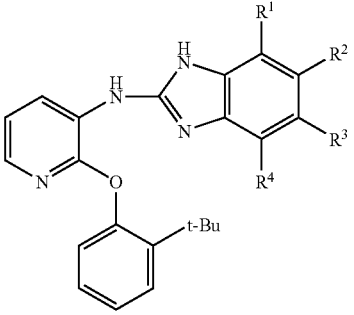
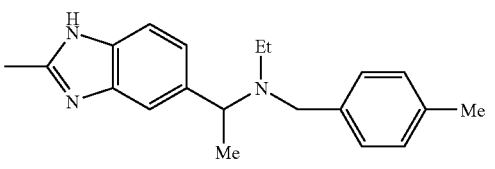
| Ex. No. | | $t_R$ min | HRMS [M + H]$^+$ |
|---|---|---|---|
| 209 | 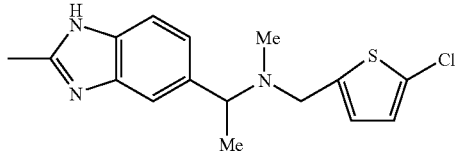 | 5.118 | 534.3248 |
| 210 | 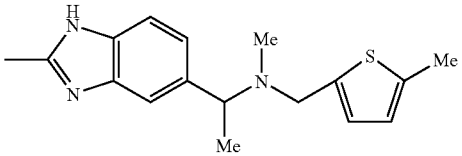 | 5.16 | 546.2076 |
| 211 | 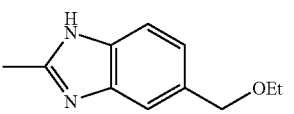 | 4.982 | 526.2627 |
| 213 | 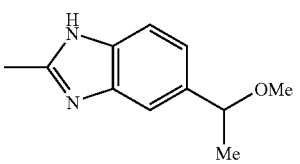 | 5.35 | 417.2291 |
| 214 | | 5.842 | 417.2270 |
| 215 | 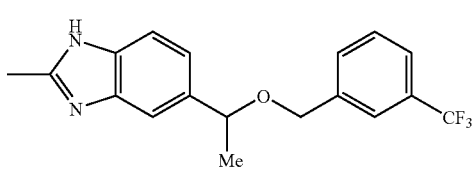 | 7.251 | 561.2454 |

TABLE 5-continued
| Ex. No. | | $t_R$ min | HRMS [M + H]$^+$ |
|---|---|---|---|
| 216 | 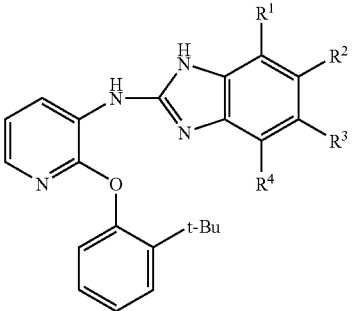 | 7.691 | 561.1824 |
| 217 | 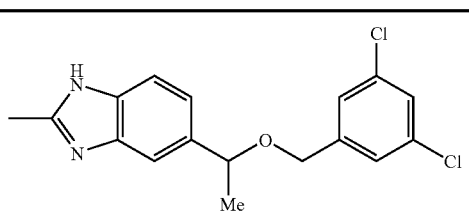 | 6.887 | 493.2596 |
| 218 | 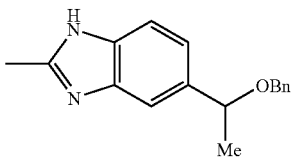 | 7.617 | 535.3062 |
| 219 | 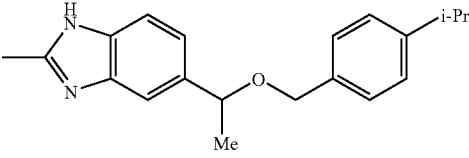 | 7.575 | 585.07 |
| 220 | 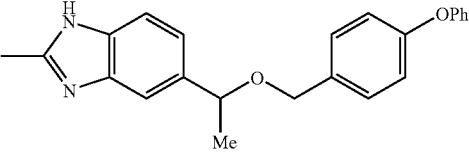 | 4.46 | 516.3323 |
| 221 | 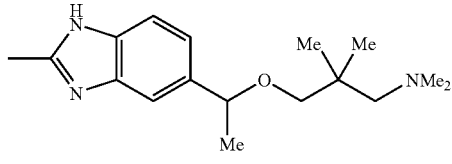 | 5.11 | 590.3503 |

Example 212

6-(1-(4-(Trifluoromethyl)benzyloxy)ethyl)-N-(2-(2-tert-butylphenoxy)pyridine-3-yl)-1H-benzo[d]imidazol-2-amine

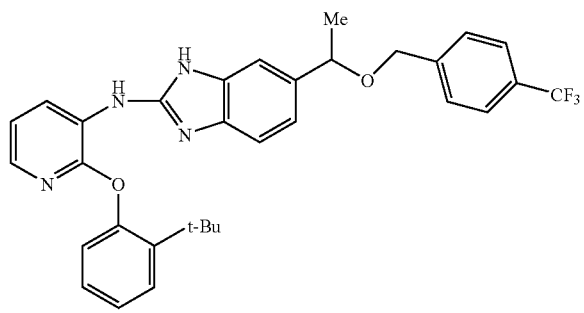

Example 143 (23 mg, 0.057 mmol) was mixed with DCE (1.5 mL) and the mixture cooled to 0° C. SOCl$_2$ (0.043 mL, 0.586 mmol) was added slowly and the mixture allowed to warm to rt and stirred overnight. Volatiles were evaporated under reduced pressures and traces of SOCl$_2$ were removed by coevaporation of DCE (4×3 mL). The crude intermediate was mixed with 4-trifluorobenzylalcohol (20 µL) and stirred for 1 h at rt then heated to 90° C. for 30 min. Volatiles were evaporated and the residue purified by preparative HPLC (Eluting with continuous gradient from 5% B to 65% B; A=90:10:0.1 H$_2$O:MeOH:TFA; B=90:10:0.1 MeOH:H$_2$O:TFA) to yield Example 212. t$_R$=6.798 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{32}$H$_{32}$F$_3$N$_4$O$_2$ [M+H]$^+$ 561.2477, found 561.2473.

Examples 213 to 221

Examples 213 to 221 listed in Table 5 above were prepared by reacting the appropriated reagents according to the method of Example 212.

Example 222

6-tert-Butyl-N-(2-(2-tert-butylphenoxy)pyridine-3-yl)-1-methyl-1H-benzo[d]imidazol-2-amine

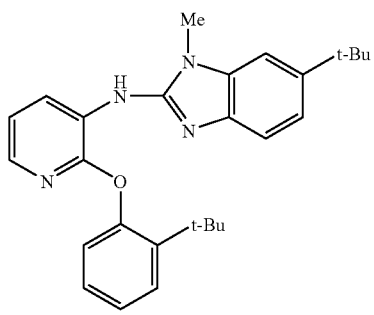

5-tert-Butyl-N-(2-(2-tert-butylphenoxy)pyridine-3-yl)-1H-benzo[d]imidazol-2-amine (Example 6, 50 mg, 0.121 mmol) was dissolved in THF (2 mL). At 0° C., NaH (2.6 mg, 0.109 mmol) was added and the mixture stirred for 11 min. ICH$_3$ (15 mg, 0.109 mmol) was then slowly introduced. The solution turned purple. After 15 min additional stirring, the solvent was removed under vacuum and the crude product was purified by column chromatography on silica gel (eluting with a continuous gradient of MeOH from 0% to 5% in CH$_2$Cl$_2$). t$_R$=6.265 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{27}$H$_{32}$N$_4$O [M+H]$^+$ 429.2654. found 429.2636.

Example 223

5-tert-Butyl-N-(2-(2-tert-butylphenoxy)pyridine-3-yl)-1-methyl-1H-benzo[d]imidazol-2-amine

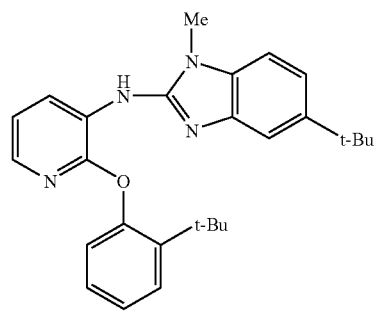

From the reaction mixture of Example 222 was also isolated Example 223. t$_R$=5.935 min; HRMS (ESI m/z calcd for C$_{27}$H$_{32}$N$_4$O [M+H]$^+$ 429.2654, found 429.2657.

Example 224

5-tert-Butyl-1-butyl-N-(2-(2-tert-butylphenoxy)pyridine-3-yl)-1H-benzo[d]imidazol-2-amine

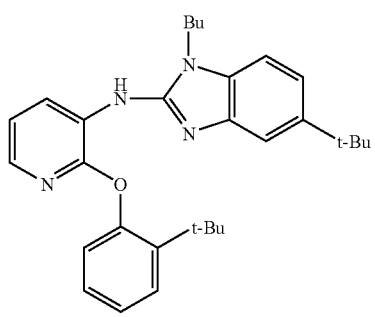

Example 224 was prepared according to the method of Example 222. t$_R$=6.761 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90%

Example 225

1-(2-(2-(2-tert-Butylphenoxy)pyridine-3-ylamino)benzo[d]thiazol-6-yl)ethanone

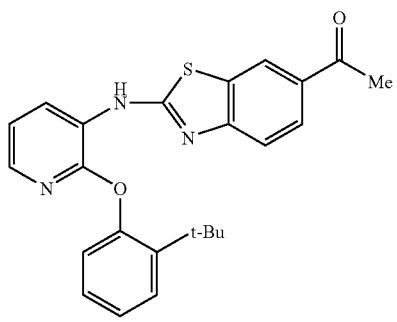

225a. 1-(4-Acetylphenyl)-3-(2-(2-tert-butylphenoxy)pyridine-3-yl)thiourea

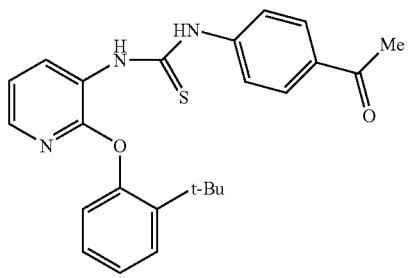

127.15 mg (0.525 mmol) of 1b were mixed with 92.16 mg (0.525 mmol) of 1-(4-isothiocyanatophenyl)ethanone, 5 mL of CH$_2$Cl$_2$ and 6.61 mg (0.052 mmol) of DMAP and refluxed under Argon for 72 h. 225a was filtered and purified by crystallization in MeOH to yield 43.3 mg of an off-white solid used in the next step without further purification.

Example 225

70 mg (0.167 mmol) of 225a was dissolved in 4 mL of chloroform. To this solution cooled to 55° C. were added dropwise 26 mg of bromine (0.16 mmol) in 1 mL of CHCl$_3$. The mixture was stirred for 1 h at −55° C. Water (2 mL) and CHCl$_3$ (2 mL) were added and the pH of the solution adjusted to 8-9 with NH$_4$OH. Organic phase was separated, washed twice with water (2 mL), dried over MgSO$_4$ and concentrated to yield an amorphous solid purified by preparative HPLC. $t_R$=7.541 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{24}$H$_{24}$N$_3$O$_2$S [M+H]$^+$ 418.1589. found 418.1574. $^1$H NMR (500 MHz, CD$_3$OD) δ ppm 1.35 (m, 9H), 6.96 (dd, J=7.7, 1.1 Hz, 1H), 7.16 (m, 3H), 7.47 (dd, J=7.7, 1.6 Hz, 1H), 7.66 (d, J=8.8 Hz, 1H), 7.78 (dd, J=4.4, 1.6 Hz, 1H), 8.0 (dd, J=8.25, 1.65 Hz, 1H), 8.40 (d, 1.65 Hz, 1H); 8.85 (dd, J=7.7, 1.6 Hz, 1H).

Example 226

2,2-Dibromo-1-(2-(2-(2-tert-butylphenoxy)pyridine-3-ylamino)benzo[d]thiazol-6-yl)ethanone

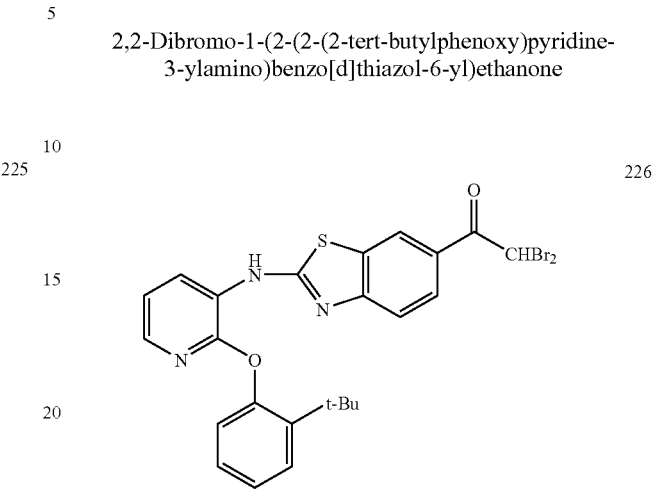

41.9 mg (0.1 mmol) of 225a was dissolved in 3 mL of chloroform. To this solution were added dropwise 16 mg of bromine in 1 mL of CHCl$_3$. The mixture was refluxed for 1 h. The solid formed was filtered to yield 60.2 mg of Example 226. $t_R$=8.081 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{24}$H$_{22}$Br$_2$N$_3$O$_2$S [M+H]$^+$ 573.9799. found 573.9811. $^1$H NMR (400 MHz, CD$_3$OD) δ ppm 1.34 (m, 9H), 6.96 (dd, J=7.9, 1.3 Hz, 1H), 7.16 (m, 3H), 7.46 (dd, J=7.9, 1.76 Hz, 1H), 7.51 (s, 1H), 7.68 (d, J=8.8 Hz, 1H); 7.79 (dd, J=4.8, 1.76 Hz, 1H), 8.08 (dd, J=8.25, 1.65 Hz, 1H), 8.49 (d, J=1.76 Hz, 1H); 8.86 (dd, J=1.76; 7.9 Hz, 1H).

Example 227

1-(2-(2-(2-tert-Butylphenoxy)pyridine-3-ylamino)benzo[d]thiazol-6-yl)ethanol

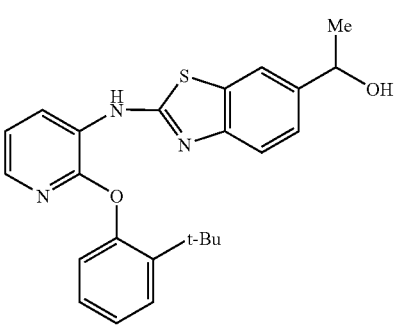

20.9 mg (0.05 mmol) of Example 225 was dissolved in 2 mL of isopropanol. To this solution were added 18.9 mg (0.05 mmol) of NaBH$_4$. The mixture was stirred at room temperature for 30 min and concentrated to dryness under vacuum. 2 mL of water were added and the solution was extracted with CH$_2$Cl$_2$, dried over MgSO$_4$ and evaporated to yield 17 mg of the crude expected derivative purified by preparative HPLC. (Eluting with continuous gradient from 50% B to 100% B; A=90:10 H$_2$O:MeOH; B=90:10 MeOH:H$_2$O) to yield Example 227. t$_R$=7.121 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{24}$H$_{26}$N$_3$O$_2$S [M+H]$^+$ 420.1746. found 420.1747. $^1$H NMR (500 MHz, CD$_3$OD) δ ppm 1.37 (s, 9H), 1.35 (d, J=6.8 Hz, 3H), 4.99 (q, J=6.4 Hz, 1H), 6.97 (dd, J=7.7, 1.1 Hz, 1H), 7.09 (dd, J=8.25, 4.95 Hz, 1H), 7.18 (td, J=7.7, 1.1 Hz, 1H), 7.25 (m, 1H), 7.39 (dd, J=8.25, 1.65 Hz, 1H); 7.47 (dd, J=7.7, 1.65 Hz, 1H), 7.70 (d, J=8.25 Hz, 1H), 7.73 (d, J=1.1 Hz, 1H); 7.83 (dd, J=4.95, 1.65 Hz, 1H), 8.86 (dd, J=1.65; 7.7 Hz, 1H).

Examples 228 to 230

Examples 228 to 230 listed in Table 6 below were prepared by reacting the appropriated reagents with Example 227 according to the method of Example 144.

TABLE 6

| Example No. | (structure with R$^1$, R$^2$, R$^3$, R$^4$) | t$_R$ min | HRMS [M + H]$^+$ |
|---|---|---|---|
| 228 | 2-methylbenzothiazole-6-yl-CH(Me)-N(Me)(Bn) | 6.218 | 523.2546 |
| 229 | 2-methylbenzothiazole-6-yl-CH(Me)-N(Me)-CH$_2$-(4-CF$_3$-phenyl) | 6.578 | 591.2421 |
| 230 | 2-methylbenzothiazole-6-yl-CH(Me)-N(Me)-CH$_2$-(5-Cl-thiophene-2-yl) | 6.952 | 563.1724 |
| 236 | 6-bromo-2-methylbenzothiazole | 8.56 | 454.0589 |
| 237 | 4-SMe-2-methylbenzothiazole | 8.317 | 422.1346 |

TABLE 6-continued
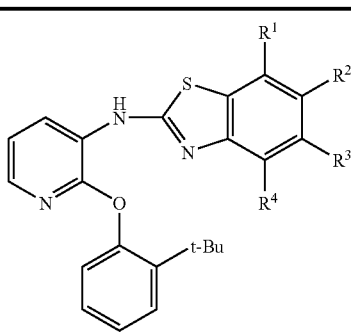
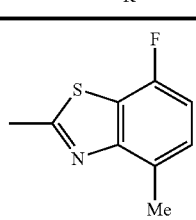
| Example No. | R⁴ | $t_R$ min | HRMS [M + H]⁺ |
|---|---|---|---|
| 238 | 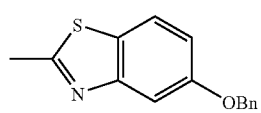 | 8.707 | 408.1534 |
| 239 | 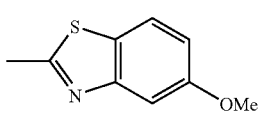 | 8.531 | 482.1884 |
| 240 | 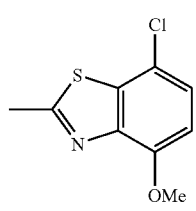 | 7.817 | 406.1572 |
| 241 | 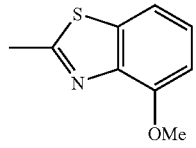 | 8.251 | 440.1209 |
| 242 |  | 7.758 | 406.1523 |
| 243 | 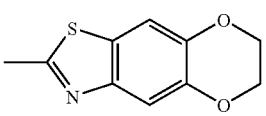 | 8.784 | 472.0477 |
| 244 |  | 7.788 | 434.1528 |

TABLE 6-continued
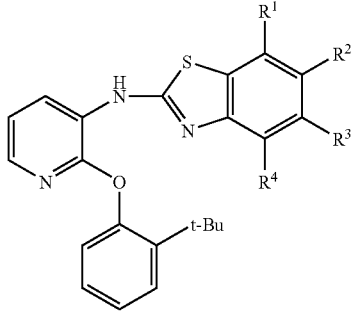
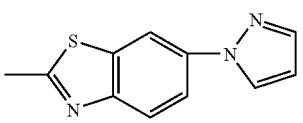
| Example No. | R groups | $t_R$ min | HRMS [M + H]$^+$ |
|---|---|---|---|
| 245 | 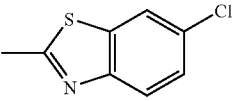 | 7.741 | 442.1711 |
| 246 | 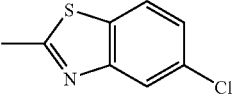 | 8.457 | 410.1089 |
| 247 | 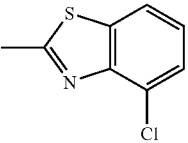 | 8.414 | 410.1107 |
| 248 | 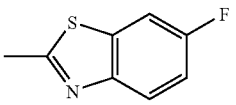 | 8.381 | 410.1098 |
| 249 | 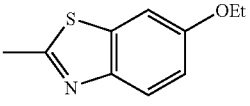 | 8.067 | 394.1373 |
| 250 | 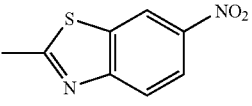 | 8.114 | 420.1732 |
| 251 | | 8.091 | 421.1352 |
| 252 | 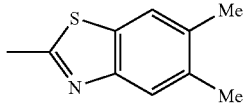 | 8.374 | 404.1797 |

TABLE 6-continued
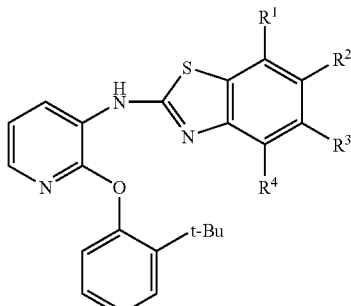
| Example No. | | $t_R$ min | HRMS [M + H]⁺ |
|---|---|---|---|
| 253 | 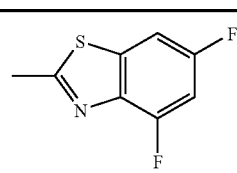 | 8.267 | 412.1279 |
| 254 | 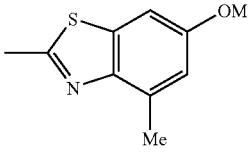 | 8.497 | 420.1727 |
| 255 | 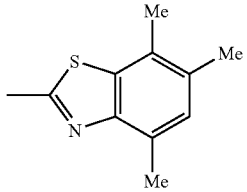 | 9.28 | 418.1945 |
| 256 | 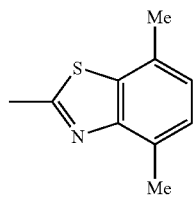 | 8.92 | 404.1785 |
| 257 | 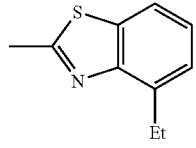 | 8.87 | 404.1799 |
| 258 | 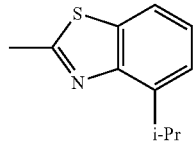 | 9.06 | 410.1098 |

TABLE 6-continued
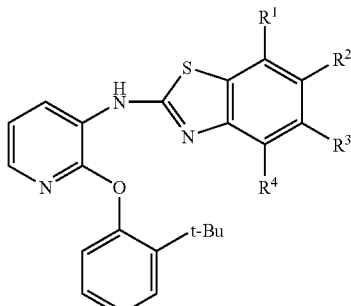
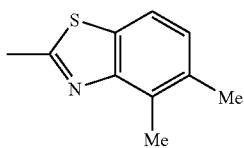
| Example No. | R⁴ | $t_R$ min | HRMS [M + H]⁺ |
|---|---|---|---|
| 259 | 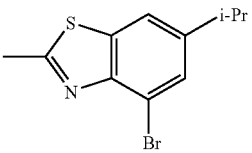 | 8.894 | 404.1800 |
| 260 | 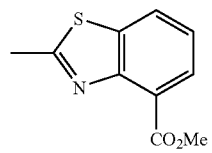 | 9.357 | 496.1042 |
| 261 | 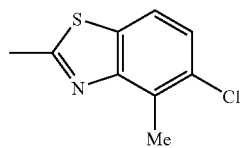 | 8.204 | 434.1546 |
| 262 | 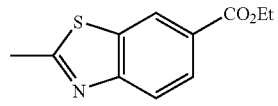 | 9.134 | 424.1231 |
| 263 | 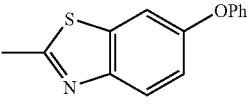 | 8.301 | 448.1705 |
| 264 | 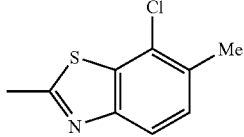 | 8.637 | 468.1733 |
| 265 | | 8.701 | 424.1242 |

TABLE 6-continued

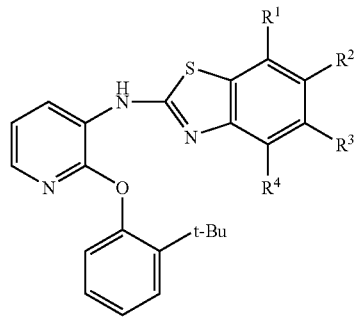

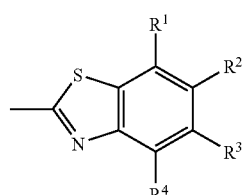

| Example No. | R⁴ | $t_R$ min | HRMS [M + H]⁺ |
|---|---|---|---|
| 266 | 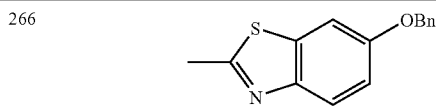 | 8.571 | 482.1889 |
| 267 | 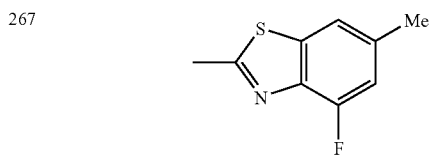 | 8.287 | 408.1534 |

Example 231

N-(2-(2-tert-Butylphenoxy)pyridine-3-yl)benzo[d]thiazol-2-amine

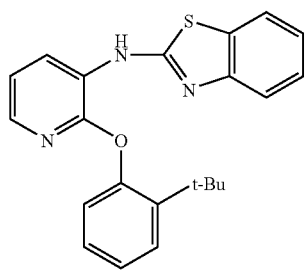

231

111 mg (0.39 mmol) of the isothiocyanate 1c was mixed with 49 mg (0.39 mmol) of thiophenol and 3 mL of dry pyridine. The reaction mixture was stirred at rt under $N_2$ atmosphere for 3 days. 3 mL of cold water were added and the suspension was extracted with $CH_2Cl_2$, dried over $MgSO_4$ and evaporated to yield a dark oil. This crud material was purified by isco system flash chromatography (continuous gradient from 0% B to 20% B over 15 min; A=Hexane; B=EtOAc) followed by a preparative HPLC purification (continuous gradient from 50% B to 100% B over 15 min; A=90:10:0.1 $H_2O$:MeOH:TFA; B=90:10:0.1 MeOH:$H_2O$:TFA) to yield Example 231. $t_R$=7.881 min (Shimadzu Phenomenex S5 ODS 4.6×50 mm Luna 4.6×50 mm; flow rate 2.5 mL/mn; detection at 220 mM; Gradient elution 0% to 100% B over 8 min; (A=10% MeOH, 90% $H_2O$, 0.2% $H_3PO_4$ & B=90% MeOH, 10% $H_2O$, 0.2% $J_3PO_4$). HRMS (ESI) m/z calcd for $C_{22}H_{22}N_3OS$ [M+H]⁺ 376.1484, found 376.1497.

Example 232

N-(2-(2-tert-Butylphenoxy)pyridine-3-yl)-5-(trifluoromethyl)benzo[d]thiazol-amine

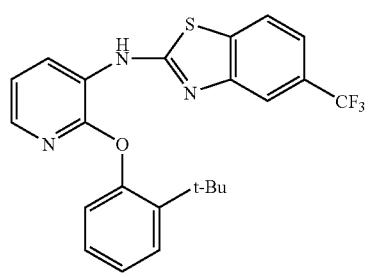

232

111 mg (0.39 mmol) of the isothiocyanate 1c was mixed with 89.6 mg (0.39 mmol) of 3-amino-4-mercaptobenzotrifluoride, HCl and 5 mL of dry pyridine. The reaction mixture was refluxed under $N_2$ atmosphere for 3 days. 5 mL of ice/water were added and the gummy compound was extracted with $CH_2Cl_2$, dried over $MgSO_4$ and evaporated to yield a brown oil. This crud material was purified by ISCO system flash chromatography (continuous gradient from 0% B to 50% B over 20 min; A=Hexane; B=EtOAc) followed by a preparative HPLC purification (continuous gradient from 60% B to 100% B over 15 min; A=90:10:0.1 H₂O:MeOH:TFA; B=90:10:0.1 MeOH:H₂O:TFA) to yield Example 232. $t_R$=8.451 min (Shimadzu Phenomenex 55 ODS 4.6×50 mm Luna 4.6×50 mm; flow rate 2.5 mL/mn; detection at 220 nM; Gradient elution 0% to 100% B over 8 min; (A=10% MeOH, 90% H₂O, 0.2% H₃PO₄ & B=90% MeOH, 10% H₂O, 0.2% H₃PO₄). HRMS (ESI) m/z found for C₂₃H₁₂F₃N₃OS [M+H]⁺ 444.1344.

Example 233

N-(2-(2-tert-Butylphenoxy)pyridine-3-yl)-6-methoxybenzo[d]thiazol-2-amine

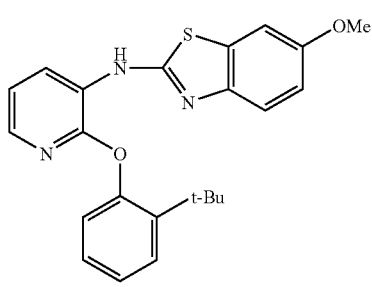

233

100 mg (0.38 mmol) of 1-imino-6-methoxybenzothiazole and 1b were heated under N₂ atmosphere at 220° C. for 30 min, in a similar manner to 234a. After cooling to rt, the reaction mixture was suspended in MeOH and the side product bis(6-methoxybenzo[d]thiazol-2-yl)amine (46.3 mg) was eliminated by filtration. The mother liquors were purified by preparative HPLC to yield Example 233. $t_R$=7.861 min (Shimadzu Phenomenex S5 ODS 4.6×50 mm Luna 4.6×50 mm; flow rate 2.5 mL/mn; detection at 220 nM; Gradient elation 0% to 100% B over 8 min; (A=10% MeOH, 90% H₂O, 0.2% H₃PO₄ & B=90% MeOH, 10% H₂O, 0.2% H₃PO₄). HRMS (ESI) m/z calcd for C₂₃H₂₄N₃O₂S [M+H]⁺ 406.1589. found 406.1576.

Example 234

N-(2-(2-tert-Butylphenoxy)pyridine-3-yl)-6-isopropylbenzo[d]thiazol-2-amine

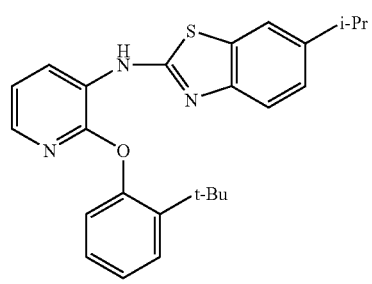

234

234a. 6-Isopropylbenzo[d]thiazol-2-amine

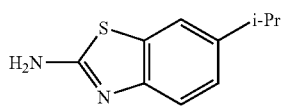

234a 2.7 g (0.02 mol) of 4-isopropylaniline and 3.2 g (0.04 mol) of NaSCN were dissolved in 30 mL of glacial acetic acid. To this solution cooled with ice/water was added dropwise (so that 0° C.<10° C.), a solution of Br₂ (3.2 g) in 5 mL of glacial acetic acid. The color of the reaction mixture darkened and a precipitate was formed. The mixture was stirred at rt for the night. Acetic acid was removed under vacuum. Water (20 mL) was added and the pH made alkaline with 1N NaOH solution. Aqueous phase was extracted with CH₂Cl₂, dried over MgSO₄ and concentrated to yield 4 g of an oil. 234a (1.9 g) was obtained after purification by flash chromatography ISCO system (loading with EtOAc/Hexane 50:50 and eluting with gradient EtOAc/Hexane 0% to 100%). $t_R$=1.96 min (over 4 min run) [M+H]⁺=193.22. ¹H NMR (400 MHz, CDCl₃) δ ppm 1.26 (d, 6H), 2.96 (m, 1H), 5.4 (bs, 1H), 7.15 (d, 1H), 7.45 (m, 3H).

234b. 2-(2-tert-Butylphenoxy)pyridine-3-ylboronic acid

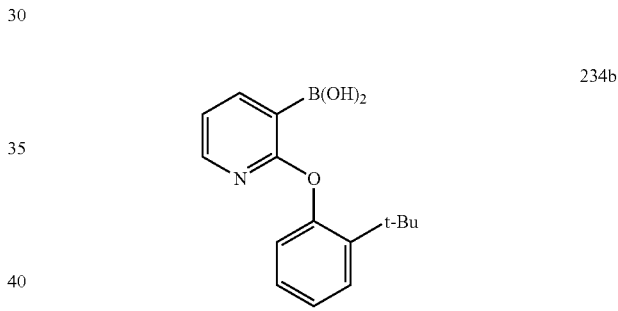

234b

To a solution of 141a (3.35 g, 9.49 mmol) in THF (60 ml) under nitrogen at −78° C. was added 2.0 M nBuLi in pentane (14.2 mL, 28.47 mmol, 3 eq) over ~3 min. The reaction was stirred at −78° C. for 10 min & then B(OiPr)₃ (6.54 mL, 28.47 mmol, 3 eq) was added in a single aliquot. The reaction was stirred at −78° C. for 40 min and then the reaction was poured into water (~60 mL) followed by the addition of LiOH (~3.5 g). The reaction was stirred for 2 h at rt. Partition the reaction mixture between water (~200 mL additional) and EtOAc (~200 mL). Separate layers and wash the aqueous once more with EtOAc. Pour aqueous into a large erlenmyer flask & add EtOAc (~200 mL). With vigorous stirring add conc. HCl dropwise until pH ~2. Separate layers in sep. funnel & extract aqueous once more with EtOAc (~200 mL). Combine these last two EtOAc extracts, dry over sodium sulfate, filter and concentrate. Azeotrope twice with toluene to give 234b (2.38 g) as a white solid. ¹H NMR (400 MHz, CDCl₃) δ ppm 1.31 (s, 9H); 4.1 (bs, 1H); 5.61 (bs, 1H); 6.91 (d, J=7.47 Hz, 1H); 7.05 (dd, J=6.37, 3.74 Hz, 1H); 7.15-7.3 (m, 2H); 7.48 (dd J=7.47, 1.32 Hz, 1H); 8.23 (bs, 1H); 8.27 (dd, J=7.03 Hz, 1H).

Example 234

To a solution of 234a (19.2 mg, 0.1 mmol), in dichloromethane (2 mL) in a scintillation vial were added 27.1 mg (0.1 mmol) of the boronic acid 234b prepared as above. Next 100 µL of TEA and finally 18.3 mg (0.1 mmol) of Cu(Oac)$_2$ were introduced and the vessel was capped. The reaction mixture was microwaved at 100° C. for 30 min (Apparatus name). The dark suspension was filtered through celite 454 and Example 234 isolated after preparative HPLC. $t_R$=8.644 min (Shimadzu Phenomenex 55 ODS 4.6×50 mm Luna 4.6× 50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{25}$H$_{28}$N$_3$OS [M+H]$^+$ 418.1953. found 418.1936.

Example 235

N-(2-(2-tert-Butylphenoxy)pyridine-3-yl)benzo[d]thiazol-6-amine

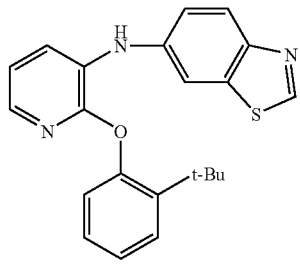

235

According to the experimental procedure of Example 234, Example 235 was obtained by reacting 234b with 6-aminobenzothiazole. $t_R$=7.344 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{22}$H$_{22}$N$_3$OS [M+H]$^+$. found 376.

Examples 236 to 237

Examples 236 to 267 listed in Table 6 above were prepared by reacting the appropriated reagents according to one of the methods described in Examples 225, 231, 233 and 234.

Example 268

N-(2-(2-(2-tert-Butylphenoxy)pyridine-3-ylamino)benzo[d]oxazol-4-yl)-2-phenoxyacetamide

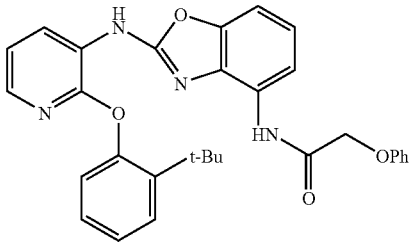

268

16 mg (0.0427 mmol) of Example 139 was dissolved in 1 mL of anhydrous CH$_2$Cl$_2$. The solution was cooled to 0° C. and 0.1 mL of TEA was added followed by 0.0513 mmol of phenoxyacetyl chloride. The mixture was stirred at rt for 2 h, solvent evaporated and crude material purified by preparative HPLC (continuous gradient from 50% B to 100% B; A=90:10:0.1 H$_2$O:MeOH:TFA; B=90:10:0.1 MeOH:H$_2$O:TFA) to yield Example 268. $t_R$=8.324 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{30}$H$_{29}$N$_4$O$_4$ [M+H]$^+$ 509.2189. found 509.2119.

Examples 269 to 284

Examples 269 to 284 listed in Table 7 were prepared by reacting the appropriated reagents according to the procedure described in Examples 268.

TABLE 7

| Example No. | R$^1$ | R$^2$ | R$^3$ | R$^4$ | $t_R$ min | HRMS [M + H]$^+$ |
|---|---|---|---|---|---|---|
| 269 | | | | (HN-C(=O)-cyclopropyl) | 7.56 | 443.2069 |

TABLE 7-continued
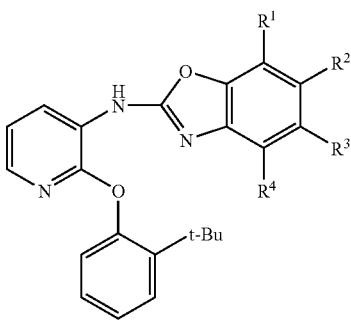
| Example No. | | $t_R$ min | HRMS [M + H]⁺ |
|---|---|---|---|
| 270 | 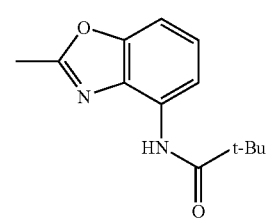 | 7.91 | 459.2390 |
| 271 | 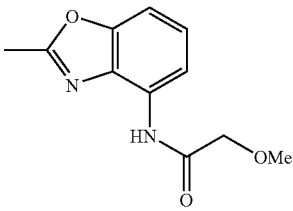 | 7.53 | 469.1838 |
| 272 |  | 7.508 | 481.1916 |
| 273 | 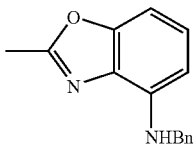 | 8.527 | 465.2276 |
| 274 | 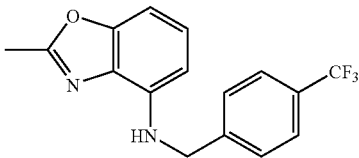 | 8.747 | 533.2161 |

TABLE 7-continued
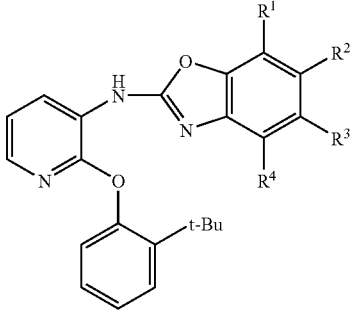
| Example No. | | $t_R$ min | HRMS [M + H]$^+$ |
|---|---|---|---|
| 275 | 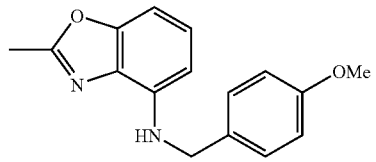 | 8.362 | 495.2413 |
| 276 | 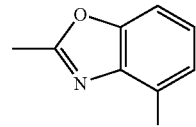 | 7.32 | 389.1971 |
| 277 | 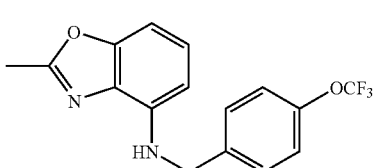 | 8.82 | 549.2101 |
| 278 | 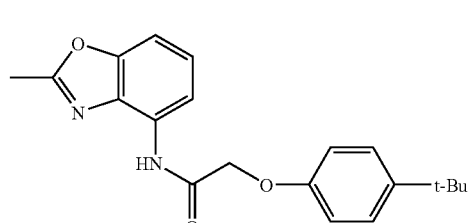 | 9.18 | 565.2796 |
| 279 | 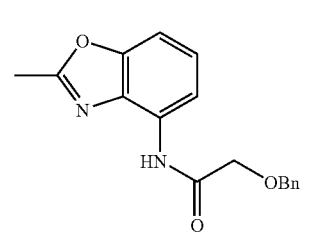 | 8.345 | 523.2338 |

TABLE 7-continued
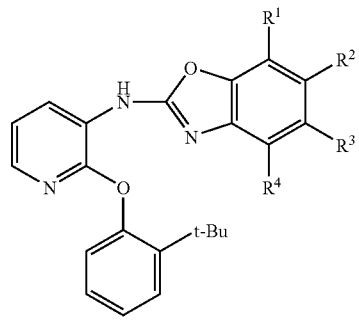
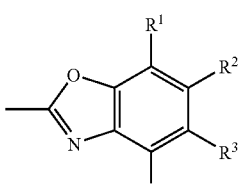
| Example No. | | $t_R$ min | HRMS [M + H]+ |
|---|---|---|---|
| 280 | 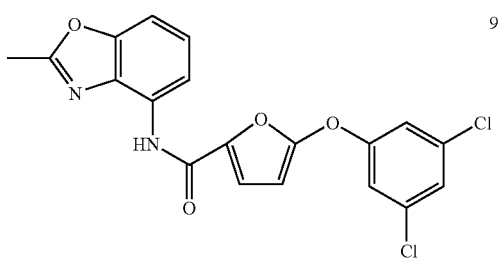 | 9.204 | 629.1330 |
| 281 | 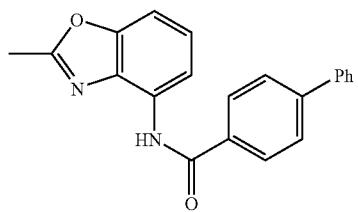 | 8.524 | 555.2390 |
| 282 | 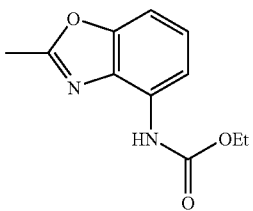 | 7.877 | 447.2028 |
| 283 | 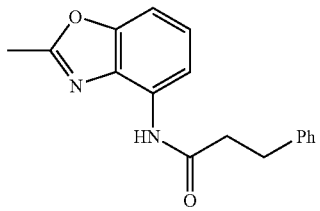 | 8.025 | 507.2392 |

TABLE 7-continued

| Example No. | R⁴ | t_R min | HRMS [M + H]⁺ |
|---|---|---|---|
| 284 | | 8.763 | 571.2118 |

Example 285

N-{2-[[2-(2-tert-Butyl-phenoxy)-pyridin-3-yl]-(3-phenyl-propionyl)-amino]-benzooxazol-4-yl}-3-phenyl-propionamide

285

Example 285 was prepared by reacting the appropriated reagent according to the procedure described in Example 268. $t_R$=8.497 min; [M+H]⁺ found 639.2959.

Examples 286 to 289

Examples 286 to 289 were prepared according to one of the methods described above:

| Example No. | R⁴ | t_R min | HRMS [M + H]⁺ |
|---|---|---|---|
| 286 | 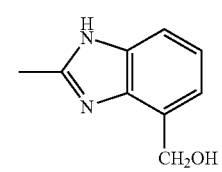 | 4.457 | 389.1988 |

-continued

| Example No. | R⁴ | $t_R$ min | HRMS [M + H]⁺ |
|---|---|---|---|
| 287 | (2-methyl-1H-benzimidazol-4-yl)-CO₂H | 5.188 | 403.1784 |
| 288 | (2-methyl-1H-benzimidazol-5-yl)-vinyl | 5.388 | 385.2014 |
| 289 | (2-methyl-1H-benzimidazol-4-yl)-CH(Me)OH | 5.473 | 403.2133 |

Example 290

Allyl 2-(2-(2-tert-butylphenoxy)pyridin-3-ylamino)-1H-benzo[d]imidazole-5-carboxylate

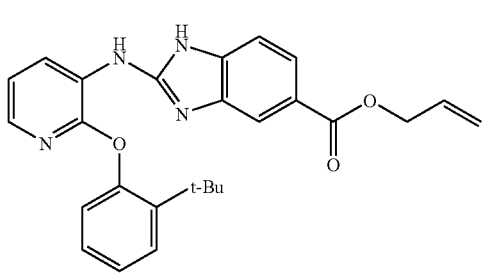

290

100 mg (0.249 mmol) of Example 146 was suspended in 4 mL of CH₂Cl₂/Toluene (1:1 ratio). Thionyl chloride (72 µL) was introduced and the mixture refluxed for 3.5 h. Volatiles were evaporated under vacuum, the traces of SOCl₂ eliminated by coevaporation with CH₂Cl₂ (2×4 mL) to yield the intermediate acid chloride 290a as a white solid used in the next step without further purification.

26 mg (0.0618 mmol) of 290a was suspended in 1 mL of anhydrous THF. 8.4 µL (0.125 mmol) of prop-2-en-1-ol was introduced and the mixture stirred at rt overnight then heated at 50° C. for 3 h. Volatiles were evaporated and the residue purified by preparative HPLC (continuous gradient from 40% B to 75% B; A=90:10:0.1 H₂O:MeOH:TFA; B=90:10:0.1 MeOH:H₂O:TFA) to yield the desired product. $t_R$=6.06 min (Shimadzu Phenomenex S5 ODS 4.6×50 mm Luna; flow rate 2.5 mL/mn; detection at 220 nM; Gradient elution 0% to 100% B over 8 min; (A=10% MeOH, 90% H₂O, 0.2% H₃PO₄ & B=90% MeOH, 10% H₂O, 0.2% H₃PO₄). HRMS (ESI) m/z calcd for C₂₆H₂₇N₄O₃ [M+H]⁺ 443.2083. found 443.2093.

Example 291

Neopentyl 2-(2-(2-tert-butylphenoxy)pyridin-3-ylamino)-1H-benzo[d]imidazole-5-carboxylate

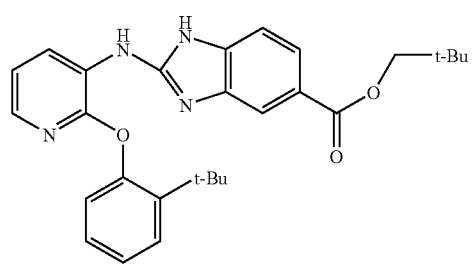

291

Example 291 was prepared using the procedure of Example 290. $t_R$=6.801 min (Shimadzu Phenomenex S5 ODS 4.6×50 mm Luna; flow rate 2.5 mL/mn; detection at 220 nM; Gradient elution 0% to 100% B over 8 min; (A=10% MeOH, 90% H₂O, 0.2% H₃PO₄ & B=90% MeOH, 10% H₂O, 0.2% H₃PO₄). HRMS (ESI) m/z calcd for C₂₈H₃₃N₄O₃ [M+H]⁺ 473.2553. found 473.2563.

Example 292

2-(2-(2-tert-Butylphenoxy)pyridin-3-ylamino)-1H-benzo[d]imidazole-4-carbonitrile

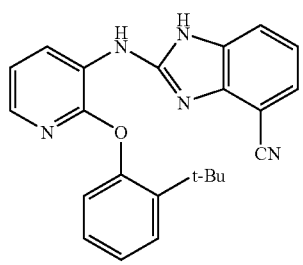

292

65 mg (0.162 mmol) of [2-(2-(2-tert-butylphenoxy)pyridin-3-ylamino)-1H-benzo[d]imidazole-4-carboxamide] (Example 163) was mixed with 3 mL of pyridine and 22 mg (0.32 mmol) of imidazole. The solution was cooled to −30° C. and 60 μL of POCl₃ were added dropwise. Stirring continued at −20° C. for 2 h. Volatiles were evaporated. The reaction mixture was filtered through silica gel (eluting EtOAc/Hexane 40%) and purified by preparative HPLC. (continuous gradient from 50% B to 100% B; A=90:10:0.1 H₂O:MeOH:TFA; B=90:10:0.1 MeOH:H₂O:TFA) to yield the desired product. R=6.663 min (Shimadzu Zorbax SB C18 4.6×50 mm; flow rate 2.5 mL/mn; detection at 220 nM; Gradient elution 0% to 100% B over 8 min; (A=10% MeOH, 90% H₂O, 0.2% H₃PO₄ & B=90% MeOH, 10% H₂O, 0.2% H₃PO₄). HRMS (ESI) m/z calcd for C₂₃H₂₂N₅O [M+H]⁺ 384.18245. found 384.1840.

Example 293

2-(2-(2-(2-tert-Butylphenoxy)pyridin-3-ylamino)-1H-benzo[d]imidazol-5-yl)propan2-ol

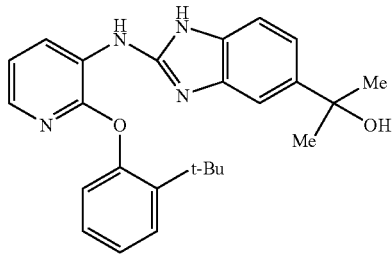

293

To a cooled (0° C.) solution of Example 142 (35 mg, 0.0874 mmol), in 2.5 mL of Et₂O, was added 87 μL (0.262 mmol) of commercial methylmagnesium bromide 3.0M solution in ether. The reaction mixture was stirred overnight at rt, cooled to 0° C. and quenched with 4 mL of saturated NH₄Cl, then with 4 mL of water. The organic phase was separated and the aqueous phase further extracted with ether (3×5 mL) Organic phases were combined, dried over MgSO₄, filtered and concentrated. Purification of the residue by Isco system flash chromatography to yield the desired compound (eluting continuous gradient EtOAc from 0% to 40% in Hexane over 30 min). t$_R$=4.762 min (Shimadzu Phenomenex Luna 4.6×50 mm; flow rate 2.5 mL/mn; detection at 220 nM; Gradient elution 0% to 100% B over 8 min; (A=10% MeOH, 90% H₂O, 0.2% H₃PO₄ & B=90% MeOH, 10% H₂O, 0.2% H₃PO₄). HRMS (ESI) m/z calcd for C₂₅H₂₉N₄O₂ [M+H]⁺ 417.2291. found 417.2273.

Example 294

5-tert-Butyl-N-(2-(2-tert-butylphenoxy)thiophen-3-yl)-1H-benzo[d]imidazol-2-amine

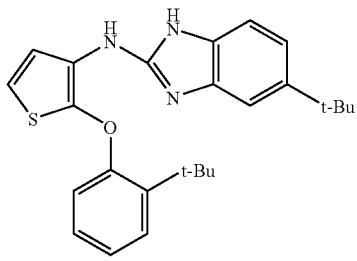

294

294a. 2-(2-tert-Butylphenoxy)-3-nitrothiophene

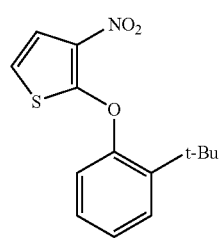

294a

To a solution of 2-chloro-3-nitrothiophene (1.13 g, 6.93 mmol) in NMP (10 mL) in a pressure vessel was added 2-tert-butylphenol (1.04 g, 6.93 mmol) and K₂CO₃ (1.0 g, 10.1 mmol). The reaction was flushed with nitrogen, sealed and then heated to 105° C. for 48 h. The reaction was cooled to rt, diluted with EtOAc (~150 mL) and washed twice with saturated aqueous NaCl (2×~150 mL). The aqueous washes were then back extracted with EtOAc. The combined organics were dried over MgSO₄, filtered and concentrated to yield the crude desired product.

294b. 2-(2-tert-Butylphenoxy)-3-aminothiophene

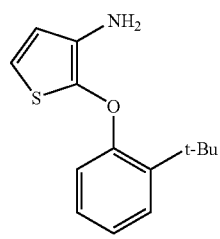

294b

The residue from Example 294a was taken up in THF (50 ml) in a pressure vessel to which was added Raney Ni in water (~300 mg) and a stir bar. The reaction was degassed under mild vacuum and then placed under hydrogen gas (60-65 psi) and then stirred under hydrogen for ~3 h. The reaction vessel was then charged again with hydrogen gas (back to 60-65 psi) and the reaction was stirred overnight. The catalyst was removed by filtration through Celite®, taking care not to allow the cake to dry and the solid catalyst to ignite. The Celite® pad was washed with THF until no UV activity was observed in the eluent. Purification by flash chromatography (110 g ISCO silica cartridge, 0 to 15% EtOAc in hexanes over 40 min, hold at 15% EtOAc in hexanes for 10 min., 50 ml/min) provided Example 294b (2.0 g). (M+H)$^+$=248.3.

294c. 2-(2-tert-Butylphenoxy)-3-isothiocyanatothiophene

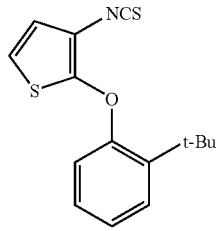

A solution of Example 294b (14.84 mg, 0.0600 mmol) in anhydrous DCM (1.0 ml) was added portionwise to a cold solution of thiocarbonyl diimidazole (21.39 mg, 0.1200 mmol) in anhydrous DCM (0.50 ml). The reaction was shaken at 0° C. for 1 hour and then warmed to rt with stirring for 2 h. The reaction solution was concentrated down. The resulting residue was dissolved into a minimum amount of DCM and loaded onto a SPE tube containing 2.0 g of silica. The product was eluted using 10-20% EtOAc in Hexanes to afford 294c.

Example 294

To a solution of Example 294c (0.060 mmol) in DCE (1 mL) was added 0.50 ml of a 0.24 M stock solution of 4-(tert-butyl)-1,2-diaminobenzene in DCE. The reaction was stirred at room temperature for 6.5 h. 0.50 ml of a 0.24 M stock solution of EDC in DCM was added and the reaction was stirred overnight at rt. The cyclization was not complete, so an additional 0.50 ml of 0.24 M stock solution of EDC in DCM was added. The reaction was shaken at rt for 5 h and then concentrated down. Purification by preparative HPLC (continuous gradient from 20% B to 100% B; A=90:10:0.1 H$_2$O:CH$_3$CN:TFA; B=90:10:0.1 CH$_3$CN:H$_2$O:TFA) afforded Example 294 (1.12 mg) as a yellow oil. [M+H]$^+$=420.13.

Example 295

N-(2-(2-tert-Butylphenoxy)pyridin-3-yl)-6-(1-methoxyethyl)benzo[d]thiazol-2-amine

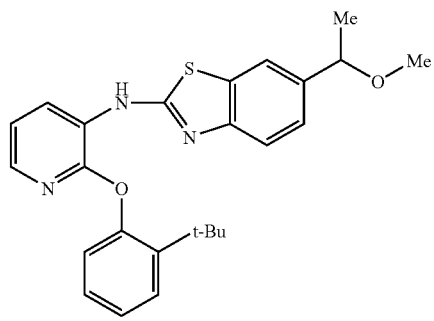

Example 295 was obtained by the reaction of MeOH with example 227 according to the method of example 144. t$_R$=8.188 min (Shimadzu Zorbax SB C18 4.6×75 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). (ESI) m/z [M+H]$^+$ 434.2. $^1$H NMR (500 MHz, CD$_3$OD) δ ppm 1.33 (m, 9H), 1.35 (d, J=6.6 Hz, 3H), 3.22 (s, 3H), 4.41 (q, J=6.6 Hz, 1H), 6.96 (dd, J=8.25, 1.6 Hz, 1H), 7.15-7.25 (m, 3H), 7.36 (dd, J=8.25, 1.65 Hz, 1H); 7.46 (dd, J=8.25, 1.65 Hz, 1H), 7.58 (d, J=8.25 Hz, 1H), 7.72 (d, J=1.1 Hz, 1H); 7.85 (dd, J=4.95, 1.65 Hz, 1H), 8.71 (dd, J=1.65; 7.7 Hz, 1H).

Example 296 tert-Butyl 6-bromobenzo[d]thiazol-2-yl(2-(2-tert-butylphenoxy)pyridin-3-yl)carbamate

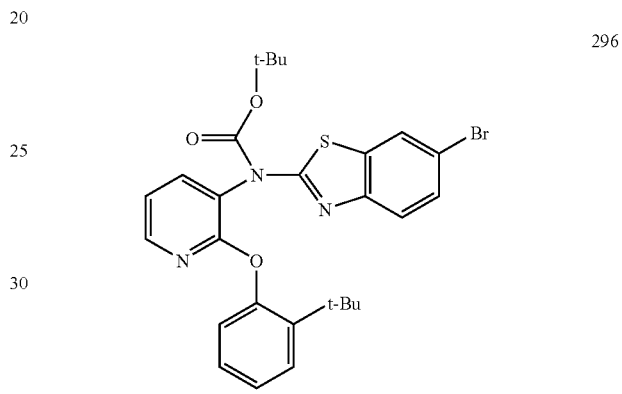

91 mg (0.2 mmol) of Example 236, 50 mg (0.23 mmol) of di-t-Butyldicarbonate, 25 mg (0.2 mmol) of DMP and 5 mL of CH2Cl2 were mixed and stirred overnight at rt. 2 mL of water was added, organic phase separated dried over MgSO4 and evaporated to yield 142.6 mg of the desired product as a crude amorphous solid. Further purification by preparative HPLC (Eluting with continuous gradient from 75% B to 100% B; A=90:1 H$_2$O:MeOH; B=90:10 MeOH:H$_2$O) yield Example 296. t$_R$=8.784 min (Shimadzu Phenomenex S5 ODS 4.6×50 mm Luna 4.6×50 mm; flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). (ESI) m/z [M+H]$^+$ 555.2.

Utility

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated or cured by the administration of an anti-platelet agent. Thus, the compounds of the present invention are useful in the treatment or prevention of various platelet associated disorders including: Thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequences of surgery, interventional cardiology or immobility; thromboembolic consequences of medication (such as oral contraceptives, hormone replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic never transmission would be of therapeutic benefit such as nociception or neuronal tissue regeneration. These and many other potential utilities for P2Y$_1$ antagonists have been recently reviewed (Burnstock, G. and Williams, M. *J. Pharm. Exp Ther.* 2000, 295, 862-9) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

P2Y$_1$ Assays

Binding Assay

A membrane binding assay was used to identify inhibitors of [$^{33}$P] 2MeS-ADP binding to cloned human P2Y$_1$ receptors. The cDNA clone for human P2Y$_1$ was obtained from Incyte Pharmaceuticals and its sequence confirmed by established techniques (for a compendium of techniques used see Ausubel, F. et al. *Current Protocols in Molecular Biology* 1995 John Wiley and Sons, NY, N.Y.). The essential coding sequences were subcloned into pCDNA 3.1 (Invitrogen) to produce a P2Y$_1$ expression construct. This construct was then transfected into the human embryonic kidney cell line HEK-293 and stable transfectants selected in Genetcin® (G418 sulfate; Life Technologies). Several lines were screened for binding activity and one (HEK293 #49) selected for further characterization. Membranes were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM MgCl$_2$ containing Complete® protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl 0.1 mM MgCL$_2$, 5 mM EDTA, 5 mM KCl) and stored at −70° C. until used.

Binding reactions were performed in WGA FlashPlates (PerkinElmer Life Sciences, Cat #SMP105A) in a volume of 200 μL containing ~45 fmol of P2Y$_1$ receptor (5 μg of total protein), 0.5 nM [$^{33}$P] 2MeS-ADP (PerkinElmer; 2,000 Ci/mmol), and various concentrations of the test compound (usually between 50 μM and 10 pM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

Compounds tested in the P2Y$_1$ binding assay are considered to be active if they exhibit a K$_i$ of equal to or less than 10 μM. Preferred compounds of the present invention have K$_i$'s of equal to or less than 1 μM. More preferred compounds of the present invention have K$_i$'s of equal to or less than 0.1 μM. Even more preferred compounds of the present invention have K$_i$'s of equal to or less than 0.01 μM. Compounds of the present invention have demonstrated K$_i$ values of equal to or less than 10 μM in the assay for P2Y$_1$ binding, thereby confirming that they act to modulate P2Y$_1$ activity.

The compounds of the present invention may be used in combination with each other, or with other anti-platelet agents. Additionally, the present compounds may be used in combination with one or more of various other therapeutic agents, including: anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phosphodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in U.S. Application Publication US 20030022890.

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable anti-platelet agents for use in combination with the compounds of the present invention include: GPIIb/IIIa blockers (e.g., abciximab, eptifibatide, tirofiban, integrelin); other P2Y$_{12}$ antagonists (e.g., clopidogrel, ticlopidine, Prasugrel); thromboxane receptor antagonists (e.g., ifetroban); aspirin; and PDE-III inhibitors (e.g., dipyridamole) with or without aspirin.

Examples of suitable anti-thrombotic and/or anti-thrombolytic agents for use in combination with the compounds of the present invention include: tissue plasminogen activator (natural or recombinant), tenecteplase (INK), and lanoteplase (nPA); factor VIIa inhibitors; factor Xa inhibitors; factor XIa inhibitors, thrombin inhibitors (such as hirudin and argatroban); PAI-1 inhibitors (i.e., inactivators of tissue plasminogen activator inhibitors); alpha2-antiplasmin inhibitors; streptokinase, urokinase and prourokinase; and anisoylated plasminogen streptokinase activator complex.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diuretics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phosphodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in U.S. Pat. No. 6,548,529.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epothilones, cisplatin, and carboplatin.

Examples of suitable anti-ulcer and gastroesophageal reflux disease agents for use in combination with the compounds of the present invention include famotidine, ranitidine, and omeprazole.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving platelet ADP receptor. For example, the presence of $P2Y_1$ in an unknown sample could be determined by addition of the relevant radiolabeled compound to the sample and measuring the extend of binding to the $P2Y_1$ receptor.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

What is claimed is:

1. A compound of Formula (Ia):

$$\text{(Ia)}$$

or a stereoisomer or a pharmaceutically acceptable salt thereof, wherein:
ring B is pyridine substituted with 0-3 $R^7$;
X is S;
$R^1$, $R^2$, $R^3$ and $R^4$ are, independently at each occurrence, H, F, Br, I, $OCF_3$, $CF_3$, CN, $NO_2$, $-NR^8R^9$, $-C(O)R^c$, $-C(O)OR^c$, $-C(O)NR^8R^9$, $-NR^{10}C(O)R^d$, $-S(O)_pNR^8R^9$, $-S(O)R^d$, $-S(O)_2R^d$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, or $-(CH_2)_r-C_{3-10}$ carbocycle substituted with 0-3 $R^b$;
Y is $NR^{12}$, O or S;
$R^5$ is a $C_{3-10}$ carbocycle substituted with 0-3 $R^b$;
$R^7$ is H, F, Cl, Br, I, $OCF_3$, $CF_3$, $OR^c$, $SR^c$, CN, $NO_2$, $-NR^8R^9$, $-C(O)R^c$, $-C(O)OR^c$, $-C(O)NR^8R^9$, $-NR^{10}C(O)R^d$, $-S(O)_pNR^8R^9$, $-S(O)R^d$, $-S(O)_2R^d$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, or $-(CH_2)_r-C_{3-10}$ carbocycle substituted with 0-3 $R^b$;
$R^8$ is, independently at each occurrence, H, $C_{1-6}$ alkyl, $C_{1-6}$ alkyl)C(O)—, $-(CH_2)_n$-phenyl, $(C_{1-4}$ alkyl)OC(O)—, $(C_{6-10}$ aryl)-$CH_2$—OC(O)—, $(C_{6-10}$ aryl)-$CH_2$—OC(O)—, $(C_{1-4}$ alkyl)-C(O)O—$(C_{1-4}$ alkyl)-OC(O)—, $(C_{6-10}$ aryl)-C(O)O—$(C_{1-4}$ alkyl)-OC(O)—, $(C_{1-6}$ alkyl)-NHC(O)—, $(C_{6-10}$ aryl)-NHC(O)—, $(C_{6-10}$ aryl)-$(C_{1-4}$ alkyl)-C(O)—, $(C_{1-6}$ alkyl)-$S(O)_2$—, $(C_{6-10}$ aryl)-$S(O)_2$—, or $(C_{6-10}$ aryl)-$(C_{1-4}$ alkyl)-$S(O)_2$—, wherein each of said phenyl and aryl may be substituted with 0-2 $R^g$;
$R^9$ is, independently at each occurrence, H, $C_{1-6}$ alkyl or $-(CH_2)_n$-phenyl;
$R^{10}$ is, independently at each occurrence, H, $C_{1-6}$ alkyl substituted with 0-2 $R^{10a}$, $C_{2-6}$ alkenyl substituted with 0-2 $R^{10a}$, $C_{2-6}$ alkynyl substituted with 0-2 $R^{10a}$, or $-(CH_2)_r-C_{3-10}$ carbocycle substituted with 0-3 $R^e$;
$R^{10a}$ is, independently at each occurrence, H, $C_{1-4}$ alkyl, $OR^c$, Cl, F, Br, I, =O, $CF_3$, CN, $NO_2$, $-C(O)R^c$, $-C(O)OR^c$, $-C(O)NR^8R^9$ or $-S(O)_pR^d$;
$R^{12}$ is H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, $(C_{1-6}$ alkyl)C(O)—, $(C_{3-6}$ cycloalkyl)$C_{1-3}$ alkyl-C(O)—, $(C_{3-6}$ cycloalkyl)C(O)—, phenyl-C(O)—, benzyl-C(O)—, benzyl-$S(O)_2$—, $(C_{1-6}$ alkyl)NHC(O)—, $(C_{1-6}$ alkyl)$_2$NC(O)—, phenyl-NHC(O)—, benzyl-NHC(O)—, (phenyl)($C_{1-6}$ alkyl)NC(O)—, (benzyl) $(C_{1-6}$ alkyl)NC(O)—, $(C_{1-6}$ alkyl)-$S(O)_2$—, phenyl-$S(O)_2$—, or $-(CH_2)_r-C_{3-10}$ carbocycle substituted with 0-3 $R^b$;
$R^a$ is, independently at each occurrence, H, F, $OCF_3$, $CF_3$, $OR^c$, $SR^c$, CN, $-NR^8R^9$, $-C(O)NR^8R^9$, $-NR^{10}C(O)R^b$, $-S(O)_pNR^8R^9$, $-S(O)R^d$ or $-S(O)_2R^d$;
$R^b$ is, independently at each occurrence, H, F, Cl, Br, I, $OR^c$, $SR^c$, CN, $NO_2$, $CF_3$, $-SO_2R^d$, $-NR^8R^9$, $C_{1-6}$ alkyl, $C_{2-6}$ alkenyl, $C_{2-6}$ alkynyl, $C_{3-6}$ cycloalkyl, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-C(O)—, $C_1$-$C_4$ alkyl-O—C(O)— or $C_1$-$C_4$ alkyl-C(O)NH—;
$R^c$ is, independently at each occurrence, H, $C_{1-4}$ alkyl, or $-(CH_2)_r-C_{6-10}$ aryl substituted with 0-2 $R^e$;
$R^d$ is, independently at each occurrence, $CF_3$, OH, $C_{1-4}$ alkoxy, $C_{1-6}$ alkyl, or $-(CH_2)_r-C_{3-10}$ carbocycle substituted with 0-2 $R^e$;
$R^e$ is, independently at each occurrence, H, =O, $OR^g$, F, Cl, Br, I, CN, $NO_2$, $-NR^8R^9$, $-C(O)R^f$, $-C(O)OR^f$, $-NR^8C(O)R^f$, $-C(O)NR^8R^9$, $-SO_2NR^8R^9$, $-NR^8SO_2NR^8R^9$, $-NR^8SO_2-C_{1-4}$ alkyl, $-NR^8SO_2CF_3$, $-NR^8SO_2$-phenyl, $-S(O)_2CF_3$, $-S(O)_p-C_{1-4}$ alkyl, $-S(O)_p$-phenyl, $-(CF_2)_rCF_3$, $C_{1-6}$ alkyl, $C_{2-6}$ alkenyl or $C_{2-6}$ alkynyl;
$R^f$ is, independently at each occurrence, H, $C_{1-6}$ alkyl or $-(CH_2)_n$-phenyl;
$R^g$ is, independently at each occurrence, H, =O, $OR^f$, F, Cl, Br, I, CN, $NO_2$, $-NR^9R^9$, $-C(O)R^h$, $-C(O)OR^h$, $-NR^9C(O)R^h$, $-C(O)NR^9R^9$, $-SO_2NR^9R^9$, $-NR^9SO_2NR^9R^9$, $-NR^9SO_2-C_{1-4}$ alkyl, $-NR^9SO_2CF_3$, $-NR^9SO_2$-phenyl, $-S(O)_2CF_3$, $-S(O)_p-C_{1-4}$ alkyl, $-S(O)_p$-phenyl, $-(CF_2)_rCF_3$, $C_{1-6}$ alkyl, $C_{2-6}$ alkenyl or $C_{2-6}$ alkynyl;
$R^h$ is, independently at each occurrence, H, $C_{1-6}$ alkyl or $-(CH_2)_n$-phenyl;
n, at each occurrence, is selected from 0, 1, 2, 3 and 4;
p, at each occurrence, is selected from 0, 1 and 2; and
r, at each occurrence, is selected from 0, 1, 2, 3 and 4.

2. A compound according to claim 1 wherein:
$R^1$, $R^2$, $R^3$, and $R^4$ are, independently at each occurrence, H, F, Br, I, $OCF_3$, $CF_3$, $-CF_2CF_3$, $-(CR^fR^f)_t-OR^c$, CN, $NO_2$, $-(CR^fR^f)_r-NR^8R^9$, $-(CR^fR^f)_r-C(O)R^c$, $-(CR^fR^f)_r-C(O)OR^c$, $-(CR^fR^f)_r-C(O)NR^8R^9$, $-C(O)NR^8(CR^fR^f)_nNR^8R^9$, $-NR^{10}(CR^fR^f)_nC(O)R^d$, $-NR^{10}CO(C R^fR^f)_nOR^c$, $-S(O)_pNR^8R^9$, $-NR^{10}S(O)_pR^d$, $-S(O)R^d$, $-S(O)_2R^d$, $-N(C_{1-4}$ alkyl)$_3^+Cl^-$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, or $-(CR^fR^f)_r-C_{3-10}$ carbocycle substituted with 0-3 $R^b$.

3. A compound according to claim 2, wherein:
one of the $R^1$, $R^2$, $R^3$ and $R^4$ groups is $-(CR^fR^f)_t-OR^c$, $-(CR^fR^f)_r-OR^c$, $-(CR^fR^f)_r-NR^8R^9$, $-(CR^fR^f)_r-C(O)OR^c$, $-(CR^fR^f)_r-C(O)NR^8R^9$, $-C(O)NR^8(CR^fR^f)_nNR^8R^9$, $-NR^{10}(CR^fR^f)_nC(O)R^d$ or $-NR^{10}CO(CR^fR^f)_nOR^c$;
remaining of the $R^1$, $R^2$, $R^3$ and $R^4$ groups are, independently at each occurrence, H, F, Br, I, $OCF_3$, $CF_3$, $-CF_2CF_3$, $-(CR^fR^f)_t-OR^c$, CN, $NO_2$, $-(CR^fR^f)_r-NR^8R^9$, $-(CR^fR^f)_r-C(O)R^c$, $-(CR^fR^f)_r-C(O)OR^c$, $-S(O)_pNR^8R^9$, $-R^{10}S(O)_pR^d$, $-S(O)R^d$, $-S(O)_2R^d$, $-N(C_{1-4}$ alkyl)$_3^+Cl^-$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, or $-(CR^fR^f)_r-C_{3-10}$ carbocycle substituted with 0-3 $R^b$.

4. A compound according to claim 3, wherein:

one of the $R^1$, $R^2$, $R^3$ and $R^4$ groups is NHBn, —NH(4-OMe-Bn), —NH(4-CF$_3$-Bn), —NH(4-OCF$_3$-Bn), CO$_2$Et, —CO$_2$-neopentyl, —CO$_2$CH$_2$CH=CH$_2$, —CH(Me)OCH$_2$C(Me)$_2$CH$_2$NMe$_2$, —CH(Me)OBn, —CH(Me)O(4-i-Pr-Bn), —CH(Me)O(3-CF$_3$-Bn), —CH(Me)O(4-CF$_3$-Bn), —CH(Me)O(4-OPh-Bn), —CH(Me)O(3,5-diCl-Bn), —CH$_2$NHBn, —CH$_2$NH(4-CF$_3$-Bn), —CH$_2$N(Me)Bn, —CH(Me)N(Me)(i-Bu), —CH(Me)N(Me)Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me)(3-CF$_3$-Bn), —CH(Me)N(Me)(4-CF$_3$-Bn), —CH(Me)N(Me)(3,4-diCl-Bn), —CH(Me)N(Me)CH$_2$CH$_2$Ph, —CH(Me)N(t)Bn, —CH(Me)N(Et)(4-Me-Bn), —CH(Me)N(Et)(2-Cl-Bn), —CH(Me)N(Bn)CH$_2$CN, —CH(Me)N(Bn)CH$_2$CH$_2$OH, —CH(Me)N(Bn)CH$_2$CO$_2$Me, —CH(Me)N(Bn)CH$_2$CONMe$_2$, —CH(Me)N(Bn)CH$_2$CON(Me)(Bn), —CONH-neopentyl, —CONHBn, —CONH(4-CF$_3$-Bn), —CONH(4-NO$_2$-phenethyl), —CONHCH$_2$CH$_2$NHPh, —NHCOCH$_2$OBn, —NHCOCH$_2$O-(4-t-Bu-Ph), —NHCO(4-Ph-Ph), or —NHCOC(Me)$_2$O(–4-Cl-Ph).

5. A compound according to claim 2, wherein:

ring B is pyridine substituted with 0-2 $R^7$;

$R^8$ is, independently at each occurrence, H, $C_{1-6}$ alkyl substituted with 0-2 $R^j$, —C(O)$R^k$, —C(O)O$R^k$, —C(O)NR$^i$R$^i$, —S(O)$_2$R$^k$, or —(CR$^f$R$^f$)$_r$—C$_{3-10}$ carbocycle substituted with 0-2 $R^j$;

$R^9$ is, independently at each occurrence, H, $C_{1-4}$ alkyl or —(CH$_2$)$_n$-phenyl; and $R^{10}$ is, independently at each occurrence, H, $C_{1-6}$ alkyl substituted with 0-2 $R^{10a}$, $C_{2-6}$ alkenyl substituted with 0-2 $R^{10a}$, $C_{2-6}$ alkynyl substituted with 0-2 $R^{10a}$, or —(CH$_2$)$_r$-phenyl substituted with 0-3 $R^e$.

6. A compound according to claim 4, wherein:

Y is O or S;

$R^5$ is phenyl with 0-3 $R^b$;

$R^{10}$ is, independently at each occurrence, H, $C_{1-4}$ alkyl, phenyl or benzyl; and $R^{11}$ is H, $C_{1-4}$ alkyl, $C_{2-4}$ alkenyl, $C_{2-4}$ alkynyl, ($C_{1-4}$ alkyl)C(O)—, benzyl-C(O)—, benzyl-S(O)$_2$—, ($C_{1-4}$ alkyl)-S(O)$_2$— or benzyl.

7. A compound according to claim 1, wherein the compound is selected from the group consisting of:

N-(2-(2-tert-butylphenoxy)pyridin-3-yl)-6-methylbenzo[d]thiazol-2-amine;

N-(2-(2-tert-butylphenoxy)pyridin-3-yl)-5-methylbenzo[d]thiazol-2-amine;

N-(2-(2-tert-butylphenoxy)pyridin-3-yl)-7-methylbenzo[d]thiazol-2-amine;

6-tert-butyl-N-(2-(2-tert-butylphenoxy)pyridin-3-yl)benzo[d]thiazol-2-amine;

5-tert-butyl-N-(2-(2-tert-butylphenoxy)pyridin-3-yl)benzo[d]thiazol-2-amine;

7-tert-butyl-N-(2-(2-tert-butylphenoxy)pyridin-3-yl)benzo[d]thiazol-2-amine;

N-(2-(2-tert-butylphenoxy)pyridin-3-yl)-6-(trifluoromethyl)benzo[d]thiazol-2-amine;

N-(2-(2-tert-butylphenoxy)pyridin-3-yl)-6-(trifluoromethoxy)benzo[d]thiazol-2-amine;

N-(2-(2-tert-butylphenoxy)pyridin-3-yl)-6-phenylbenzo[d]thiazol-2-amine;

N-(2-(2-tert-butylphenoxy)pyridin-3-yl)naphtho[1,2-d]thiazol-2-amine;

N-(2-(2-tert-butylphenoxy)pyridin-3-yl)-4,6-dimethylbenzo[d]thiazol-2-amine;

N-(2-(2-tert-butylphenoxy)pyridin-3-yl)-4,6-dichlorobenzo[d]thiazol-2-amine;

N-(2-(2-tert-butylphenoxy)pyridin-3-yl)-4-methyl-6-(trifluoromethoxy)benzo[d]thiazol-2-amine;

1-(2-(2-(2-tert-butylphenoxy)pyridine-3-ylamino)benzo[d]thiazol-6-yl)ethanone;

2,2-dibromo-1-(2-(2-(2-tert-butylphenoxy)pyridine-3-ylamino)benzo[d]thiazol-6-yl)ethanone;

1-(2-(2-(2-tert-butylphenoxy)pyridine-3-ylamino)benzo[d]thiazol-6-yl)ethanol;

6-(1-(benzyl(methyl)amino)ethyl)-N-(2-(2-tert-butylphenoxy)pyridin-3-yl)benzo[d]thiazol-2-amine;

6-(1-(4-(trifluoromethyl)benzyl)(methyl)amino)ethyl)-N-(2-(2-tert-butylphenoxy)pyridin-3-yl)benzo[d]thiazol-2-amine;

N-(2-(2-tert-butylphenoxy)pyridin-3-yl)benzo[d]thiazol-2-amine;

N-(2-(2-tert-butylphenoxy)pyridine-3-yl)-5-(trifluoromethyl)benzo[d]thiazol-amine;

N-(2-(2-tert-butylphenoxy)pyridine-3-yl)-6-methoxybenzo[d]thiazol-2-amine;

N-(2-(2-tert-butylphenoxy)pyridine-3-yl)-6-isopropylbenzo[d]thiazol-2-amine;

N-(2-(2-tert-butylphenoxy)pyridin-3-yl)benzo[d]thiazol-6-amine;

6-bromo-N-(2-(2-tert-butylphenoxy)pyridin-3-yl)benzo[d]thiazol-2-amine;

N-(2-(2-tert-butylphenoxy)pyridin-3-yl)-4-(methylthio)benzo[d]thiazol-2-amine;

N-(2-(2-tert-butylphenoxy)pyridin-3-yl)-7-fluoro-4-methylbenzo[d]thiazol-2-amine;

5-(benzyloxy)-N-(2-(2-tert-butylphenoxy)pyridin-3-yl)benzo[d]thiazol-2-amine;

N-(2-(2-tert-butylphenoxy)pyridin-3-yl)-5-methoxybenzo[d]thiazol-2-amine;

N-(2-(2-tert-butylphenoxy)pyridin-3-yl)-7-chloro-4-methoxybenzo[d]thiazol-2-amine;

N-(2-(2-tert-butylphenoxy)pyridin-3-yl)-4-methoxybenzo[d]thiazol-2-amine;

6-bromo-N-(2-(2-tert-butylphenoxy)pyridin-3-yl)-4-fluorobenzo[d]thiazol-2-amine;

N-(2-(2-tert-butylphenoxy)pyridin-3-yl)-6-(1H-pyrazol-1-yl)benzo[d]thiazol-2-amine;

N-(2-(2-tert-butylphenoxy)pyridin-3-yl)-6-chlorobenzo[d]thiazol-2-amine;

N-(2-(2-tert-butylphenoxy)pyridin-3-yl)-5-chlorobenzo[d]thiazol-2-amine;

N-(2-(2-tert-butylphenoxy)pyridin-3-yl)-4-chlorobenzo[d]thiazol-2-amine;

N-(2-(2-tert-butylphenoxy)pyridin-3-yl)-6-fluorobenzo[d]thiazol-2-amine;

N-(2-(2-tert-butylphenoxy)pyridin-3-yl)-6-ethoxybenzo[d]thiazol-2-amine;

N-(2-(2-tert-butylphenoxy)pyridin-3-yl)-6-nitrobenzo[d]thiazol-2-amine;

N-(2-(2-tert-butylphenoxy)pyridin-3-yl)-5,6-dimethylbenzo[d]thiazol-2-amine;

N-(2-(2-tert-butylphenoxy)pyridin-3-yl)-4,6-difluorobenzo[d]thiazol-2-amine;

N-(2-(2-tert-butylphenoxy)pyridin-3-yl)-6-methoxy-4-methylbenzo[d]thiazol-2-amine;

N-(2-(2-tert-butylphenoxy)pyridin-3-yl)-4,6,7-trimethylbenzo[d]thiazol-2-amine;

N-(2-(2-tert-butylphenoxy)pyridin-3-yl)-4,7-dimethylbenzo[d]thiazol-2-amine;

N-(2-(2-tert-butylphenoxy)pyridin-3-yl)-4-ethylbenzo[d]thiazol-2-amine;

N-(2-(2-tert-butylphenoxy)pyridin-3-yl)-4-isopropyl-benzo[d]thiazol-2-amine;
N-(2-(2-tert-butylphenoxy)pyridin-3-yl)-4,5-dimethyl-benzo[d]thiazol-2-amine;
4-bromo-N-(2-(2-tert-butylphenoxy)pyridin-3-yl)-6-isopropylbenzo[d]thiazol-2-amine;
methyl 2-(2-(2-tert-butylphenoxy)pyridin-3-ylamino)benzo[d]thiazole-4-carboxylate;
N-(2-(2-tert-butylphenoxy)pyridin-3-yl)-5-chloro-4-methylbenzo[d]thiazol-2-amine;
ethyl 2-(2-(2-tert-butylphenoxy)pyridin-3-ylamino)benzo[d]thiazole-6-carboxylate;
N-(2-(2-tert-butylphenoxy)pyridin-3-yl)-6-phenoxy-benzo[d]thiazol-2-amine;
N-(2-(2-tert-butylphenoxy)pyridin-3-yl)-7-chloro-6-methylbenzo[d]thiazol-2-amine;
6-(benzyloxy)-N-(2-(2-tert-butylphenoxy)pyridin-3-yl)benzo[d]thiazol-2-amine;
N-(2-(2-tert-butylphenoxy)pyridin-3-yl)-4-fluoro-6-methylbenzo[d]thiazol-2-amine;
N-(2-(2-tert-butylphenoxy)pyridin-3-yl)-6-(1-methoxyethyl)benzo[d]thiazol-2-amine; and
tert-butyl 6-bromobenzo[d]thiazol-2-yl(2-(2-tert-butylphenoxy)pyridin-3-yl)carbamate;

and a stereoisomer or pharmaceutically acceptable salt of any of the foregoing.

8. A pharmaceutical composition, comprising: a pharmaceutically acceptable carrier and a therapeutically effective amount of a compound of claim 7.

9. A pharmaceutical composition, comprising: a pharmaceutically acceptable carrier and a therapeutically effective amount of a compound of claim 1.

10. A pharmaceutical composition, comprising: a pharmaceutically acceptable carrier and a therapeutically effective amount of a compound of claim 2.

11. A pharmaceutical composition, comprising: a pharmaceutically acceptable carrier and a therapeutically effective amount of a compound of claim 3.

12. A pharmaceutical composition, comprising: a pharmaceutically acceptable carrier and a therapeutically effective amount of a compound of claim 4.

13. A pharmaceutical composition, comprising: a pharmaceutically acceptable carrier and a therapeutically effective amount of a compound of claim 5.

14. A pharmaceutical composition, comprising: a pharmaceutically acceptable carrier and a therapeutically effective amount of a compound of claim 6.

* * * * *

UNITED STATES PATENT AND TRADEMARK OFFICE
CERTIFICATE OF CORRECTION

PATENT NO. : 8,053,450 B2  Page 1 of 1
APPLICATION NO. : 12/104732
DATED : November 8, 2011
INVENTOR(S) : Timothy F. Herpin et al.

It is certified that error appears in the above-identified patent and that said Letters Patent is hereby corrected as shown below:

Column 167
Lines 42-43, "$C_{1-6}$ alkyl)C(O)—," should read -- ($C_{1-6}$ alkyl)C(O)—, --.

Column 169
Line 15, "—CH(Me)N(t)Bn," should read -- —CH(Me)N(Et)Bn, --.

Column 170
Line 13, "6-(1-(4" should read -- 6-(1-((4 --; and
Line 19, "thiazol-amine;" should read -- thiazol-2-amine; --.

Signed and Sealed this
Tenth Day of January, 2012

David J. Kappos
*Director of the United States Patent and Trademark Office*